United States Patent
Totrov et al.

(10) Patent No.: US 10,568,969 B2
(45) Date of Patent: Feb. 25, 2020

(54) IMMUNOGENIC POLYPEPTIDES

(71) Applicants: NEW YORK UNIVERSITY, New York, NY (US); MOLSOFT LLC, San Diego, CA (US); ICAHN SCHOOL OF MEDICINE AT MOUNT SINAI, New York, NY (US)

(72) Inventors: Maxim Totrov, San Diego, CA (US); Xunqing Jiang, Brooklyn, NY (US); Ruimin Pan, New York, NY (US); Susan Zolla-Pazner, New York, NY (US); Xiangpeng Kong, New York, NY (US)

(73) Assignees: New York University, New York, NY (US); Molsoft LLC, San Diego, CA (US); Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/695,753

(22) Filed: Sep. 5, 2017

(65) Prior Publication Data
US 2018/0071400 A1    Mar. 15, 2018

Related U.S. Application Data

(60) Provisional application No. 62/383,126, filed on Sep. 2, 2016.

(51) Int. Cl.
| | | |
|---|---|---|
| *A61K 47/64* | (2017.01) | |
| *A61K 39/21* | (2006.01) | |
| *A61K 39/385* | (2006.01) | |
| *C12N 7/00* | (2006.01) | |
| *A61P 31/12* | (2006.01) | |
| *A61K 39/12* | (2006.01) | |
| *A61K 39/00* | (2006.01) | |

(52) U.S. Cl.
CPC .......... *A61K 47/646* (2017.08); *A61K 39/12* (2013.01); *A61K 39/21* (2013.01); *A61K 39/385* (2013.01); *A61K 47/64* (2017.08); *A61K 47/6415* (2017.08); *A61P 31/12* (2018.01); *C12N 7/00* (2013.01); *A61K 2039/575* (2013.01); *A61K 2039/6037* (2013.01); *A61K 2039/70* (2013.01); *C07K 2319/30* (2013.01); *C07K 2319/35* (2013.01); *C12N 2740/16122* (2013.01); *C12N 2740/16134* (2013.01); *Y02A 50/484* (2018.01)

(58) Field of Classification Search
CPC .................. A61K 39/42; A61K 45/06; A61K 2039/5252; A61K 38/00; A61K 39/12; C07K 16/1063; C12N 2740/10011; C12N 2740/16011; C12N 2740/16111; C12N 15/8258; C12N 2710/16134; C12N 7/00
See application file for complete search history.

(56) References Cited

PUBLICATIONS

Jiang et al., "A Novel Trimeric V1V2-Scaffold Immunogen Induces V2q-Specific Antibody Responses," HIV Research for Prevention (HIVR4P) Conference, Oct. 28-31, 2014, Cape Town South Africa, Poster (2014).
Pan et al., "Structure of HIV-1 gp120 V1V2 in Complex with Human mAb 830A Reveals a 5-Stranded Beta Barrel Conformation and Integrin-Binding Site," AIDS Research and Human Retroviruses 30(S1): A18-A19 (2014).
Mayr et al., "Epitope Mapping of Confirmational V2-Specific Anti-HIV Human Monoclonal Antibodies Reveals an Immunodominant Site in V2," PLOS One 8(7):e70859 (2013).
Pan et al., "The V1V2 Region of HIV-1 gp120 Forms a Five-Stranded Beta Barrel," Journal of Virology 89 (15):8003-8010 (2015).
Spurrier et al., "Functional Implications of the Binding Mode of a Human Conformation-Depedent V2 Monoclonal Antibody against HIV," Journal of Virology 88(8):4100-4112 (2014).
Zolla-Pazner et al., "Cross-Clade HIV-1 Neutralizing Antibodies Induced with V3-Scaffold Protein Immunogens Following Priming with gp120 DNA," Journal of Virology 85(19):9887-9898 (2011).
Totrov et al., "Structure-Guided Design and Immunological Characterization of Immunogens Presenting the HIV-1 gp120 V3 Loop on a CTB Scaffold," NIH Public Access Author Manuscript, published in final edited form in Virology 405(2):513-523 (2010).
Jiang et al., "A Novel Trimeric V1V2-Scaffold Immunogen Induces V2q-Specific Antibody Responses," AIDS Research and Human Retroviruses 30(S1):A121 (2014).

*Primary Examiner* — Bao Q Li
(74) *Attorney, Agent, or Firm* — Pepper Hamilton LLP

(57) ABSTRACT

The present invention relates to isolated immunogenic polypeptides and their use. In one aspect, the isolated immunogenic polypeptide includes a scaffold polypeptide having a hairpin loop modified to include one or more epitopes heterologous to the scaffold polypeptide and from an amino acid loop linked by a disulfide bond. The scaffold polypeptide directs self-assembly with two other of the scaffold polypeptides to form a trimeric structure, which constrains the one or more epitopes to a conformation that is (i) substantially similar to one or more native pathogen epitopes in trimeric conformation and (ii) capable of binding an antibody reactive to the one or more native pathogen epitopes in trimeric conformation. Another aspect relates to an isolated immunogenic polypeptide that includes a scaffold polypeptide having a native loop modified to include one or more epitopes heterologous to the scaffold polypeptide and from an amino acid loop linked by a disulfide bond. The scaffold polypeptide directs self-assembly with four other of said scaffold polypeptides to form a pentameric structure, which constrains the one or more epitopes to a conformation capable of binding an antibody reactive to one or more native pathogen epitopes.

20 Claims, 32 Drawing Sheets
Specification includes a Sequence Listing.

Table 4. The 50%, 80%, and 90% inhibitory dose titers, ID50, ID80, and ID90, of the H3 rabbit sera against MW965 in a 30 min and a 24 hours TZM.bl neutralization assay.

| Serum # | Rabbit # | 93MW965.26(C) | | | | | |
|---|---|---|---|---|---|---|---|
| | | 30 min | | | 24h | | |
| | | ID50 | ID80 | ID90 | ID50 | ID80 | ID90 |
| 1 | H3.1.1 | | 60 | <10 | 1766 | | |
| 2 | H3.1.2 | 40 | 15 | <10 | 1633 | | |
| 3 | H3.1.3 | 10 | <10 | <10 | | 19 | 13 |
| 4 | H3.1.4 | 56 | 22 | <10 | 2575 | | |
| 5 | H3.1.5 | 61 | 40 | 35 | 3907 | 1454 | |
| 6 | H3.2.1 | 29 | <10 | <10 | 1006 | | |
| 7 | H3.2.2 | 14 | <10 | <10 | | 98 | 61 |
| 8 | H3.2.3 | 11 | <10 | <10 | 1020 | 62 | 30 |
| 9 | H3.2.4 | 12 | <10 | <10 | 1119 | | 78 |
| 10 | H3.2.5 | <10 | <10 | <10 | 24 | 16 | 13 |
| 11 | H3.3.1 | 12 | 10 | <10 | | 81 | 55 |
| 12 | H3.3.2 | 36 | 25 | <10 | 1379 | | |
| 13 | H3.3.3 | 13 | <10 | <10 | | | |
| 14 | H3.3.4 | 12 | <10 | <10 | | 62 | 37 |
| 15 | H3.3.5 | 16 | <10 | <10 | | | |
| 16 | H3.4.1 | <10 | <10 | <10 | | 65 | 41 |
| 17 | H3.4.2 | 11 | <10 | <10 | | | |
| 18 | H3.4.3 | 39 | <10 | <10 | | | |
| 19 | H3.4.4 | 11 | <10 | <10 | | | 79 |
| 20 | H3.4.5 | 10 | <10 | <10 | | | 73 |
| 21 | H3.5.1 | 11 | <10 | <10 | | | |
| 22 | H3.5.2 | 12 | <10 | <10 | | 98 | 64 |
| 23 | H3.5.3 | 17 | <10 | <10 | | | 75 |
| 25 | H3.5.5 | 25 | 14 | 10 | 1064 | | |

Figure 6C

Figure 7A:
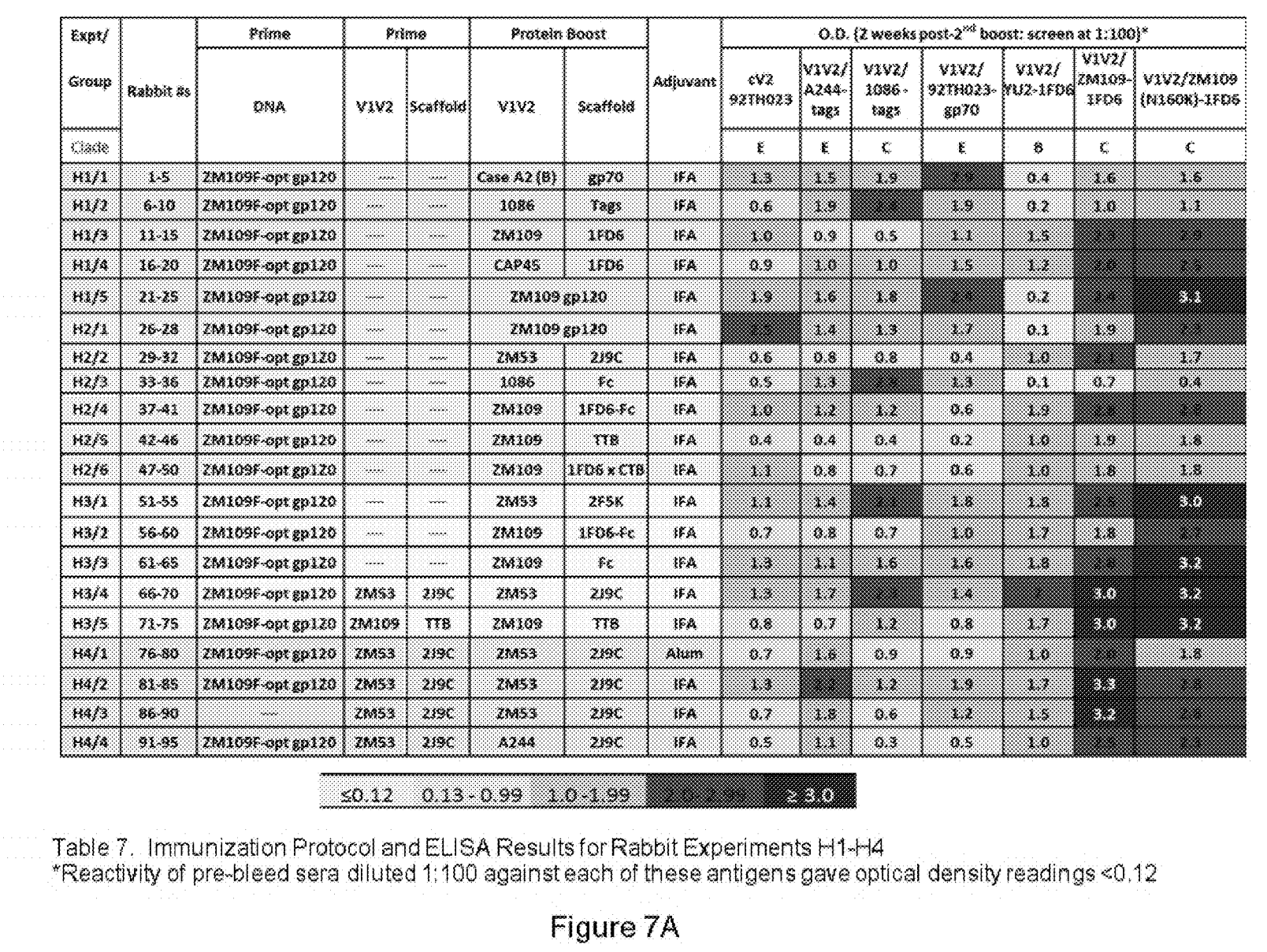

Table 7. Immunization Protocol and ELISA Results for Rabbit Experiments H1-H4
*Reactivity of pre-bleed sera diluted 1:100 against each of these antigens gave optical density readings <0.12

| Figure | Group | Prime (x3)* | Boost (x2)* | Adjuvant* | GMT₅₀⁻¹ vs. V1V2_{ZM109}-1FD6 |
|---|---|---|---|---|---|
| 9A | H2/5; blue | DNA gp120/ZM109 | V1V2/ZM109-TTB | IFA | 283 |
| 9A | H3/5; red | DNA gp120/ZM109 + V1V2/ZM109-TTB | V1V2/ZM109-TTB | IFA | 959 |
| 9B | H2/4; blue | DNA gp120/ZM109 | V1V2/ZM53-2J9C | IFA | 171 |
| 9B | H3/4; red | DNA gp120/ZM109 + V1V2/ZM53-2J9C | V1V2/ZM53-2J9C | IFA | 2246 |
| 9C | H4/1; blue | DNA gp120/ZM109 + V1V2/ZM53-2J9C | V1V2/ZM53-2J9C | Alum | 37 |
| 9C | H4/2; red | DNA gp120/ZM109 + V1V2/ZM53-2J9C | V1V2/ZM53-2J9C | IFA | 149 |
| 9D | H4/3; blue | DNA gp120/ZM109 + V1V2/ZM53-2J9C | V1V2/A244-2J9C | IFA | 23 |
| 9D | H4/4; red | DNA gp120/ZM109 + V1V2/ZM53-2J9C | V1V2/ZM53-2J9C | IFA | 149 |
| 9E | H2/2; blue | DNA gp120/ZM109 | V1V2/ZM53-2J9C | IFA | 171 |
| 9E | H3/1; red | DNA gp120/ZM109 | V1V2/ZM53-2F5K | IFA | 1412 |

Figure 9F

Table 8. Duration of the Antibody Response During and After Priming with gp120(ZM109) DNA and Boosting with gp120(ZM109) (Experimental Group H1/5).

| BLEED | Week | | ZM233 gp120 | V1V2/ YU2 1FD6 | V1V2/ ZM109 TTB | V1V2/CaseA2 gp70 | V3 ConsC |
|---|---|---|---|---|---|---|---|
| I | 0 | Pre-bleed | 0.17 | 0.09‡ | 0.12 | 0.09 | 0.08 |
| II | 2 | 2wp1p* | 0.36 | 0.09 | 0.19 | 0.10 | 0.09 |
| III | 4 | 2wp2p | 2.21 | 0.09 | 0.23 | 0.24 | 0.17 |
| IV | 6 | 2wp3p | 2.87 | 0.09 | 0.36 | 0.64 | 0.24 |
| V | 10 | 6wp3p | 2.02 | 0.10 | 0.26 | 0.57 | 0.11 |
| VI | 12 | 2wp1b | 2.98 | 0.31 | 0.84 | 1.62 | 0.44 |
| VII | 16 | 2wp2b | 2.97 | 0.34 | 1.06 | 2.07 | 0.52 |
| VIII | 18 | 4wp2b | 3.03 | 0.34 | 1.01 | 2.31 | 0.72 |
| IX | 21 | 7wp2b | 2.86 | 0.27 | 0.91 | 1.81 | 0.38 |

‡ Mean O. D. of five sera tested at 1:100; read at wavelength 405 nm. Data from 36 pre-bleed sera in various experiments used to calculate a cut-off value (mean + 3SD) of >0.14.
* Abbreviations: 2wp1p=2 weeks post first prime; 2wp2p=2 weeks post 2nd prime, etc. 2wp1b=two weeks post first boost; etc. Results during priming are shown in Bleeds I-V, and those during and after boosts in Bleeds VI-IX.

Figure 10A

Table 9. Duration of Antibody Response during and after Priming with DNA + V1V2(ZM53)-2J9C and Boosting with V1V2(ZM53)-2J9C (Experimental Group H3/4).

| BLEED | Weeks | | ZM249 gp120 | V1V2/ YU2- 1FD6 | V1V2/ ZM109-TTB | V1V2/CaseA2- gp70 | V3 ConsC |
|---|---|---|---|---|---|---|---|
| I | 0 | Pre-bleed | 0.15 | 0.09 | 0.10 | 0.09 | 0.08 |
| II | 2 | 2wp1p | 0.62 | 0.13 | 0.14 | 0.09 | 0.13 |
| III | 4 | 2wp2p | 2.38 | 1.02 | 1.00 | 0.24 | 0.28 |
| IV | 6 | 2wp3p | 2.66 | 1.99 | 1.78 | 0.45 | 0.26 |
| V | 12 | 2wp1b | 1.67 | 2.47 | 2.29 | 0.38 | 0.14 |
| VI | 16 | 2wp2b | 1.27 | 2.61 | 2.32 | 0.58 | 0.15 |
| VII | 20 | 6wp2b | 1.05 | 2.55 | 2.37 | 0.45 | 0.14 |
| VIII | 26 | 12wp2b | 1.51 | 2.48 | 2.42 | 0.38 | 0.14 |
| IX | 36 | 22wp2b | 1.39 | 2.14 | 1.87 | 0.27 | 0.12 |
| X | 57 | 43wp2b | 1.28 | 1.67 | 1.70 | 0.23 | 0.12 |
| XI | 61 | 47wp2b | 1.15 | 1.54 | 1.43 | 0.26 | 0.10 |
| XII | 69 | 55wp2b | 1.94 | 2.15 | 1.81 | 0.19 | 0.14 |
| XIII | 76 | 62wp2b | 1.63 | 1.93 | 1.79 | 0.19 | 0.14 |

‡ Mean O. D. of five sera tested at 1:100; read at wavelength 405 nm. Data from 36 pre-bleed sera in various experiments used to calculate a cut-off value (mean + 3SD) of >0.14.
* Abbreviations: 2wp1p=2 weeks post first prime; 2wp2p=2 weeks post 2nd prime, etc. 2wp1b=two weeks post first boost; etc. Results during priming are shown in Bleeds I-IV, and those during and after boosts in Bleeds V-XIII.

Figure 10B

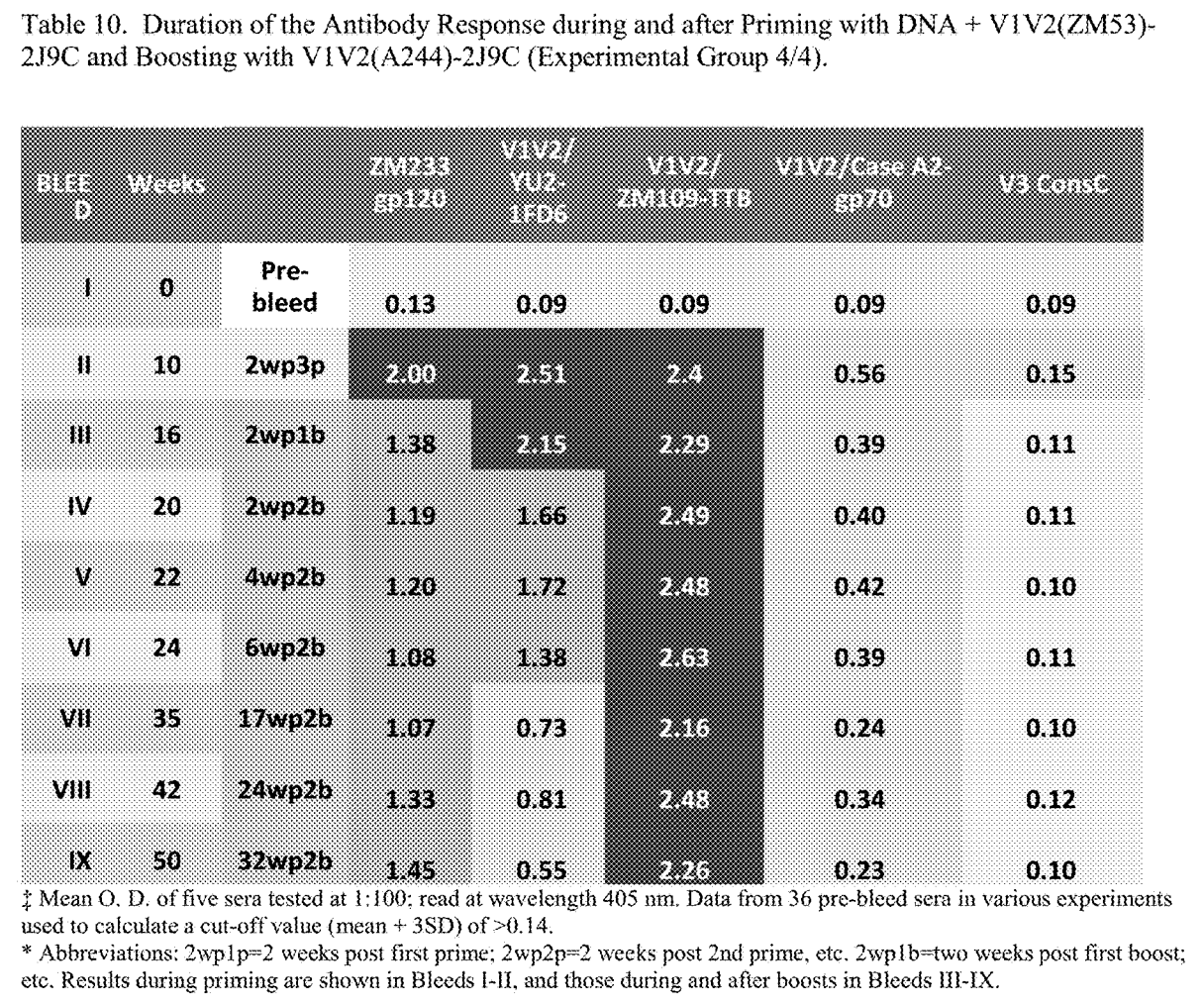

Table 10. Duration of the Antibody Response during and after Priming with DNA + V1V2(ZM53)-2J9C and

| Expt/ Group | Prime | | | Boost | | OD vs. V1V2$_{ZM109}$-1FD6 |
|---|---|---|---|---|---|---|
| | DNA | V1V2 | Scaffold | V1V2 | Scaffold | |
| H1/5 | ZM109-opt gp120 | | | ZM109 gp120 | | 2.4 |
| H2/4 | ZM109-opt gp120 | - | - | ZM109 | 1FD6-Fc | 2.8 |
| H2/5 | ZM109-opt gp120 | | | ZM109 | | |
| H3/1 | ZM109-opt gp120 | - | - | ZM53 | 2FSK | 3.4 |
| H3/4 | ZM109-opt gp120 | ZM53 | 1FD6 | ZM53 | 1FD6 | 0.5 |
| H4/4 | ZM109-opt gp120 | ZM53 | 2J9C | A244 | 2J9C | 2.5 |

IMMUNOGENIC POLYPEPTIDES

This application claims the benefit of U.S. Provisional Patent Application Ser. No. 62/383,126, filed Sep. 2, 2016, which is hereby incorporated by reference in its entirety.

This invention was made with government support under P01 AI 100151 awarded by National Institutes of Health. The government has certain rights in the invention.

FIELD OF THE INVENTION

The present invention is related to rationally designed immunogenic polypeptides (also referred to as immunogens), as well as compositions and methods relating thereto.

BACKGROUND OF THE INVENTION

Conventional approaches to vaccine development have implemented either whole replication competent virus which has been attenuated (e.g., Sabin polio vaccine, measles, mumps, rubella (MMR)) or inactivated virions that are not replication competent. On occasions, the inactivated virus vaccines may include split vaccines where the virus particles have been disrupted. Molecular techniques have also been used to develop the subunit vaccine (e.g., hepatitis B vaccine) that consists only of the surface glycoproteins of hepatitis B virus. The inactivated virus vaccines tend to induce primarily antibody (Ab) responses to the viruses in question, whereas the live attenuated vaccines induce both cell-mediated immunity as well as an antibody response since the vaccine induces a transient infection.

The only disease which has been eliminated by virtue of a successful vaccination campaign is smallpox. A campaign is currently in progress to eradicate polio. Features of virus infections that can be eliminated by vaccination are infections caused by viruses with stable virus antigens (i.e., very low mutation frequency, few subtypes), that lack a reservoir in other animal species, viruses that do not persist in the body once the infection is over and where vaccination leads to long lasting immunity. Viruses such as polio and measles fulfill these criteria whereas viruses such as influenza virus (Flu), HCV, and HIV that vary their protein sequences do not. It is for this reason that new and alternate approaches are required.

With regard to HIV, the HIV-1 envelope (Env) complex of glycoproteins gp120 and gp41 is the target for neutralizing antibodies (Abs) induced in HIV-1 infected patients and for HIV/AIDS vaccine development (Wyatt et al., "The HIV-1 Envelope Glycoproteins: Fusogens, Antigens, and Immunogens," Science 280:1884-1888 (1998); Ward et al., "Insights into the Trimeric HIV-1 Envelope Glycoprotein Structure," Trends Biochem. Sci. 40:101-107 (2015)). Glycoprotein gp120 has been conventionally divided into five variable and five conserved regions (Modrow et al., "Computer-Assisted Analysis of Envelope Protein Sequences of Seven Human Immunodeficiency Virus Isolates: Prediction Of Antigenic Epitopes in Conserved and Variable Regions," J. Virol. 61:570-578 (1987)), and the region of the first and second variable loops (V1V2) is the most diverse region of Env in both sequence and length (Zolla-Pazner et al., "Structure-Function Relationships of HIV-1 Envelope Sequence-Variable Regions Refocus Vaccine Design," Nat. Rev. Immunol. 10:527-535 (2010)). However, recent data have shown that V1V2 can form, in the structurally constrained scaffolded V1V2 or the stabilized BG505 SOSIP.664 trimer, a unique five-stranded β-barrel structure with strands A, B, C, C', and D (Pancera et al., "Structure and Immune Recognition of Trimeric Pre-Fusion HIV-1 Env," Nature 514:455-461 (2014); Pan et al., "The V1V2 Region of HIV-1 gp120 Forms a Five-Stranded Beta Barrel," J. Virol. 89:8003-8010 (2015)). In the trimer context, the V1V2 domain is located at the distal apex of the Env trimer, and the three V1V2 regions in the trimer join together at the apex center to form a top layer of the Env complex (Pancera et al., "Structure and Immune Recognition of Trimeric Pre-Fusion HIV-1 Env," Nature 514:455-461 (2014); Julien et al., "Crystal Structure of a Soluble Cleaved HIV-1 Envelope Trimer," Science 342:1477-1483 (2013); Lyumkis et al., "Cryo-EM Structure of a Fully Glycosylated Soluble Cleaved HIV-1 Envelope Trimer," Science 342:1484-1490 (2013); Lee et al., "Cryo-EM Structure of a Native, Fully Glycosylated, Cleaved HIV-1 Envelope Trimer," Science 351:1043-1048 (2016)). This layer can shield the co-receptor binding sites as well as partially occlude the third variable region (V3); it can also make large movements upon CD4 receptor binding to expose the co-receptor binding sites (Pancera et al., "Structure and Immune Recognition of Trimeric Pre-Fusion HIV-1 Env," Nature 514:455-461 (2014); Munro et al., "Conformational Dynamics of Single HIV-1 Envelope Trimers on the Surface of Native Virions," Science 346:759-763 (2014); Spurrier et al., "Structural Analysis of Human and Macaque Mabs 2909 and 2.5B: Implications for the Configuration of the Quaternary Neutralizing Epitope of HIV-1 Gp120," Structure 19:691-699 (2011)). V1V2 also harbors a putative integrin-binding site that may also mediate Env binding to host cells (Arthos et al., "HIV-1 Envelope Protein Binds to and Signals Through Integrin Alpha4beta7, the Gut Mucosal Homing Receptor For Peripheral T Cells," Nat. Immunol. 9:301-309 (2008); Tassaneetrithep et al., "Cryptic Determinant of alpha4beta7 Binding in the V2 Loop of HIV-1 gp120," PLoS One 9:e108446 (2014); Peachman et al., "Identification of New Regions in HIV-1 gp120 Variable 2 and 3 Loops That Bind to alpha4beta7 Integrin Receptor," PLoS One 10:e0143895 (2015)). One such site, the tripeptide LDI/V motif at amino acid positions 179-181 (HxB2 numbering) (Ratner et al., "Complete Nucleotide Sequences of Functional Clones of the AIDS Virus," AIDS Res Hum. Retroviruses 3:57-69 (1987), which is hereby incorporated by reference in its entirety), is located at the beginning of the C' strand in the β-barrel (Pan et al., "The V1V2 Region of HIV-1 gp120 Forms a Five-Stranded Beta Barrel," J. Virol. 89:8003-8010 (2015)).

The spatial location of V1V2 on the surface of the Env spike makes it a natural target for the human immune system. HIV-infected individuals can make cross-reactive V1V2 Abs, and many human anti-V1V2 monoclonal antibodies (mAbs) have been isolated (Moore et al., "Probing the Structure of the V2 Domain of Human Immunodeficiency Virus Type 1 Surface Glycoprotein gp120 With a Panel of Eight Monoclonal Antibodies: Human Immune Response to the V1 and V2 Domains," J. Virol. 67:6136-6151 (1993); Gorny et al., "Human Anti-V2 Monoclonal Antibody That Neutralizes Primary But Not Laboratory Isolates of Human Immunodeficiency Virus Type 1," J. Virol. 68:8312-8320 (1994); Gorny et al. "Identification of a New Quaternary Neutralizing Epitope on Human Immunodeficiency Virus Type 1 Virus Particles," J. Virol. 79:5232-5237 (2005); Walker et al., "Broad and Potent Neutralizing Antibodies from an African Donor Reveal a New HIV-1 Vaccine Target," Science 326:285-289 (2009); Bonsignori et al., "Analysis of a Clonal Lineage of HIV-1 Envelope V2/V3 Conformational Epitope-Specific Broadly Neutralizing Antibodies and Their Inferred Unmutated Common Ancestors," J. Virol. 85:9998-10009 (2011); Doria-Rose et al., "Developmental Pathway For Potent V1V2-Directed HIV-Neutralizing Antibodies," *Nature* 509:55-62 (2014); Israel et al., "Prevalence of a V2 Epitope in Clade B Primary Isolates and its Recognition by Sera from HIV-1-Infected Individuals," *AIDS* 11:128-130 (1997); Liao et al., "Vaccine Induction of Antibodies Against a Structurally Heterogeneous Site of Immune Pressure Within HIV-1 Envelope Protein Variable Regions 1 and 2," *Immunity* 38:176-186 (2013)). Epitopes for some of these mAbs have been characterized, and were recently classified into three major types—V2i, V2p, and V2q (Mayr et al., "Epitope Mapping of Conformational V2-Specific Anti-HIV Human Monoclonal Antibodies Reveals an Immunodominant Site in V2," *PLoS One* 8:e70859 (2013); Spurrier et al., "Functional Implications of the Binding Mode of a Human Conformation-Dependent V2 Monoclonal Antibody Against HIV," *J. Virol.* 88:4100-4112 (2014)). The V2i type is defined by a panel of human mAbs, including 830A, 697-D, and 2158 (Gorny et al., "Human Anti-V2 Monoclonal Antibody That Neutralizes Primary But Not Laboratory Isolates of Human Immunodeficiency Virus Type 1," *J. Virol.* 68:8312-8320 (1994); Mayr et al., "Epitope Mapping of Conformational V2-Specific Anti-HIV Human Monoclonal Antibodies Reveals an Immunodominant Site in V2," *PLoS One* 8:e70859 (2013); Spurrier et al., "Functional Implications of the Binding Mode of a Human Conformation-Dependent V2 Monoclonal Antibody Against HIV," *J. Virol.* 88:4100-4112 (2014); Gorny et al., "Functional and Immunochemical Cross-Reactivity of V2-Specific Monoclonal Antibodies From HIV-1-Infected Individuals," *Virology* doi:10.1016/j.virol.2012.02.003 (2012); Nyambi et al., "Conserved and Exposed Epitopes on Intact, Native, Primary Human Immunodeficiency Virus Type 1 Virions of Group M," *J Virol* 74:7096-7107 (2000); Pinter et al., "The V1/V2 Domain of Gp120 is a Global Regulator of the Sensitivity of Primary Human Immunodeficiency Virus Type 1 Isolates to Neutralization by Antibodies Commonly Induced Upon Infection," *J. Virol.* 78:5205-5215 (2004)). Extensive immunological, mutagenesis and structural data have shown that the V2i epitopes overlap with the LDI/V integrin-binding site, and Abs of this family recognize discontinuous regions in V1V2 (Pan et al., "The V1V2 Region of HIV-1 gp120 Forms a Five-Stranded Beta Barrel," *J. Virol.* 89:8003-8010 (2015); Mayr et al., "Epitope Mapping of Conformational V2-Specific Anti-HIV Human Monoclonal Antibodies Reveals an Immunodominant Site in V2," *PLoS One* 8:e70859 (2013); Spurrier et al., "Functional Implications of the Binding Mode of a Human Conformation-Dependent V2 Monoclonal Antibody Against HIV," *J. Virol.* 88:4100-4112 (2014); Gorny et al., "Functional and Immunochemical Cross-Reactivity of V2-Specific Monoclonal Antibodies From HIV-1-Infected Individuals," *Virology* 427(2):198-207 (2012)). The V2p type is defined by human mAbs CH58 and CH59 isolated from a vaccinee of the Phase III RV144 human vaccine trial (Liao et al., "Vaccine Induction of Antibodies Against a Structurally Heterogeneous Site of Immune Pressure Within HIV-1 Envelope Protein Variable Regions 1 And 2," *Immunity* 38:176-186 (2013); Rerks-Ngarm et al., "Vaccination with ALVAC and AIDSVAX to Prevent HIV-1 Infection in Thailand," *N. Engl. J. Med.* 361:2209-2220 (2009); Bonsignori et al. "Antibody-Dependent Cellular Cytotoxicity-Mediating Antibodies From an HIV-1 Vaccine Efficacy Trial Target Multiple Epitopes and Preferentially Use the VH1 Gene Family," *J. Virol.* 86:1152111532 (2012)). Monoclonal Abs CH58 and CH59 react with V2 peptides, indicating that the V2p epitopes are structurally unconstrained and have a helical or helical-coil structure (Liao et al., "Vaccine Induction of Antibodies Against a Structurally Heterogeneous Site of Immune Pressure Within HIV-1 Envelope Protein Variable Regions 1 And 2," *Immunity* 38:176-186 (2013)). The V2q type was defined as a quaternary neutralizing epitope and is represented by mAb, including human mAbs PG9 and PG16 (Walker et al., "Broad and Potent Neutralizing Antibodies From an African Donor Reveal a New HIV-1 Vaccine Target," *Science* 326:285-289 (2009)). Crystal structures of PG9 and PG16 in complex with engineered V1V2 scaffolds have shown that these mAbs recognize a region in strand C of V1V2, via a strand-strand interaction, as well as two N-linked glycans using the head of the long CDR H3 region harbored by these V2q mAbs (McLellan et al., "Structure of HIV-1 gp120 V1/V2 Domain With Broadly Neutralizing Antibody PG9," *Nature* 480:336-343 (2011); Pancera et al., "Structural Basis For Diverse N-Glycan Recognition by HIV-1-Neutralizing V1-V2-Directed Antibody PG16," *Nat. Struct. Mol. Biol.* 20:804-813 (2013)). In the V1V2-scaffolds used to crystallize these mAbs, the V1V2 (from ZM109 or CAP45) is grafted into a β-hairpin region in the protein G B1 domain (PDB ID 1FD6) so that the V1V2 is structurally constrained to maintain the conformation found in the trimeric apex (Pancera et al., "Structure and Immune Recognition of Trimeric Pre-Fusion HIV-1 Env," *Nature* 514:455-461 (2014)). Although the protein region of the V2q epitopes overlaps that of the V2p epitopes, the structure for former have a β-strand conformation while that for the latter a helical conformation. The V2p mAbs have weak and very restricted neutralizing activity (Liao et al., "Vaccine Induction of Antibodies against a Structurally Heterogeneous Site of Immune Pressure within HIV-1 Envelope Protein Variable Regions 1 And 2," *Immunity* 38:176-186 (2013)), while the V2q-specific mAbs PG9 and PG16 have been shown to neutralize greater than 70% of virus strains tested (Walker et al., "Broad and Potent Neutralizing Antibodies from an African Donor Reveal a New HIV-1 Vaccine Target," *Science* 326:285-289 (2009)). Thus, the V2q epitope region can be a major site of vulnerable on Env; designing immunogens that can induce Ab responses that target this conformation has not yet been accomplished.

Data from the correlates analysis of the human clinical vaccine trial RV144, the only human vaccine trial with moderate but significant efficacy against HIV-1 acquisition, have demonstrated that vaccine-induced IgG Abs targeting V1V2 inversely correlated with the risk of infection (Haynes et al., "Immune-Correlates Analysis of an HIV-1 Vaccine Efficacy Trial," *The New England Journal of Medicine* 366:1275-1286 (2012)), and immunologic data delineated the specificity and cross-reactivity of these Abs (Zolla-Pazner et al., "Vaccine-Induced IgG Antibodies to V1V2 Regions of Multiple HIV-1 Subtypes Correlate with Decreased Risk of HIV-1 Infection," *PLoS One* 9:e87572 (2014); Zolla-Pazner et al., "Analysis of V2 Antibody Responses Induced in Vaccinees in the ALVAC/AIDSVAX HIV-1 Vaccine Efficacy Trial," *PLoS One* 8:e53629 (2013)). The Abs induced by the vaccine reacted with a V1V2-MuLV gp70 fusion protein, a reagent recognized by the V2i Abs (Gorny et al., "Functional and Immunochemical Cross-Reactivity of V2-Specific Monoclonal Antibodies From HIV-1-Infected Individuals," *Virology* doi:10.1016/j.virol.2012.02.003 (2012)). There was no evidence of the elicitation of V2q Abs by the RV144 vaccine in that little neutralizing activity was detected, and neutralization was not associated with reduced infection rates (Haynes et al., "Immune-Correlates Analysis of an HIV-1 Vaccine Efficacy Trial," *The New England Journal of Medicine* 366:1275-1286 (2012); Montefiori et al., "Magnitude and Breadth of the Neutralizing Antibody Response in The RV144 and Vax003 HIV-1 Vaccine Efficacy Trials," *J. Infect. Dis.* 206:431-441 (2012)). A sieve analysis that compared the V1V2 sequences of viruses from placebo and those from vaccine recipients identified two positions of immune pressure on the virus in V2, residues 169 and 181, supporting the hypothesis that V1V2 Abs correlated with the reduced risk of infection (Rolland et al., "Increased HIV-1 Vaccine Efficacy Against Viruses with Genetic Signatures in Env V2," *Nature* 490:417-420 (2012)). These findings suggest that V1V2 can serve as an important target for HIV vaccine development, but the modest efficacy of RV144 indicates the need for a more efficacious vaccine.

Non-neutralizing antibodies (Abs) can protect against various viral infections, contributing to protection from alphaviruses, flaviviruses, respiratory syncytial virus, and cytomegalovirus, among others (reviewed in Excler et al., "Nonneutralizing Functional Antibodies: A New 'Old' Paradigm for HIV Vaccines," *Clin. Vaccine Immunol.* 21:1023-1036 (2014); Schmaljohn, A., "Protective Antiviral Antibodies That Lack Neutralizing Activity," *Current HIV Res.* 11:345-353 (2013)). While the specificity and affinity of non-neutralizing Abs are dependent on the Fab fragment of Abs to target virions and infected cells, many biologic activities of these Abs are a function of the Fc fragment. Such activities include Ab-dependent cellular cytotoxicity (ADCC), Ab-dependent cellular phagocytosis (ADCP), Ab-dependent cell-mediated virus inhibition (ADCVI), complement activation and fixation, degranulation, and the release of pro-inflammatory cytokines (Holl et al., "Antibody-Mediated Fcgamma Receptor-Based Mechanisms of HIV Inhibition: Recent Findings and New Vaccination Strategies," *Viruses* 1:1265-1294 (2009)). Specific examples include protection from herpes simplex 2 in mice by non-neutralizing Abs which mediate ADCC (Balachandran et al., "Protection Against Lethal Challenge of BALB/c Mice by Passive Transfer of Monoclonal Antibodies to Five Glycoproteins of Herpes Simplex Virus Type 2," *Infect. and Immunity* 37:1132-1137 (1982); Gorander et al., "Anti-Glycoprotein G Antibodies of Herpes Simplex Virus 2 Contribute to Complete Protection After Vaccination in Mice and Induce Antibody-Dependent Cellular Cytotoxicity and Complement-Mediated Cytolysis," *Viruses* 6:4358-4372 (2014); Petro et al., "Herpes Simplex Type 2 Virus Deleted in Glycoprotein D Protects Against Vaginal, Skin and Neural Disease," *Elife* 4:e06054 (2015)), and protection from influenza in mice by non-neutralizing Abs targeting the head or stalk of the influenza hemagglutinin (DiLillo et al., "Broadly Neutralizing Hemagglutinin Stalk-Specific Antibodies Require FcgammaR Interactions for Protection Against Influenza Virus in Vivo," *Nat. Med.* 20:143-151 (2014); Henry et al., "Both Neutralizing and Non-Neutralizing Human H7N9 Influenza Vaccine-Induced Monoclonal Antibodies Confer Protection," *Cell Host Microbe* 19:800-813 (2016)).

The present invention is directed to overcoming these and other deficiencies in the art.

SUMMARY OF THE INVENTION

A first aspect of the present invention is directed to an isolated immunogenic polypeptide. The isolated immunogenic polypeptide includes a scaffold polypeptide having a hairpin loop. The hairpin loop is modified to include one or more epitopes heterologous to the scaffold polypeptide and from an amino acid loop linked by a disulfide bond. The scaffold polypeptide directs self-assembly with two other of the scaffold polypeptides to form a trimeric structure, where the trimeric structure constrains the one or more epitopes to a conformation that is (i) substantially similar to one or more native pathogen epitopes in trimeric conformation and (ii) capable of binding an antibody reactive to the one or more native pathogen epitopes in trimeric conformation.

A second aspect of the present invention is directed to an isolated trimeric structure including three monomeric immunogenic polypeptide subunits assembled in a trimeric structure. Each of the immunogenic polypeptide subunits includes the isolated immunogenic polypeptide according to the preceding paragraph, where the trimeric immunogenic structure constrains the one or more epitopes to the conformation that (i) is substantially similar to the one or more native epitopes of the pathogen in trimeric conformation and (ii) binds the antibody reactive to the pathogen.

A third aspect of the present invention relates to an immunogenic composition including the isolated immunogenic polypeptide according to the first aspect of the present invention and/or the isolated trimeric structure according to the second aspect of the present invention. The immunogenic composition also includes an immunologically and pharmaceutically acceptable vehicle or excipient.

A fourth aspect of present invention relates to a method of inducing, in a subject, an antibody response against a pathogen. The method involves administering to the subject the immunogenic polypeptide according to the first aspect of the present invention and/or the isolated trimeric structure according to the second aspect of the present invention under conditions effective to induce, in the subject, an antibody response against the pathogen.

A fifth aspect of the present invention relates to a method of inducing, in a subject, an antibody response against a pathogen. The method involves administering to the subject the immunogenic composition according to the third aspect of the present invention under conditions effective to induce, in the subject, an antibody response against the pathogen.

A sixth aspect of the present invention relates to an isolated immunogenic polypeptide. The isolated immunogenic polypeptide includes a scaffold polypeptide having a native loop. The native loop is modified to include one or more epitopes heterologous to the scaffold polypeptide and from an amino acid loop linked by a disulfide bond, where the scaffold polypeptide directs self-assembly with four other of said scaffold polypeptides to form a pentameric structure. The pentameric structure constrains the one or more epitopes to a conformation capable of binding an antibody reactive to one or more native pathogen epitopes.

A seventh aspect of the present invention relates to an isolated pentameric structure including five monomeric immunogenic polypeptide subunits assembled in a pentameric structure. Each of the immunogenic polypeptide subunits includes the isolated immunogenic polypeptide according to the sixth aspect of the present invention, where the pentameric structure constrains the one or more epitopes to the conformation that binds the antibody reactive to the pathogen.

An eighth aspect of the present invention relates to an immunogenic composition including the isolated immunogenic polypeptide according to the sixth aspect of the present invention and/or the pentameric structure of the seventh aspect of the present invention. The immunogenic composition also includes an immunologically and pharmaceutically acceptable vehicle or excipient.

A ninth aspect of the present invention relates to a method of inducing, in a subject, an antibody response against a pathogen. The method involves administering to the subject the immunogenic polypeptide according to the sixth aspect of the present invention and/or the isolated pentameric structure according to the seventh aspect of the present invention under conditions effective to induce, in the subject, an antibody response against the pathogen.

A tenth aspect of the present invention relates to a method of inducing, in a subject, an antibody response against a pathogen. The method involves administering to the subject the immunogenic composition according to the eighth aspect of the present invention under conditions effective to induce, in the subject, an antibody response against the pathogen.

Designing immunogens targeting various epitopes of V1V2 and dissecting Ab responses targeting the three epitope types in animal models will help further improve upon current vaccine candidates. It is shown here that immunogens presenting various representations of the V1V2 epitopes can be rationally designed and that these different immunogens induce distinct Ab responses targeting the particular defined epitopes within this region. These results provide a proof of principle that vaccine candidates targeting the V1V2 vulnerable sites can be rationally designed.

Correlates analysis of the RV144 HIV-1 vaccine trial suggested that the presence of antibodies to the V1V2 region of HIV-1 gp120 was responsible for the modest protection observed in the trial. In addition V1V2 harbors one of the key vulnerable sites of HIV-1 Env recognized by a family of broadly neutralizing mAbs such as PG9. Thus V1V2 is a key target for vaccine development. However, this vulnerable site is structurally polymorphic, and designing immunogens that present different conformations is crucial for targeting this site. It is shown here that such immunogens could be designed and they induced conformation-specific antibody responses in rabbits. These immunogens are therefore prototypes of vaccine candidates targeting the V1V2 region of HIV-1 Env.

Given findings in monkeys and man described infra, there is a great need for development of a vaccine to elicit an Fc-mediated Ab response. It was hypothesized that targeting the Ab response to V2 with rationally designed immunogens would improve the functional Ab quality and provide a basis for enhanced efficacy of HIV immunization protocols. In the work described herein, the immunogenicity of twelve V1V2-scaffold protein immunogens was tested. The results show the induction of V2-specific Abs that are reactive with V1V2 and with gp120 Envs from diverse strains and clades. After priming with gp120 DNA+/–V1V2-scaffold protein immunogens, followed by boosting with V1V2-scaffold proteins, a durable Ab response was successfully focused on the V1V2 region. This is the first immunogenicity study using rationally-designed V1V2-targeting vaccine constructs. Like the previously published studies with V3-scaffold immunogens (Totrov et al., "Structure-Guided Design and Immunological Characterization of Immunogens Presenting the HIV-1 gp120 V3 Loop on a CTB Scaffold," *Virology* 405:513-523 (2010); Zolla-Pazner et al., "Cross-Clade HIV-1 Neutralizing Antibodies Induced With V3-Scaffold Protein Immunogens Following Priming With gp120 DNA," *J. Virol.* 85:9887-9898 (2011), which are hereby incorporated by reference in their entirety), the V1V2-scaffold immunogens induced Abs that recapitulate the specificity and activities of the human V1V2-specific mAbs whose epitopes were used as templates for the design of the V1V2-scaffold immunogens (Pan et al., "The V1V2 Region of HIV-1 gp120 Forms a Five-Stranded Beta Barrel," *J. Virol.* 89:8003-8010 (2015), which is hereby incorporated by reference in its entirety), and importantly, the induced Abs display a biologic activity—in this case Fc-mediated ADCP—which has been associated with protection from infection with HIV, SHIV and SIV (Chung et al., "Polyfunctional Fc-Effector Profiles Mediated by IgG Subclass Selection Distinguish RV144 and VAX003 Vaccines," *Sci. Transl. Med.* 6:228ra238 (2014); Chung et al., "Dissecting Polyclonal Vaccine-Induced Humoral Immunity Against HIV Using Systems Serology," *Cell* 163:988-998 (2015); Barouch et al., "Protective Efficacy of a Global HIV-1 Mosaic Vaccine Against Heterologous SHIV Challenges in Rhesus Monkeys," *Cell* 155:531539 (2013); Barouch et al., "Protective Efficacy of Adenovirus/Protein Vaccines Against SIV Challenges in Rhesus Monkeys," *Science* 349:320-324 (2015), which are hereby incorporated by reference in their entirety).

Novel immunogens were designed to focus the antibody response of rabbits on the V1V2 epitopes of HIV-1 gp120 since such antibodies were associated with reduced infection rates of HIV, SIV, and SHIV. The vaccine-induced antibodies were broadly cross-reactive with the V1V2 regions of HIV subtypes B, C and E, and importantly, facilitated Fc-mediated phagocytosis, an activity not induced upon immunization of rabbits with gp120. This is the first immunogenicity study of vaccine constructs that focuses the antibody response on V1V2 and induces V2-specific antibodies with the ability to mediate phagocytosis, an activity that has been associated with protection from infection with HIV, SIV and SHIV.

BRIEF DESCRIPTION OF THE DRAWINGS

FIG. 1A shows the geometric parameters of the β-hairpin orientation of the V1V2 stem used for scaffold filtering. The 3-fold axis (the vertical blue line) of the trimer, the distance (R) of the V1V2 stem from the axis, and tilting angles ($\alpha$ and $\beta$) of the V1V2 stem are illustrated. FIG. 1B shows differences in stem orientation between V1V2 domain complexes with mAb PG9 (magenta) and mAb 830A (green). Stem strands (highlighted in grey) are superimposed, β-barrels and their axes are indicated schematically as cylinders, and arrows highlight the change in barrel orientation. FIG. 1C is a top view of V1V2(ZM53)-2J9C. The trimeric scaffold (PDB ID 2J9C) is colored grey while the three V1V2s, based on the mAb 830A complexed structure, are colored in green (darker shading, top), orange (darker shading, bottom left), and gold (darker shading, bottom right), respectively. FIG. 1D is a top view of V1V2(ZM109)-TTB. The typhoid toxin subunit B (TTB) pentamer is shown in grey while the V1V2 inserts, shown here as the PG9-bound form, are colored (darker shading). Note that the V1V2s are placed on top of the pentamer without any hindrance against each other.

FIGS. 2E-2F show titration of mAbs PG9 and CH58 to V1V2(ZM109)-1FD6 (FIG. 2E) and V1V29 (ZM109)-Fc (FIG. 2F). Note that, although these two V1V2-scaffold antigens have the same V1V2 sequence, the structurally constrained V1V2(ZM109)-1FD6 only binds PG9 while the unconstrained V1V2(ZM109)-Fc only CH58. Thus the V2q epitope type (recognized by PG9) and the V2p epitope type (recognized by CH58) could be selectively presented by the structurally constrained and unconstrained V1V2 immunogens, respectively.

FIG. 4A is an illustration of the competition assay set up. FIG. 4B demonstrates, to establish the baseline, each V1V2 mAb was first competed against itself. Shown here is V2q mAb PG9 (blue, curved graphed line) competed with itself for structurally constrained antigen V1V2 (ZM109)-1FD6 coated on the plate using PBS (red, straight graphed line) as a negative control. FIGS. 4C-4F show competition of mAbs V2q mAb PG9, V2i mAbs 697-D and 830A, and V2p mAb CH58 by biotinylated mAbs PG9 (FIG. 4C), 697-D (FIG. 4E), and 830A (FIG. 4F), respectively, for V1V2(ZM109)-1FD6 coated on the plated. Panel D shows competition of the same mAbs by biotinylated V2p mAb CH58 for V1V2(1086)-tags. Note that PG9 and CH58 each only competed with itself (FIGS. 4C and 4D), while V2i mAb 830A and 697-D competed with each other. Although CH58 does not bind V1V2(ZM109)-1FD6 and PG9 does not bind V1V2(1086)-tags, they were included for references.

FIGS. 5A-5B show results of rabbit sera competed against V2q mAb PG9 (FIG. 5A) and V2p mAb CH58 (FIG. 5B). Sera from individual rabbits of each group were tested separately, and only the curve of a representative rabbit of those groups that demonstrated clear competition is shown. Sera from rabbit H2.4.3 did not show strong competition with PG9, different from that of rabbit H2.4.1 in the figure and the other three rabbits in the group. This is likely due to animal variations. As references, black curves from data of pre-bleeds and competition against the same mAb are included. FIGS. 5C-5D show competition against V2q mAb PG9 and V2p mAb CH58, respectively, by sera from rabbits immunized with either structurally constrained V1V2(ZM109)-1FD6-Fc or the unconstrained V1V2 (ZM109)-Fc.

FIGS. 6A-6B show neutralization of the H3 rabbit sera against the tier 1B ZM109 strain in 30 min (FIG. 6A) and 24 hour (FIG. 6B) incubation neutralization assays. Vertical lines separate each animal group, and the boosting immunogen used for each group is labeled on the top of the two panels. The assays were duplicated and the lines in the data points are the averages. Note that sera of several animals, including those immunized with trimeric immunogens V1V2(ZM53)-2F5K and V1V2(ZM53)-2J9C which have V1V2 sequence heterologous from ZM109, reached above 50% neutralization (dashed line) in the 24 hours incubation. FIG. 6C is a table (Table 4), showing the 50%, 80%, and 90% inhibitory dose titers, ID50, ID80, and ID90, of the H3 rabbit sera against MW965 in a 30 min and a 24 hours TZM.b1 neutralization assay.

Figures 7D, 7E:
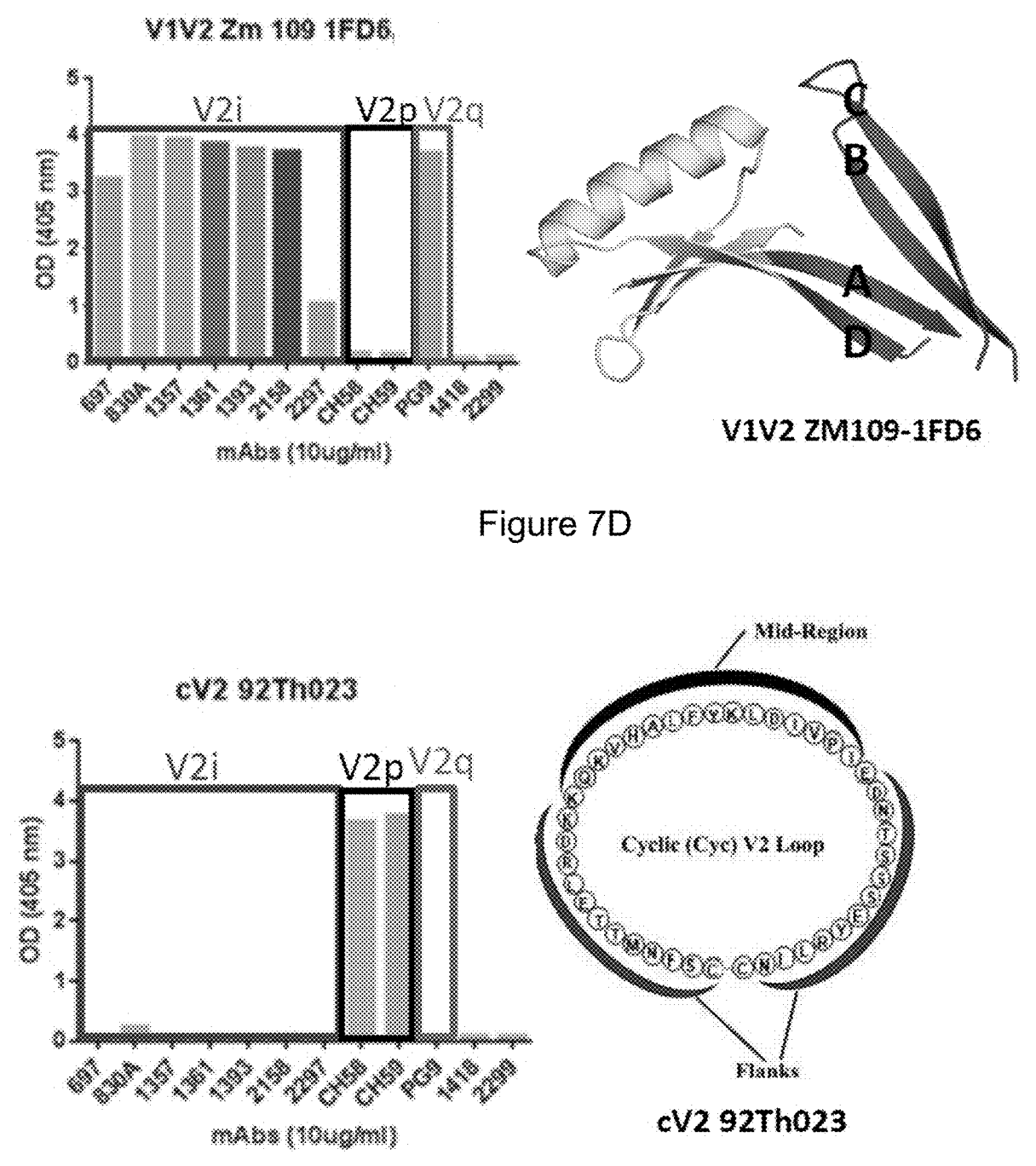

FIGS. 7A-7E show a table (FIG. 7A) and results of monoclonal antibody (mAb) reactivity against various V1V2-scaffolds (FIGS. 7B-7E). FIG. 7A is a table (Table 7) that sets out immunization protocol and ELISA results for rabbit experiments H1-H4 described herein. The optical density (OD) of the ELISA reaction between several human mAbs (used at a dilution of 10 µg/ml) and various V1V2-scaffold antigens is shown in FIG. 7C and the left panels of FIGS. 7B, 7D, and 7E. Monoclonal Abs are designated as being specific for V2i, V2p, or V2q epitopes, as defined in the text. Diagrams of V1V2(A244)-tags (FIG. 7B, right panel), of the V1V2(ZM109)-1FD6 (FIG. 7D, right panel) and cV292TH023 (FIG. 7E, right panel), used as antigens in these ELISAs, are shown. For V1V2(ZM109)-1FD6, V1V2 is shown in purple (darker shaded), and 1FD6 in gray (lighter shaded). The four strands, A, B, C, and D of V1V2 are marked. Negative controls consisted of human mAb 1418, specific for parvovirus B19, and human mAb 2299, specific for gp70 of murine leukemia virus.

FIGS. 9A-9F are radar graphs showing antibody responses in sera obtained from immunized rabbits drawn two weeks after the second boost. FIGS. 9A-9E show OD values for sera diluted 1:100. FIG. 9F shows the details of the immunization of each group of animals, along with the mean reciprocal half-maximal titers of sera from individual rabbits in each group ($GMT_{50}^{-1}$) for ELISA experiments in which V1V2(ZM109)-1FD6 was used as the coating antigen. Underlining denotes the difference in the immunization regimens between the two experiments in each pair compared. In each of FIGS. 9A-9E, the interior plotted line of the radar graph is referred to as blue in FIG. 9F and is encircled by an exterior plotted line that is referred to as red in FIG. 9F.

FIGS. 10A-10C are tables showing results for Ab responses against various antigens for three groups of animals. To determine the durability of the immune response elicited with various immunogens and vaccine regimens, selected groups of rabbits were housed for up to 76 weeks and bled at various times after each immunization. The kinetics and the duration of the Ab responses against various antigens are shown for three groups of animals in Tables 8, 9, and 10 (FIGS. 10A, 10B, and 10C, respectively).

As shown in FIG. 11A, beads were coated with gp120(ZM53) and then incubated with the designated mAb (V2i-specific mAbs 830A or 697, or V3-specific mAb 3869). Cells that had been pre-incubated for 30 min at 37° C. with either 30 µl of FcR blocking agent (Fcblock, Miltenyi Biotec), 10 µl of 10 µg/ml Cytochalasin D (CytoD, Sigma), or were untreated were then added to the bead-mAb complexes. Controls consisted of gp120(ZM53)-coated beads without bound mAb or incubated with mAb 1418, specific for B19 parvovirus. FIG. 11B shows the titration of phagocytic activity in rabbit immune sera using beads coated with V1V2(ZM109)-1FD6. Data shown are the means from values from individual rabbits in each group+/− standard error of the mean. FIG. 11C shows ADCP scores for rabbit immune sera diluted 1:20 when using beads coated with V1V2(YU2)-1FD6. Data shown are the means from individual rabbits in each group+/−standard error of the mean. FIG. 11D shows the immunization regimen used for each of the six rabbit groups studied and the mean OD determined from ELISA experiments with a 1:100 dilution of serum from each individual rabbit in each group tested for reactivity with V1V2ZM109-1FD6.

FIG. 12A shows the immunization regimen and schedule. FIG. 12B shows the animal groups and immunogens used for each group, as well as the icons used to represent the immunogens. FIG. 12C is a detailed list for the animal groups and immunogens used. As shown in FIGS. 12B and 12C, the 4 macaque groups were identified as Experiment (Expt) Groups 1a, 1b, 2b, and 3b.

Figure 17A:
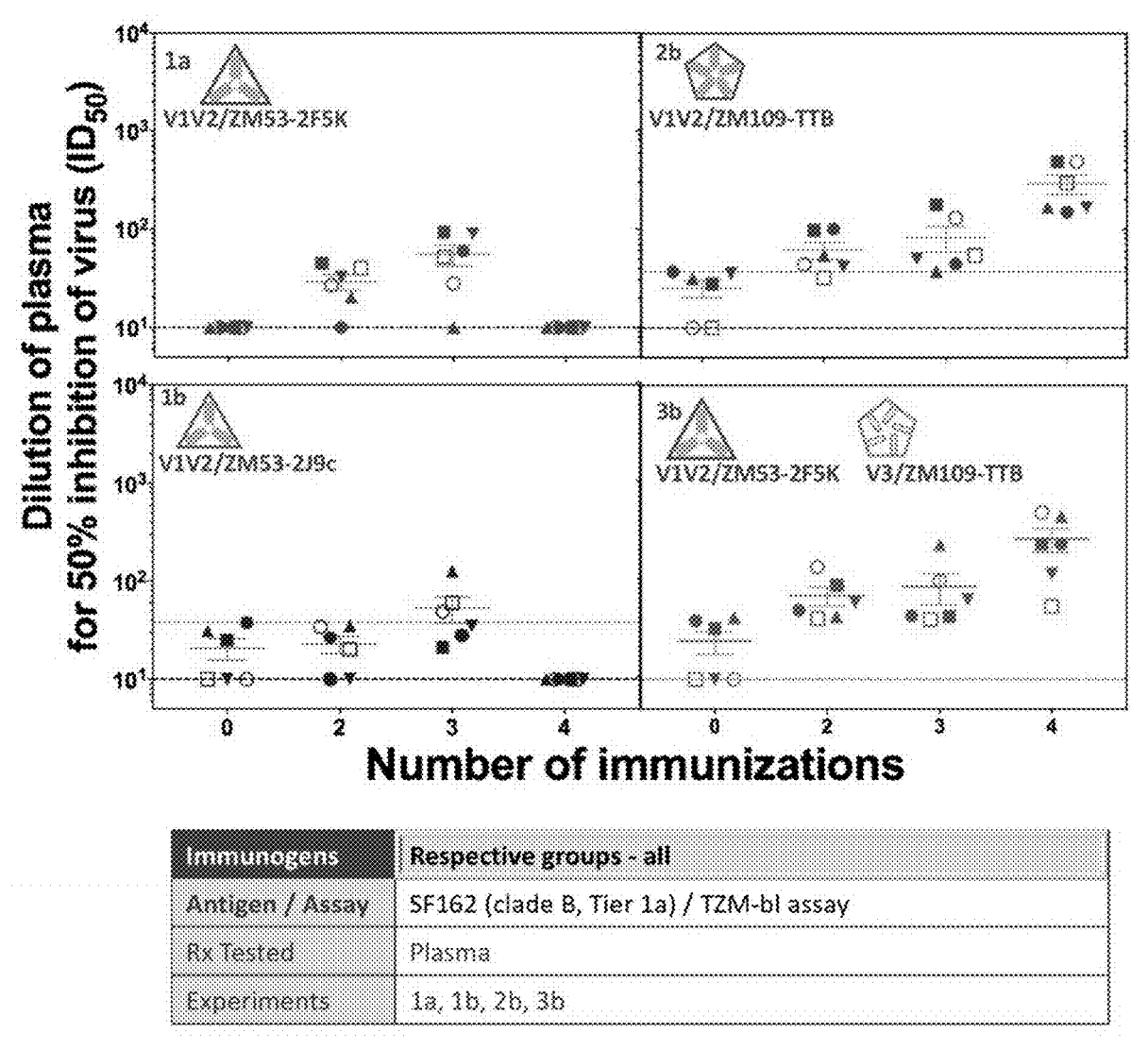

FIGS. 17A-17B shows results of neutralization of Tier 1A viruses by macaque plasma against SF162 (FIG. 17A) and MW965 (FIG. 17B). FIGS. 17A and 17B each show results with respect to macaque plasma from Experiment Group 1a (left upper graph panels), Experiment Group 1b (left lower graph panels), Experiment Group 2b (right upper graph panels), and Experiment Group 3b (right lower graph panels).

Figure 18A:
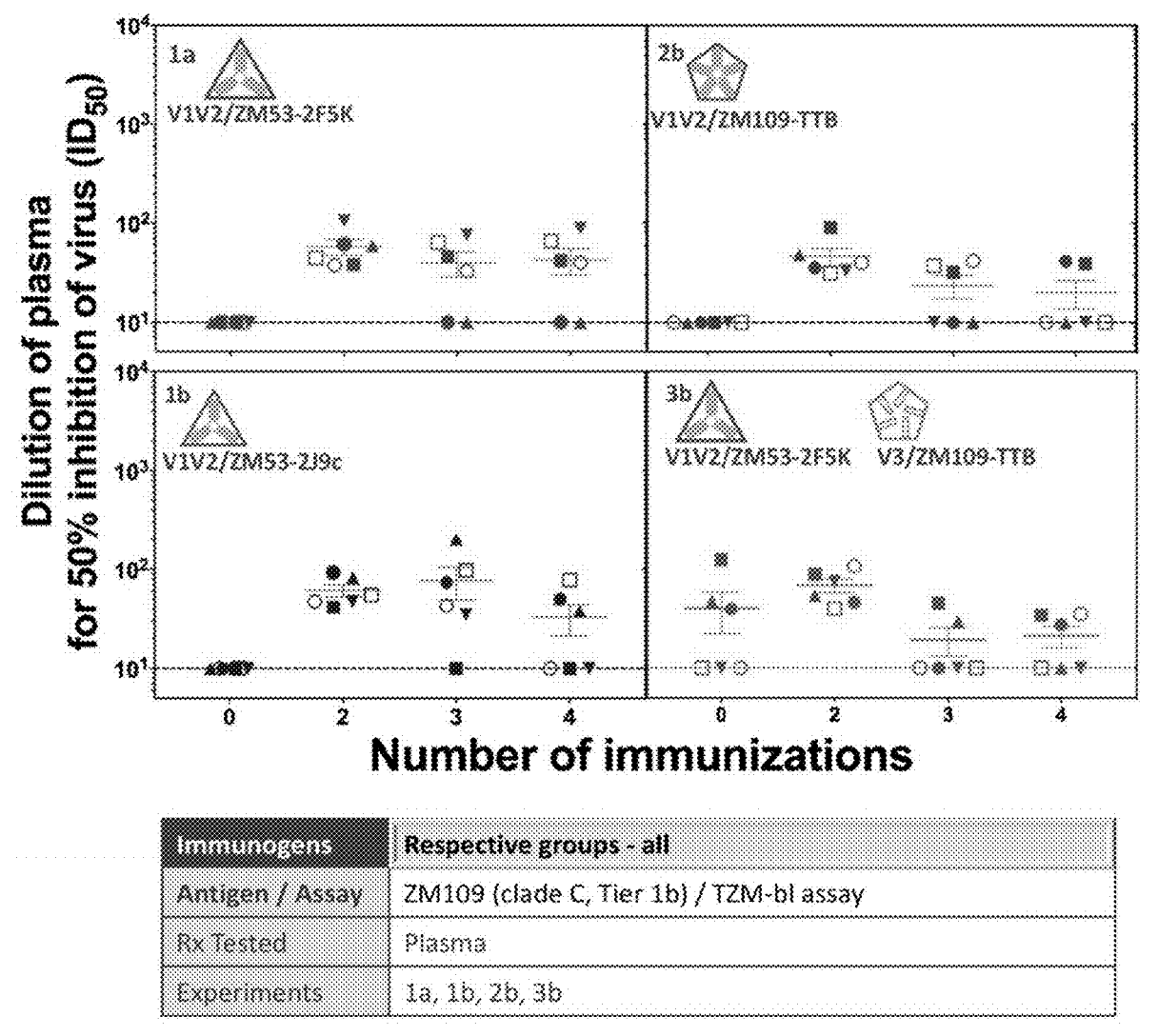

FIGS. 18A-18B show results of neutralization of Tier 1B viruses by macaque plasma against ZM109 (FIG. 18A) and ZM197 (FIG. 18B). FIGS. 18A and 18B each show results with respect to macaque plasma from Experiment Group 1a (left upper graph panels), Experiment Group 1b (left lower graph panels), Experiment Group 2b (right upper graph panels), and Experiment Group 3b (right lower graph panels).

DETAILED DESCRIPTION OF THE INVENTION

Figures 1A, 1B, 1C, 1D:
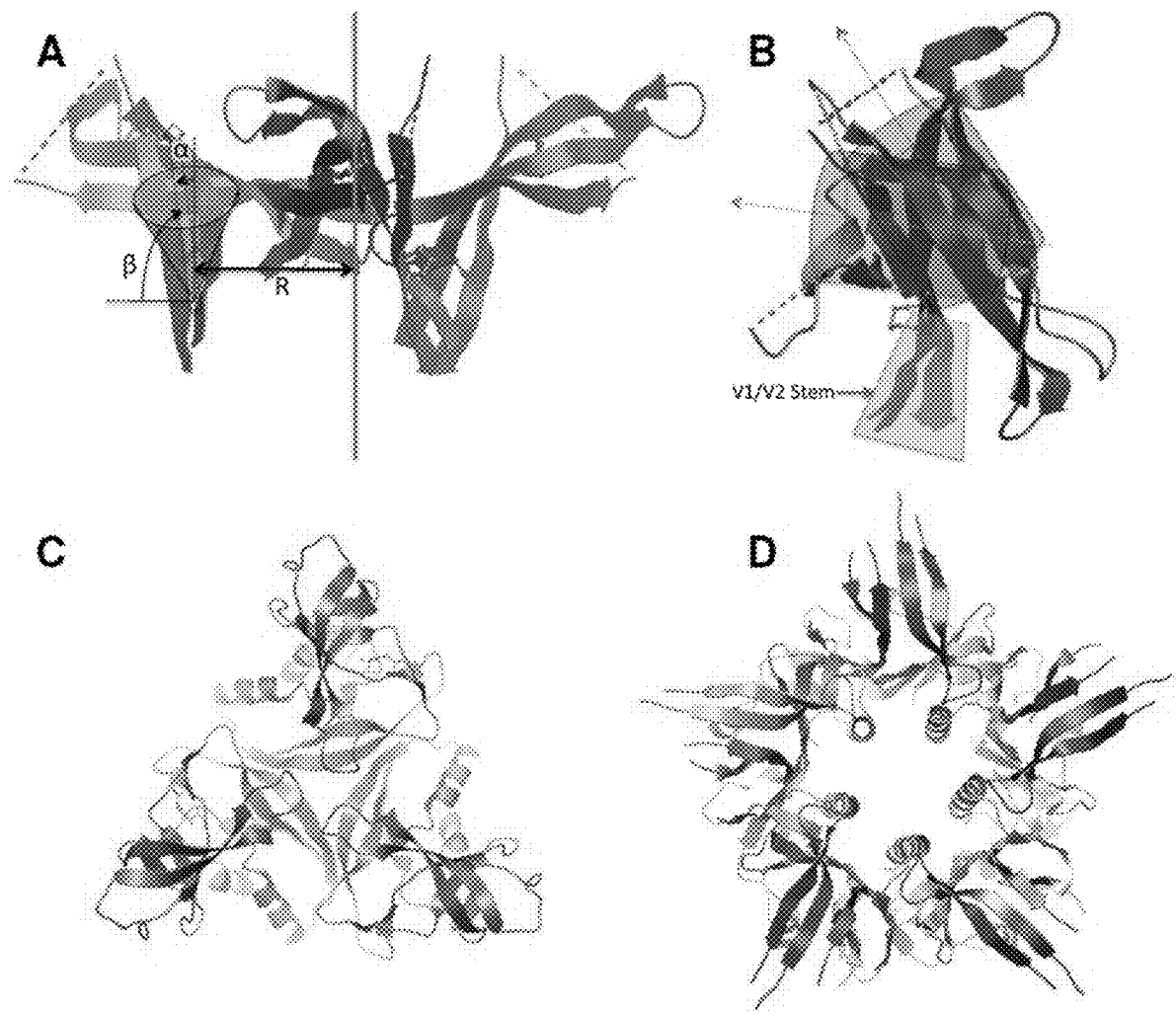
FIGS. 1A-1D show the design of V1V2 immunogens.

A first aspect of the present invention is directed to an isolated immunogenic polypeptide. The isolated immunogenic polypeptide includes a scaffold polypeptide having a hairpin loop. The hairpin loop is modified to include one or more epitopes heterologous to the scaffold polypeptide and from an amino acid loop linked by a disulfide bond. The scaffold polypeptide directs self-assembly with two other of the scaffold polypeptides to form a trimeric structure, where the trimeric structure constrains the one or more epitopes to a conformation that is (i) substantially similar to one or more native pathogen epitopes in trimeric conformation and (ii) capable of binding an antibody reactive to the one or more native pathogen epitopes in trimeric conformation.

Also contemplated are other embodiments where the scaffold polypeptide directs self-assembly with two other of the scaffold polypeptides to form a trimeric structure, where the trimeric structure constrains the one or more epitopes to a conformation that is (i) substantially similar to one or more native pathogen epitopes and (ii) capable of binding an antibody reactive to the one or more native pathogen epitopes.

The phrase "one or more epitopes" as used throughout the present application may include, for example, one or more of each epitope described herein or combinations thereof.

In certain embodiments, the isolated immunogenic polypeptide includes a scaffold polypeptide having a hairpin loop. The hairpin loop is modified to include an epitope heterologous to the scaffold polypeptide and from an amino acid loop linked by a disulfide bond. The scaffold polypeptide directs self-assembly with two other of the scaffold polypeptides to form a trimeric structure, where the trimeric structure constrains the epitope to a conformation that is (i) substantially similar to a native pathogen epitope in trimeric conformation and (ii) capable of binding an antibody reactive to the native pathogen epitope in trimeric conformation.

The term epitope as described herein is the portion of an antigen to which a monoclonal antibody specifically binds. Thus, the term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. More specifically, "epitope" as used herein refers to a portion of the corresponding polypeptide having antigenic or immunogenic activity in an animal, preferably in a mammal, and most preferably in a mouse or a human. An epitope having immunogenic activity is a portion of a polypeptide that elicits an antibody response in an animal. An epitope having antigenic activity is a portion of a polypeptide to which an antibody immunospecifically binds as determined by any method well known in the art, for example, by immunoassays. Antigenic epitopes need not necessarily be immunogenic. Such epitopes can be linear in nature or discontinuous. Thus, as used herein, the epitope may refer to a discontinuous epitope formed by a spatial relationship between amino acids of an antigen other than an unbroken series of amino acids. Epitopes of the immunogenic polypeptides described herein also include functionally equivalent variants of an antigenic or immunogenic epitope which mimics the antigenic and/or immunogenic properties of the epitope.

Epitope(s) as described in certain embodiments herein are those of an amino acid loop linked by a disulfide bond. Immunogenic polypeptides described herein may include the entire amino acid loop linked by a disulfide bond (i.e., inclusive of the disulfide bond) which includes an epitope as described herein, or any fragment thereof which includes an epitope as described herein. Such disulfide bonded loops have been discovered to be presented in a conformationally correct orientation within the scaffold polypeptides described herein for binding to antibodies directed against a pathogen. The epitope(s) may also be from an amino acid loop linked by more than one (e.g., 2, 3, 4, 5, etc.) disulfide bonds. Further, immunogenic peptides described herein may include one or more epitopes (e.g., 2, 3, 4, 5, 6, 7, 8, 9, 10, 11, 12, 13, 14, 15, 26, 27, 28, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, etc).

The epitope(s) as described herein may be a continuous or discontinuous epitope (or mimic thereof) derived from bacteria or virus.

The virus can be any type of virus. Exemplary viruses include, without limitations, Calicivirus, Chikungunya virus, Cytomegalovirus, Dengue virus, Eastern Equine Encephalitis virus, Ebola virus, Epstein-Barr virus, Hantaan virus, Hepatitis A virus, Hepatitis B virus, Hepatitis C virus, Hepatitis D virus, Hepatitis E virus, Herpes simplex virus, Human Immunodeficiency virus (HIV-1), Simian immunodeficiency virus (SIV), Human Papillomavirus, Influenza virus, Japanese encephalitis virus, Junin virus, Lassa virus, Marburg virus, Measles virus, Metapneumovirus, Nipah virus, Newcastle disease virus, Norwalk virus, Parainfluenza virus, Poliovirus, Rabies virus, Respiratory Syncytial virus, Rift Valley Fever virus, Rotavirus, Rubella virus, Sendai virus, Severe Acute Respiratory Syndrome (SARS Co-V), Tick-borne Encephalitis virus, Varicella zoster virus, Venezuelan Equine Encephalitis virus, Yellow Fever virus, Western Equine Encephalitis virus, and West Nile virus. In one embodiment the pathogen is HIV. In one embodiment the epitope is derived from or mimics an epitope of an HIV-derived polypeptide or protein.

The bacteria can be any type of bacterium. Exemplary bacteria according to the embodiments the present invention may include, without limitation, *Bacillus anthracis*, *Bordetella pertussis* B, *Borrelia burgdorferi*, *Chlamydia trachomatis*, *Clostridium difficile*, *Clostridium tetani*, *Candida albicans*, *Corynebacterium diphtherias*, *Cryptococcus neoformans*, *Entamoeba histolytica*, *Escherichia coli*, *Francisella tularensis*, *Haemophilus influenzae* (nontypeable), *Helicobacter pylori*, *Histoplasma capsulatum*, *Moraxella catarrhalis*, *Mycobacterium leprae*, *Mycobacterium tuberculosis*, *Neisseria gonorrheae*, *Neisseria meningitides*, *Pseudomonas aeruginosa*, *Staphylococcus aureus*, Methicillin-resistant *Staphylococcus aureus*, *Streptococcus agalactiae*, *Streptococcus pneumoniae*, *Streptococcus pyogenes*, and *Yersinia pestis*.

In one embodiment, the one or more epitopes described herein are derived from an envelope (or Env) polypeptide. The envelope polypeptide may be one from, for example, any lentivirus. For instance, the envelope polypeptide may be from human HIV-1 or HIV-2. The envelope polypeptide may also be from, for example, any of Groups M, N, O or P and from any clade or circulating recombinant form (CRF) of HIV-1. For example, the envelope polypeptide may be from HIV-1, Group M, and any of clades A-K. In one embodiment, the envelope polypeptide may be from any of clades B, C, or CRF_01AE. In other embodiments, the envelope polypeptide may be from a primate lentivirus including, for example, Simian AIDS retrovirus (SIV) such as, SIV (AGM155), SIV (AGM266 isolate), SIV (AGM3 isolate), SIV (AGM385 isolate), SIV (F236/SMH4 isolate, Sooty Mangabey), SIV (TyO-1 isolate) and SIVagm; Simian immunodeficiency virus, such as, SIV (1A11 isolate), SIV (isolate African mandril), SIV (AGM/clone Gri-1), SIV (vervet), SIV (Tantalus), SIV (STM isolate), SIV (17E-C1), SIV Qu, SIVdeb, SIVmac, SIVMND, SIVmon, SIVsm; and Simian-Human immunodeficiency virus (SHIV).

As described herein, the one or more epitopes (or mimic(s) thereof) is/are capable of binding an antibody reactive to one or more native pathogen epitopes. In one embodiment, the native pathogen epitope(s) is/are in native trimeric conformation. Exemplary pathogens are described above. In one embodiment, the antibody is reactive to the V1 and/or V2 region of the HIV-1 surface envelope glycoprotein gp120. In one embodiment, the antibody is a V2-specific antibody. In one embodiment the antibody mediates antibody-dependent cellular phagocytosis. In another embodiment, the epitope is capable of binding to a neutralizing monoclonal antibody. Examples include, without limitation, those selected from the group consisting of HIV PG9 Mab, HIV PG16 Mab, 697-D, 830A and combinations thereof.

As described herein, the epitope(s) may include any V2q, V2p, or V2i antibody epitope(s) or overlapping region thereof. V2p antibodies target a linear epitope represented by a peptide from the C strand of V2 which assumes a helical structure when bound to V2p antibodies. V2i antibodies target a highly conformational epitope that includes the integrin binding site at residues 179-181. V2q antibodies preferentially target a V1V2 peptidoglycan which is part of the structure created by the quaternary interaction of the three V1V2 domains in the Env trimer.

In one embodiment, the one or more epitopes is/are from (or mimic(s)) the V1V2 region of the surface envelope glycoprotein gp120 of the envelope polypeptide of an HIV virus (e.g., HIV-1), as described herein. In one embodiment, the one or more epitopes comprises a V1V2 fragment of HIV-1 surface envelope glycoprotein gp120 where the trimeric structure constrains the V1V2 fragment to a conformation substantially similar to that of an HIV-1 virion's native surface envelope glycoprotein gp120. The trimeric conformation of an HIV-1 virion's native surface envelope glycoprotein gp120 may be characterized as having a unique five-stranded β-barrel structure with strands A, B, C, C', and D (see FIG. 1). In the trimer context, the V1V2 regions in the trimer join together at the apex center to form a top layer of the Env complex.

The V1V2 region of gp120 is the most diverse in both sequence and length. V1V2, including residues 126 to 196 in the HXB2 numbering scheme (Ratner et al., "Complete Nucleotide Sequences of Functional Clones of the AIDS Virus," *AIDS Res Hum Retroviruses* 3:57-69 (1987), which is hereby incorporated by reference in its entirety), usually has two nested disulfide bonds; the V1 disulfide bond (between cysteine residues 131 and 157) is located within the V2 disulfide bond (between residues 126 and 196) (Leonard et al., "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells," *J Biol Chem* 265:10373-10382 (1990), which is hereby incorporated by reference in its entirety). The average length of V1V2 is about 80 amino acids. In one embodiment, the V1V2 region has the following consensus sequence: CVTLNCTDV--NATN--NTTNN--------EEIKNC SFNITTEIRD KKKKVYALFY KLDVVPIDD---NNS----Y RLINC (SEQ ID NO: 13) as retrieved from the HIV LANL database (www.hiv.lanl.gov, which is hereby incorporated by reference in its entirety).

The one or more epitopes according to certain embodiments comprises an amino acid sequence at least 40% identical to the amino acid sequence of SEQ ID NO: 1 (CVTLNCTSPAAHNESETRVKHCSFNITTD-VKDRKQKVNATFYDLDIVPLSSSDNSSN SSLYR-LISC); SEQ ID NO:2 (CVTLNCSKLNNATDGEM-KNCSFNATTELRDKKKQVYALFYKLDIVPLDGRNN-SSE YRLINC); SEQ ID NO: 3 (CVTLNCTNVKGNESDT-SEVMKNC SFKATTELKDKKHKVHALFYKLDV-VPLNGNSS SSGEYRLINC); SEQ ID NO:4 (CVTLRCT-NATINGSLTEEVKNCSFNITTELRDKKQKAYALFYRP-DVVPLNKNSPSGN SSEYILINC); or SEQ ID NO:5 (CVTLHCTNANLTKANLTNVNNRTNVSNIIGNIT-DEVRNCSFNMTTELRDKKQKVHA LFYKL-DIVPIEDNNDSSEYRLINC) (ZM109; ZM53; 1086; CAP45; A244, respectively) and comprises amino acid residue(s) between (and including) positions 126 and 196 according to the numbering convention of strain B.FR.HXB2 retrieved from the HIV LANL database (www.hiv.lanl.gov, which is hereby incorporated by reference in its entirety). The one or more epitopes according to certain embodiments comprises amino acid residue(s) between (and including) positions 126 and 196 according to the numbering convention of strain B.FR.HXB2 retrieved from the HIV LANL database (www.hiv.lanl.gov, which is hereby incorporated by reference in its entirety). The one or more epitopes according to certain embodiments described herein comprises an amino acid sequence having at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with the amino acid sequence of amino acid residue(s) between (and including) positions 126 and 196 according to the numbering convention of strain B.FR.HXB2 retrieved from the HIV LANL database (www.hiv.lanl.gov, which is hereby incorporated by reference in its entirety).

The one or more epitopes according to certain embodiments described herein comprises the amino acid sequence of SEQ ID NO: 1; SEQ ID NO: 2; SEQ ID NO: 3; SEQ ID NO: 4; or SEQ ID NO: 5 (ZM109; ZM53; 1086; CAP45; A244, respectively), or an immunogenic fragment thereof. The one or more epitopes according to certain embodiments described herein comprises an amino acid sequence having at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with SEQ ID NO: 1; SEQ ID NO:2; SEQ ID NO: 3; SEQ ID NO:4; or SEQ ID NO:5.

The one or more epitopes according to certain embodiments described herein may include one or more of the amino acid sequence of SEQ ID NO:18 (CVTLNCTNAN-VTNVKNITNVPNIIGNITDEVRNCSFNMTTELRDK-KQKVHALFYKL DIVPIEDNTSSSEYRLINC); SEQ ID NO:19 (CVTLNCIDLRNATNATSNSNTTNTTSSSGG-LMMEQGEIKNCSFNITTSIRDKVQKEY ALFYKL-DIVPIDNPKNSTNYRLISC); SEQ ID NO:20 (CVTLNCT-DLRNATNTTSSSWETMEKGEIKNCSFNITTSIRDK-VQKEYALFYNLDVVP IDNASYRLISC); SEQ ID NO:21 (CSFNMTTELRDKKQKVHALFYKLDIVPIEDNT-SSSEYRLINC) (Strains 92TH023, Case A2, YU2, 92TH023 (cV2 peptide), respectively, as set forth in Table 5, infra); or an immunogenic fragment thereof. The one or more epitopes according to certain embodiments described herein comprise(s) an amino acid sequence having at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with SEQ ID NO:18; SEQ ID NO:19; SEQ ID NO:20; SEQ ID NO:21; or an immunogenic fragment thereof.

In one embodiment, the one or more epitopes is from (or mimics) the V3 region of the surface envelope glycoprotein gp120 of the envelope polypeptide of an HIV virus (e.g., HIV-1), as described herein. In one embodiment, the one or more epitopes from the V3 region comprises the amino acid sequence CIRPGNNTRKSIRLGPGQTFYATGDVIGDIR-KAYC (SEQ ID NO: 26) or an immunogenic fragment thereof. In one embodiment, the one or more epitopes possesses at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with that of SEQ ID NO: 26.

For all polypeptides described herein, sequence variations may be present from those sequences described herein if they do not adversely affect or abolish the ability of polypeptides described herein to function in accordance with the present invention to, e.g., bind an antibody reactive to a pathogen (in the case of an epitope), serve as a suitable scaffold to present an epitope in a desired conformation (in the case of a scaffold polypeptide), and/or produce an immunogenic response (in the case of the immunogenic polypeptides), as described herein. Such sequence variations may include insertions, deletions, or substitutions. For example, contemplated for use in accordance with embodiments described herein are sequences having at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with sequences described herein.

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. As noted in the examples that follow, a trimeric graft-scaffold construct was engineered that presents an epitope of an amino acid loop linked by a disulfide bond (e.g., V1V2 domain) in a manner mimicking conformation of the native epitope. In the case of HIV, the conformation is that of the V1V2 region at the apex of the viral envelop spike. This scaffolded presentation of such an epitope reproduces effects of quaternary interactions on the native epitope conformation and native epitope exposure.

The modified and unmodified scaffold polypeptides according to embodiments described herein possess the ability to self-direct assembly with other such scaffold polypeptides to form, for example, homo-trimeric structures or homo-pentameric structures (as described infra). Such structures may be symmetrical. In certain embodiments described herein, the structure of scaffold polypeptide apart from (or different from) that of the epitope directs self-assembly with other such polypeptides.

The unmodified scaffold polypeptides according to embodiments described herein possess hairpin loop structures that can accommodate modification to include one or more epitopes heterologous to the scaffold polypeptides described herein. Also contemplated are scaffold polypeptides having a native amino acid loop structure (or native loop) that is not necessarily a hairpin loop, which may be modified to include one or more epitopes heterologous to the scaffold polypeptides described herein. The native loop may be modified to include one or more epitopes heterologous to the scaffold polypeptide and from an amino acid loop linked by a disulfide bond. As discussed below, the "native loop" is contemplated to encompass, for example, a naturally occurring amino acid loop formed or linked by a disulfide bond, a hairpin loop, and any other amino acid loop structure of the scaffold polypeptides described herein.

In one embodiment, the scaffold polypeptide constrains the center mass of the amino acid residues immediately preceding the disulfide bond of the hairpin loop at about 10 to 14 Angstroms from the trimer axis, and tilts the vector of the hairpin loop direction about 10 to 30 degrees both outwards and clockwise around the axis.

In another embodiment, the scaffold polypeptide constrains the center mass of the amino acid residues immediately preceding the disulfide bond of the hairpin loop at about 12 Angstroms from the trimer axis, and tilts the vector of the hairpin loop direction about 20 degrees both outwards and clockwise around the axis.

In one embodiment, the scaffold polypeptide is a modified GlnK1 from *Methanococcus jannaschii*. GlnK1 (UniProtKB Accession No: Q60381 and GenBank Accession No. 2J9C_C, each of which is hereby incorporated by reference in its entirety) is a signalling protein that plays a role in ammonia uptake through the cell membrane (See Yildiz et al., "Structure of Glnk1 with Bound Effectors Indicates Regulatory Mechanism For Ammonia Uptake," *EMBO J.* 26:589 (2007), which is hereby incorporated by reference in its entirety). The crystal structure of GlnK1 and the related sequence information is found at Protein Data Bank (PDB) ID 2J9C (Yildiz et al., 10.2210/pdb4k6l/pdb, Released Jan. 16, 2007, which is hereby incorporated by reference in its entirety). The amino acid sequence for unmodified GlnK1 (referred to as 2J9C) is as follows:

(SEQ ID NO: 6)
GSMKKVEAHRPEKLEIVKKALSDAGYVGMTVSEVKGRGVQGGIVERY<u>R</u>
<u>GREY</u>IVDLIPKVKIELVVKEEDVDNVIDHCENARTGNPGDGMFVIPVERV
VRVRTKEEGKEALLEH

Those portions retained in the immunogenic polypeptide of SEQ ID NO: 9, described below, are presented in bold; the amino acids in the hairpin loop replaced with an epitope described herein are shown in underline. Although two amino acids were replaced in the hairpin loop, any number of amino acids in the loop region may be replaced. An insertion of epitope(s) described herein may also be made without replacing or deleting amino acids from the hairpin loop region.

Also contemplated for use in accordance with embodiments described herein are variants, isoforms, and homologs of GlnK1 from *Methanococcus jannaschii*. Such molecules may possess at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with that of GlnK1 from *Methanococcus jannaschii*.

In one embodiment, the scaffold polypeptide is a modified chromo domain of a protein. Chromo domains are protein structural domains of about 40-50 amino acid residues commonly found in proteins associated with the remodeling and manipulation of chromatin. In one embodiment, the chromo domain is that of Mortality factor 4-like protein 1 ("MRG15").

Accordingly, in one embodiment, the scaffold polypeptide is a modified human MRG15. Human MRG15 (UniProtKB Accession No: Q9UBU8 and GenBank Accession No. NP_996670, each of which is hereby incorporated by reference in its entirety) is a transcription factor that plays a vital role in embryonic development, cell proliferation and cellular senescence. (See Zhang et al., "Structure of Human MRG15 Chromo Domain and Its Binding to Lys36-Methylated Histone H3," *Nucleic Acids Res.* 34:6621-6628 (2006), which is hereby incorporated by reference in its entirety). It comprises a chromo domain in the N-terminal part that has been shown to participate in chromatin remodeling and transcription regulation. The crystal structure of the chromo domain of human MRG15 and the related sequence information is found at Protein Data Bank (PDB) ID 2F5K (Zhang et al., DOI: 10.2210/pdb2f5k/pdb, Released Nov. 14, 2006, which is hereby incorporated by reference in its entirety). The amino acid sequence for unmodified human MRG15 chromo domain (referred to as 2F5K) is as follows:

(SEQ ID NO: 7)
PKPKFQEGERVLCFHGPLLYEAKCVKVAI<u>KDKQVK</u>YFIHYSGWNKNWD
EWVPESRVLKYVDTNLQKQRELQKANQEQYAEGK

Those portions retained in the immunogenic polypeptide of SEQ ID NO: 8, described below, are presented in bold; the amino acids in the hairpin loop replaced with an epitope described herein are shown in underline. Although six amino acids were replaced in the hairpin loop, any number of amino acids in the loop region may be replaced. An insertion of an epitope described herein may also be made without replacing or deleting amino acids from the hairpin loop region.

Also contemplated for use in accordance with embodiments described herein are variants, isoforms, and homologs of human MRG15. Such molecules (or the chromo domain(s) thereof) may possess at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with that of human MRG15 (or the chromo domain thereof).

Functions of the immunogenic polypeptides described herein include, but are not limited to, the ability to induce antibody-mediated cytotoxic and phagocytic effector function in order to destroy targeted cells. Fc-mediated non-neutralizing Ab functions play a role in reducing and preventing infection with SIV, SHIV and HIV, and in controlling virus replication in vivo (Corey et al., "Immune Correlates of Vaccine Protection Against HIV-1 Acquisition," *Sci. Transl. Med.* 7:310rv317 (2015); Li et al., "Fc Gamma IIC Polymorphisms Associate With HIV-1 Vaccine Protection in RV144 Trial," *J. Clin. Invest.* 124:3879-3890 (2014); Pollara et al., "HIV-1 Vaccine-Induced C1 and V2 Env-Specific Antibodies Synergize For Increased Antiviral Activities," *J. Virol.* 88:7715-7726 (2014); Chung et al., "Polyfunctional Fc-Effector Profiles Mediated by IgG Subclass Selection Distinguish RV144 and VAX003 Vaccines," *Sci. Transl. Med.* 6:228ra238 (2014); Haynes et al., "Immune Correlates Analysis of the ALVAC-AIDSVAX HIV-1 Vaccine Efficacy Trial," *N. Engl. J. Med.* 366:1275-1286 (2012); Bonsignori et al., "Antibody-Dependent Cellular Cytotoxicity-Mediating Antibodies From an HIV-1 Vaccine Efficacy Trial Target Multiple Epitopes and Preferentially Use the VH1 Gene Family," *J. Virol.* 86:11521-11532 (2012); Montefiori et al., "Magnitude and Breadth of the Neutralizing Antibody Response in the RV144 and Vax003 HIV-1 Vaccine Efficacy Trials," *J. Infect. Dis.* 206:431-441 (2012); Liao et al., "Vaccine Induction of Antibodies Against a Structurally Heterogeneous Site of Immune Pressure Within HIV-1 Envelope Protein Variable Regions 1 and 2," *Immunity* 38:1-11 (2013); Pollara et al., "Epitope Specificity of Human Immunodeficiency virus-1 Antibody Dependent Cellular Cytotoxicity [ADCC] Responses," *Curr. HIV Res.* 11:378-387 (2013); Chung et al., "Dissecting Polyclonal Vaccine-Induced Humoral Immunity Against HIV Using Systems Serology," *Cell* 163: 988-998 (2015), each of which is hereby incorporated by reference in its entirety). As early as 2004, vaccine-elicited Abs were shown to mediate ADCC which correlated with reduced acute viremia in rhesus macaques challenged with SIVmac251 (Patterson et al., "Protection Against Mucosal Simian Immunodeficiency Virus SIV(mac251) Challenge by Using Replicating Adenovirus-SIV Multigene Vaccine Priming and Subunit Boosting," *J. Virol.* 78:2212-2221 (2004); Gomez-Roman et al., "Vaccine-Elicited Antibodies Mediate Antibody-Dependent Cellular Cytotoxicity Correlated With Significantly Reduced Acute Viremia in Rhesus Macaques Challenged With SIVmac251," *J. Immunol.* 174: 2185-2189 (2005), each of which is hereby incorporated by reference in its entirety). Subsequently, myriad studies have shown that non-neutralizing Abs mediating ADCC and other Fc-dependent activities can prevent or contribute to control of SIV (Forthal & Moog, "Fc Receptor-Mediated Antiviral Antibodies," *Curr. Opin. HIV AIDS* 4:388393 (2009); Alpert et al., "ADCC Develops Over Time During Persistent Infection With Live-Attenuated SIV and is Associated With Complete Protection Against SIV(mac)251 Challenge," *PLoS Pathog.* 8:e1002890 (2012); Fouts et al., "Balance of Cellular and Humoral Immunity Determines the Level of Protection by HIV Vaccines in Rhesus Macaque Models of HIV Infection," *Proc. Nat'l. Acad. Sci. U.S.A.* 112:E992-999 (2015), each of which is hereby incorporated by reference in its entirety) and SHIV (Fouts et al., "Balance of Cellular and Humoral Immunity Determines the Level of Protection by HIV Vaccines in Rhesus Macaque Models of HIV Infection," *Proc. Nat'l. Acad. Sci. U.S.A.* 112:E992-999 (2015); Barouch et al., "Protective Efficacy of a Global HIV-1 Mosaic Vaccine Against Heterologous SHIV Challenges in Rhesus Monkeys," *Cell* 155:531539 (2013); Vargas-Inchaustegui & Robert-Guroff, "Fc Receptor-Mediated Immune Responses: New Tools but Increased Complexity in HIV Prevention," *Curr. HIV Res.* 11:407-420 (2013); Santra et al., "Human Non-Neutralizing HIV-1 Envelope Monoclonal Antibodies Limit the Number of Founder *Viruses* During SHIV Mucosal Infection in Rhesus Macaques," *PLoS Pathog.* 11:e1005042 (2015), each of which is hereby incorporated by reference in its entirety). Significantly, Abs that mediate ADCC have been found in human breast milk and correlate with reduced risk of transmission from mother to infant (Mabuka et al., "HIV-Specific Antibodies Capable of ADCC Are Common in Breastmilk and Are Associated With Reduced Risk of Transmission in Women With High Viral Loads," *PLoS Pathog.* 8:e1002739 (2012), which is hereby incorporated by reference in its entirety).

Several streams of data from the RV144 clinical vaccine trial also suggest that reduced rates of HIV infection are associated with Abs that mediate ADCC and ADCP, but notably, no correlation with the presence of serum neutralizing Abs was identified in RV144 vaccinees (Li et al., "Fc Gamma IIC Polymorphisms Associate With HIV-1 Vaccine Protection in RV144 Trial," *J. Clin. Invest.* 124:3879-3890 (2014); Pollara et al., "HIV-1 Vaccine-Induced C1 and V2 Env-Specific Antibodies Synergize For Increased Antiviral Activities," *J Virol.* 88:7715-7726 (2014); Chung et al., "Polyfunctional Fc-Effector Profiles Mediated by IgG Subclass Selection Distinguish RV144 and VAX003 Vaccines," *Sci. Transl. Med.* 6:228ra238 (2014); Haynes et al., "Immune Correlates Analysis of the ALVAC-AIDSVAX HIV-1 Vaccine Efficacy Trial," *N. Engl. J. Med.* 366:1275-1286 (2012); Bonsignori et al., "Antibody-Dependent Cellular Cytotoxicity-Mediating Antibodies From an HIV-1 Vaccine Efficacy Trial Target Multiple Epitopes and Preferentially Use the VH1 Gene Family," *J. Virol.* 86:11521-11532 (2012); Montefiori et al., "Magnitude and Breadth of the Neutralizing Antibody Response in the RV144 and Vax003 HIV-1 Vaccine Efficacy Trials," *J. Infect. Dis.* 206:431-441 (2012); Liao et al., "Vaccine Induction of Antibodies Against a Structurally Heterogeneous Site of Immune Pressure Within HIV-1 Envelope Protein Variable Regions 1 and 2," *Immunity* 38:1-11 (2013); Pollara et al., "Epitope Specificity of Human Immunodeficiency virus-1

Antibody Dependent Cellular Cytotoxicity [ADCC] Responses," *Curr. HIV Res.* 11:378-387 (2013); Chung et al., "Dissecting Polyclonal Vaccine-Induced Humoral Immunity against HIV Using Systems Serology," *Cell* 163: 988-998 (2015), each of which is hereby incorporated by reference in its entirety). The protective role for Fc-mediated Ab function is further supported by the finding that specific alleles of FcγRIIc (which carries the extracellular sequence of FcγRIIa, a critical component of ADCP) were associated with RV144 vaccine efficacy (Li et al., "Fc Gamma IIC Polymorphisms Associate With HIV-1 Vaccine Protection in RV144 Trial," *J. Clin. Invest.* 124:3879-3890 (2014), which is hereby incorporated by reference in its entirety). Moreover, the V2-specific IgG Abs levels, which were an independent correlate of reduced infection rate in RV144 (Haynes et al., "Immune Correlates Analysis of the ALVAC-AIDSVAX HIV-1 Vaccine Efficacy Trial," *N. Engl. J. Med.* 366:1275-1286 (2012); Zolla-Pazner et al., "Analysis of V2 Antibody Responses Induced in Vaccinees in the ALVAC/AIDSVAX HIV-1 Vaccine Efficacy Trial," *PLos One* 8:e53629 (2013); Gottardo et al., "Plasma IgG to Linear Epitopes in the V2 and V3 Regions of HIV-1 gp120 Correlate With a Reduced Risk of Infection in the RV144 Vaccine Efficacy Trial," *PLoS One* 8:e75665 (2013); Zolla-Pazner et al., "Vaccine-Induced IgG Antibodies to V1V2 Regions of Multiple HIV-1 Subtypes Correlate With Decreased Risk of HIV-1 Infection," *Plos One* 9:e87572 (2014); Yates et al., "Vaccine-Induced Env V1-V2 IgG3 Correlates With Lower HIV-1 Infection Risk and Declines Soon After Vaccination," *Sci. Transl. Med.* 6:228ra239 (2014), each of which is hereby incorporated by reference in its entirety), appear to have played a role in the Fc-mediated vaccine-induced anti-viral activities in that V2 Abs contributed to ADCC responses (Bonsignori et al., "Antibody-Dependent Cellular Cytotoxicity-Mediating Antibodies From an HIV-1 Vaccine Efficacy Trial Target Multiple Epitopes and Preferentially Use the VH1 Gene Family," *J. Virol.* 86:11521-11532 (2012); Liao et al., "Vaccine Induction of Antibodies Against a Structurally Heterogeneous Site of Immune Pressure Within HIV-1 Envelope Protein Variable Regions 1 and 2," *Immunity* 38:1-11 (2013), each of which is hereby incorporated by reference in its entirety) and were found to synergize with C1-specific Abs which were also induced by the vaccine (Pollara et al., "HIV-1 Vaccine-Induced C1 and V2 Env-Specific Antibodies Synergize for Increased Antiviral Activities," *J. Virol.* 88:7715-7726 (2014), which is hereby incorporated by reference in its entirety). V2-specific Abs have also been identified as correlates of protection after immunization and challenge with SIV and SHIV (Pegu et al., "Antibodies With High Avidity to the gp120 Envelope Protein in Protection From Simian Immunodeficiency Virus SIV(mac251) Acquisition in an Immunization Regimen That Mimics the RV-144 Thai Trial," *J. Virol.* 87:1708-1719 (2013); Vaccari et al., "Adjuvant-Dependent Innate and Adaptive Immune Signatures of Risk of SIV Acquisition," *Nat. Med.* 22:762-770 (2016); Barouch et al., "Vaccine Protection Against Acquisition of Neutralization-Resistant SIV Challenges in Rhesus Monkeys," *Nature* 482:89-93 (2012), each of which is hereby incorporated by reference in its entirety).

As described above, the Fc region of an antibody interacts with a number of Fc receptors and ligands, imparting an array of important functional capabilities referred to as effector functions. The cell-mediated reaction wherein non-specific cytotoxic cells that express Fcγ receptors recognize bound antibody on a target cell and subsequently cause lysis of the target cell is referred to as antibody dependent cell-mediated cytotoxicity (ADCC). The cell-mediated reaction wherein nonspecific cytotoxic cells that express Fcγ receptors recognize bound antibody on a target cell and subsequently cause phagocytosis of the target cell is referred to as antibody dependent cell-mediated phagocytosis (ADCP). Such function may be tested for using techniques known in the art. For example, as described in the Examples below, ADCP can be measured by conjugating the immunogenic polypeptides with fluorescent beads and mixing the conjugated beads with sera and THP-1 cells to determine the percentage of beads phagocytosed by the THP-1 cells (Ackerman et al., "A Robust, High-Throughput Assay to Determine the Phagocytic Activity of Clinical Antibody Samples," *J. Immunol. Methods* 366:8-19 (2011), which is hereby incorporated by reference in its entirety).

The immunogenic polypeptides described herein may also function to induce a neutralizing antibody response. A neutralizing antibody is an antibody that is capable of keeping an infectious agent, usually a virus, e.g., HIV, from infecting a cell by neutralizing or inhibiting its biological effect, for example by blocking the interaction between the receptors on the cell and the virus. Neutralization can happen when antibodies bind to specific viral antigens, blocking the pathogen from entering their host cells. Such function may be tested for using techniques known in the art. For example, as described in the Examples below, a neutralization assay may be performed in which serial dilutions of heat-inactivated sera are mixed with virus and incubated with TZM.b1 target cells that harbor a gene sensitive to HIV infection (Upadhyay et al., "Distinct Mechanisms Regulate Exposure of Neutralizing Epitopes in the V2 and V3 Loops of HIV-1 Envelope," *J. Virol.* 88:12853-12865 (2014), which is hereby incorporated by reference in its entirety). Gene expression can then be measured and percent neutralization calculated. According to certain embodiments, the immunogenic polypeptides described herein may also function to induce a neutralizing antibody response that is reactive to more than one pathogen subtype. For example, in certain embodiments, the immunogenic polypeptides described herein function to induce a neutralizing antibody response to one or more native pathogen epitopes (e.g., one or more epitopes of HIV Env glycoprotein gp120), where the antibody response includes cross-clade neutralizing antibodies (e.g., an antibody response reactive to more than one viral clade, which are described herein). In certain embodiments, the cross-clade antibody response is reactive to an envelope (or Env) polypeptide from HIV-1, Group M, and more than one of any of clades A-K. In certain embodiments, the cross-clade antibody response is to more than one of clades B, C, and CRF_01AE. In certain embodiments, the cross-clade antibody response is to clades B and C.

In one embodiment, the immunogenic polypeptide includes the amino acid sequence of SEQ ID NO: 8; SEQ ID NO: 9; or SEQ ID NO:10 as shown below.

```
V1V2(ZM53)-2F5K:
                                         (SEQ ID NO: 8)
PKPKFQEGERVLCFHGPLLYEAKCVKVAILAACVTLNCSKLNNATDGEMK

NCSFNATTELRDKKKQVYALFYKLDIVPLDGRMNSSEYRLINCEETVKYF

IHYSGWNKNWDEWVPESRVLKYVDTNLQKQRELQKANQEQYAEGKGLEVL

FQGPGHHHHHHHHSAWSHPQFEK;
```

V1V2(ZM53)-2J9C:

(SEQ ID NO: 9)
GSMKKVEAIIRPEKLEIVKKALSDAGYVGMTVSEVKGRGVQGGIVERYCV

TLNCSKLNNATDGEMKNCSFNATTELRDKKKQVYALFYKLDIVPLDGRNN

SSEYRLINCREYIVDLIPKVKIELVVKEEDVDNVIDIICENARTGDPGDG

KIFVIPVERVVRVRTKEEGKEALLEHGLEVLFQGPGHHHHHHHHSAWSHP

QFEK;
and

V1V2(A244)-2J9C:

(SEQ ID NO: 10)
GSMKKVEAIIRPEKLEIVKKALSDAGYVGMTVSEVKGRGVQGGIVERYCV

TLHCTNANLTKANLTNVNNRTNVSNIIGNITDEVRNCSFNIVITTELRDK

KQKVHALFYKLDIVPIEDNNDSSEYRLINCREYIVDLIPKVKIELVVKEE

DVDNVIDIICENARTGDPGDGKIFVIPVERVVRVRTKEEGKEALLEHGLE

VLFQGPGHHHHHHHHSAWSHPQFEK.

The immunogenic polypeptide may also comprise an immunogenic fragment of SEQ ID NO: 8; SEQ ID NO: 9; or SEQ ID NO:10. In certain embodiments described herein, the immunogenic polypeptide may be one that possesses at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with that of SEQ ID NO: 8, SEQ ID NO: 9, or SEQ ID NO: 10. Such immunogenic polypeptides retain the immunogenic function of SEQ ID NO: 8, SEQ ID NO: 9, or SEQ ID NO: 10. For example, such immunogenic polypeptides retain the ability to mimic the antibody-dependent functions described above, which may be tested for using techniques known in the art.

Further, the immunogenic peptides and/or epitope(s) described herein may be flanked on their respective N- and/or C-terminal ends by one or more (e.g., 2, 3, 4, 5, 6, 7, 8, 9, 10, 11, 12, 13, 14, 15, 16, 17, 18, 19, 20, etc.) amino acid residues. For instance, the epitope portion of the immunogenic polypeptide may include one or more amino acids (e.g., 2, 3, 4, 5, 6, 7, 8, 9, 10, etc.) on its N- and/or C-terminus to provide, e.g., flexibility, but that do not interfere with the immunogenic or antigenic properties of the immunogenic polypeptide, as described herein. Similarly, the immunogenic polypeptide may include additional amino acid residues at the N- and/or C-terminus that do not interfere with the immunogenic or antigenic properties of the immunogenic polypeptide as described herein. In certain embodiments, the immunogenic polypeptides described herein are of the following formula: $X_1$-$S_1$-$X_2$-$E_1$-$X_3$-$S_2$-$X_4$, where $S_1$ is a first scaffold portion of the scaffold polypeptide described herein; $E_1$ is a portion of the immunogenic polypeptide comprising one or more heterologous epitope(s) described herein; $S_2$ is a second scaffold portion of the scaffold polypeptide described herein; and $X_1$, $X_2$, $X_3$, and $X_4$ are optional additional portions comprising one or more (e.g., 2, 3, 4, 5, 6, 7, 8, 9, 10, 11, 12, 13, 14, 15, 16, 17, 18, 19, 20, etc.) amino acid residues that do not affect the immunogenic or antigenic properties of the immunogenic polypeptide as described herein.

The polypeptides of any of the embodiments described herein can be prepared by recombinant techniques, thereby providing for the insertion of the epitope(s) described herein within the amino acid sequence of the scaffold polypeptide (e.g., in the hairpin loop). The epitope may be inserted within the scaffold polypeptide without deletion of amino acids of the scaffold polypeptide. The epitope may also be inserted with removal of at least two amino acids from scaffold polypeptide at, e.g., the hairpin loop region. Deletions can be a deletion of at least two amino acid residues up to substantially all but one amino acid residue appearing in the hairpin loop. For example, two, three, four, five, or six amino acids may be deleted. Insertions can be an insertion of, e.g., at least two amino acid residues up to about 100 amino acid residues. The epitopes of the present invention preferably possess an amino acid sequence which is at least 40% identical or homologous to a corresponding native epitope sequence, as described above. The deletions, insertions, and replacements (relative to wild-type or previously known mutant) on the scaffolds can be achieved using recombinant techniques beginning with a known nucleotide sequence.

Another aspect of the present invention is a nucleic acid molecule encoding a polypeptide (e.g., an immunogenic polypeptide or fragment thereof) described according to any aspect described herein. In one embodiment the nucleic acid is DNA. Still a further aspect of the present invention is a DNA construct comprising a DNA molecule that encodes a polypeptide described according to any aspect described herein, a promoter-effective DNA molecule operably coupled 5' of the DNA molecule, and a transcription termination DNA molecule operably coupled 3' of the DNA molecule. Still a further aspect of the present invention is an expression vector into which is inserted the DNA construct described herein.

In one embodiment, the nucleic acid molecule comprises the nucleotide sequence encoding V1V2(ZM53)-2F5K (SEQ ID NO: 15) below.

CCGAAGCCTAAATTCCAGGAGGGTGAGCGAGTGCTGTGCTTTCATGGGCC

TCTTCTTTATGAAGCAAAGTGTGTAAAGGTTGCCATACTGGCCGCCTGCG

TGACCCTGAACTGCAGCAAGCTGAACAACGCCACCGACGGCGAGATGAAG

AACTGCAGCTTCAACGCCACCACCGAGCTGAGAGACAAGAAGAAGCAGGT

GTACGCCCTGTTCTACAAGCTGGACATCGTGCCCCTGGACGGCAGAAACA

ACAGCAGCGAGTACAGACTGATCAACTGCGAGGAGACCGTGAAATACTTC

ATACATTACAGTGGTTGGAATAAAAATTGGGATGAATGGGTTCCGGAGAG

CAGAGTACTCAAATACGTGGACACCAATTTGCAGAAACAGCGAGAACTTC

AAAAAGCCAATCAGGAGCAGTATGCAGAGGGGAAGGGCCTGGAAGTGCTG

TTCCAGGGCCCAGGCCACCACCATCACCATCATCACCACAGCGCCTGGTC

CCACCCCCAGTTCGAGAAG

In another embodiment, the nucleic acid molecule comprises the nucleotide sequence encoding V1V2(ZM53)-2J9C (SEQ ID NO: 16) below.

GGCAGCATGAAGAAGGTGGAGGCCATCATCAGACCCGAGAAGCTGGAGAT

CGTGAAGAAGGCCCTGAGCGACGCCGGCTACGTGGGCATGACCGTGAGCG

AGGTGAAGGGCAGAGGCGTGCAGGGCGGCATCGTGGAGAGATACTGCGTG

ACCCTGAACTGCAGCAAGCTGAACAACGCCACCGACGGCGAGATGAAGAA

CTGCAGCTTCAACGCCACCACCGAGCTGAGAGACAAGAAGAAGCAGGTGT

-continued

```
ACGCCCTGTTCTACAAGCTGGACATCGTGCCCTGGACGGCAGAAACAAC

AGCAGCGAGTACAGACTGATCAACTGCAGAGAGTACATCGTGGACCTGAT

CCCCAAGGTGAAGATCGAGCTGGTGGTGAAGGAGGAGGACGTGGACAACG

TGATCGACATCATCTGCGAGAACGCCAGAACCGGCGACCCCGGCGACGGC

AAGATCTTCGTGATCCCCGTGGAGAGAGTGGTGAGAGTGAGAACCAAGGA

GGAGGGCAAGGAGGCCCTGCTGGAGCACGGCCTGGAAGTGCTGTTCCAGG

GCCCAGGCCACCACCATCACCATCATCACCACAGCGCCTGGTCCCACCCC

CAGTTCGAGAAG
```

In another embodiment, the nucleic acid molecule comprises the nucleotide sequence encoding V1V2(A244)-2J9C (SEQ ID NO: 17) below.

```
GGCAGCATGAAGAAGGTGGAGGCCATCATCAGACCCGAGAAGCTGGAGA

TCGTGAAGAAGGCCCTGAGCGACGCCGGCTACGTGGGCATGACCGTGAG

CGAGGTGAAGGGCAGAGGCGTGCAGGGCGGCATCGTGGAGAGATACTGC

GTGACCCTGCACTGCACCAACGCCAACCTGACCAAGGCCAACCTGACCA

ACGTGAACAACAGAACCAACGTGAGCAACATCATCGGCAACATCACCGA

CGAGGTGAGAAACTGCAGCTTCAACATGACCACCGAGCTGAGAGACAAG

AAGCAGAAGGTGCACGCCCTGTTCTACAAGCTGGACATCGTGCCCATCG

AGGACAACAACGACAGCAGCGAGTACAGACTGATCAACTGCAGAGAGTA

CATCGTGGACCTGATCCCCAAGGTGAAGATCGAGCTGGTGGTGAAGGAG

GAGGACGTGGACAACGTGATCGACATCATCTGCGAGAACGCCAGAACCG

GCGACCCCGGCGACGGCAAGATCTTCGTGATCCCCGTGGAGAGAGTGGT

GAGAGTGAGAACCAAGGAGGAGGGCAAGGAGGCCCTGCTGGAGCACGGC

CTGGAAGTGCTGTTCCAGGGCCCAGGCCACCACCATCACCATCATCACC

ACAGCGCCTGGTCCCACCCCCAGTTCGAGAAG
```

Regardless of the approach used to prepare the nucleic acid molecules encoding the polypeptide(s) described herein, the nucleic acid can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences. A recombinant gene or DNA construct can be prepared prior to its insertion into an expression vector. For example, using conventional recombinant DNA techniques, a promoter-effective DNA molecule can be operably coupled 5' of a DNA molecule encoding the polypeptide and a transcription termination (i.e., polyadenylation sequence) can be operably coupled 3' thereof.

In accordance with embodiments described herein, the polynucleotides are inserted into an expression system or vector to which the molecule is heterologous. The heterologous nucleic acid molecule is inserted into the expression system or vector in proper sense (5'-→3') orientation relative to the promoter and any other 5' regulatory molecules, and correct reading frame. The preparation of the nucleic acid constructs can be carried out using standard cloning methods well known in the art as described by SAMBROOK & RUSSELL, MOLECULAR CLONING: A LABORATORY MANUAL (Cold Springs Laboratory Press, 2001), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if E. coli is used as a host cell, plasmids such as pUC19, pUC18 or pBR322 may be used. When using insect host cells, appropriate transfer vectors compatible with insect host cells include, pVL1392, pVL1393, pAcGP67 and pAcSecG2T, which incorporate a secretory signal fused to the desired protein, and pAcGHLT and pAcHLT, which contain GST and 6xHis tags (BD Biosciences, Franklin Lakes, N.J.). Viral vectors suitable for use in carrying out this aspect of the invention include, adenoviral vectors, adeno-associated viral vectors, vaccinia viral vectors, nodaviral vectors, and retroviral vectors. Other suitable expression vectors are described in SAMBROOK AND RUSSELL, MOLECULAR CLONING: A LABORATORY MANUAL (Cold Springs Laboratory Press, 2001), which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in CURRENT PROTOCOLS IN MOLECULAR BIOLOGY (Fred M. Ausubel et al. eds., 2003), which is hereby incorporated by reference in its entirety.

Different genetic signals and processing events control many levels of gene expression (e.g., DNA transcription and messenger RNA ("mRNA") translation) and subsequently the amount of scaffold polypeptides and fusion proteins that are produced and expressed by the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression. Depending upon the host system utilized, any one of a number of suitable promoters may be used. For instance, when using E. coli, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other E. coli promoters produced by recombinant DNA or other synthetic DNA techniques may be used to provide for transcription of the inserted gene. When using insect cells, suitable baculovirus promoters include late promoters, such as 39K protein promoter or basic protein promoter, and very late promoters, such as the p10 and polyhedron promoters. In some cases it may be desirable to use transfer vectors containing multiple baculoviral promoters. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. The promoters can be constitutive or, alternatively, tissue-specific or inducible. In addition, in some circumstances inducible (TetOn) promoters can be used.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and promote binding of mRNA to ribosomes by duplexing with the rRNA to allow correct positioning of the ribosome. For a review on maximizing gene expression, see Roberts and Lauer, "Maximizing Gene Expression on a Plasmid Using Recombination In Vitro," *Methods in Enzymology*, 68:473-82 (1979), which is hereby incorporated by reference in its entirety.

Yet another aspect of the present invention is a host cell transformed with the DNA construct described herein. The host cell can be a prokaryote or a eukaryote.

Host cells suitable for expressing the polypeptides described herein include any one of the more commonly available gram negative bacteria. Suitable microorganisms include *Pseudomonas aeruginosa, Escherichia coli, Salmonella gastroenteritis (typhimirium), S. typhi, S. enteriditis, Shigella flexneri, S. sonnie, S. dysenteriae, Neisseria gonorrhoeae, N. meningitides, Haemophilus influenzae, H. pleuropneumonias, Pasteurella haemolytica, P. multilocida, Legionella pneumophila, Treponema pallidum, T denticola, T. orales, Borrelia burgdorferi, Borrelia* spp., *Leptospira interrogans, Klebsiella pneumoniae, Proteus vulgaris, P. morganii, P. mirabilis, Rickettsia prowazeki, R. typhi, R. richettsii, Porphyromonas (Bacteroides) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A. salmonicida,* and *Yersinia pestis.*

In addition to bacteria cells, animal cells, in particular mammalian and insect cells, yeast cells, fungal cells, plant cells, or algal cells are also suitable host cells for transfection/transformation of the recombinant expression vector carrying an isolated polynucleotide molecules described herein. Mammalian cell lines commonly used in the art include Chinese hamster ovary cells (CHO), HeLa cells, baby hamster kidney cells, COS cells, HEK293S cells and many others. Suitable insect cell lines include those susceptible to baculoviral infection, including Sf9 and Sf21 cells.

Methods for transforming/transfecting host cells with expression vectors are well-known in the art and depend on the host system selected, as described in SAMBROOK & RUSSELL, MOLECULAR CLONING: A LABORATORY MANUAL (Cold Springs Laboratory Press, 2001), which is hereby incorporated by reference in its entirety. For bacterial cells, suitable techniques include calcium chloride transformation, electroporation, and transfection using bacteriophage. For eukaryotic cells, suitable techniques include calcium phosphate transfection, DEAE-Dextran, electroporation, liposome-mediated transfection, and transduction using retrovirus or any other viral vector. For insect cells, the transfer vector containing the polynucleotide construct of the present invention is co-transfected with baculovirus DNA, such as AcNPV, to facilitate the production of a recombinant virus resulting from homologous recombination between the scaffold-encoding polynucleotide construct in the transfer vector and baculovirus DNA. Subsequent recombinant viral infection of Sf cells results in a high rate of recombinant protein production.

In at least several of the various uses of the polypeptides of the embodiments described herein, it is often desirable for the polypeptides to be produced in substantially purified form, particularly when their administration to a patient is contemplated. Regardless of the expression system and host cell used to facilitate protein production, the expressed polypeptides and fusion proteins of the present invention can be readily purified using standard purification methods known in the art and described in PHILIP L. R. BONNER, PROTEIN PURIFICATION (Routledge 2007), which is hereby incorporated by reference in its entirety.

A second aspect of the present invention is directed to an isolated trimeric structure including three monomeric immunogenic polypeptide subunits assembled in a trimeric structure. Each of the immunogenic polypeptide subunits includes the isolated immunogenic polypeptide described herein, where the trimeric immunogenic structure constrains the one or more epitopes to the conformation that (i) is substantially similar to the one or more native epitopes of the pathogen in trimeric conformation and (ii) binds the antibody reactive to the pathogen.

Suitable immunogenic polypeptides are described above.

In one embodiment, the one or more epitopes is/are from (or mimic(s)) the V1V2 region of the surface envelope glycoprotein gp120 of the envelope polypeptide of an HIV virus (e.g., HIV-1), as described herein. In one embodiment, the one or more epitopes comprise(s) a V1V2 fragment of HIV-1 surface envelope glycoprotein gp120 where the trimeric structure constrains the V1V2 fragment to a conformation substantially similar to that of an HIV-1 virion's native surface envelope glycoprotein gp120. The trimeric conformation of an HIV-1 virion's native surface envelope glycoprotein gp120 may be characterized as having a unique five-stranded β-barrel structure with strands A, B, C, C', and D. In the trimer context, the V1V2 regions in the trimer join together at the apex center to form a top layer of the Env complex.

As used herein, "substantially similar" refers to one or more epitopes in a trimeric conformation that maintain(s) the functions of the native epitope(s) in trimeric conformation, such as the ability to bind to the same antibodies or induce an antibody-dependent immune response as described below.

In one embodiment, the scaffold polypeptide constrains the center mass of the amino acid residues of the disulfide-linked loop region immediately preceding the disulfide bond of the hairpin loop at about 10 to 14 Angstroms from the trimer axis, and tilts the vector of the hairpin loop direction about 10 to 30 degrees both outwards and clockwise around the axis.

In one embodiment, the scaffold polypeptide constrains the center mass of the amino acid residues of the disulfide-linked loop region immediately preceding the disulfide bond of the hairpin loop at about 12 Angstroms from the trimer axis, and tilts the vector of the hairpin loop direction about 20 degrees both outwards and clockwise around the axis.

Also contemplated are isolated antibodies raised against an immunogenic polypeptide according to the present invention, or a binding fragment thereof. According to certain embodiments of the present invention, the antibody can be present in a polyclonal antiserum or a monoclonal preparation.

The isolated antibodies of the present invention may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The isolated antibody can be a full length antibody, monoclonal antibody (including full length monoclonal antibody), polyclonal antibody, multispecific antibody (e.g., bispecific antibody), human, humanized or chimeric antibody, and antibody fragments, e.g., Fab fragments, F(ab') fragments, fragments produced by a Fab expression library, epitope-binding fragments of any of the above, and engineered forms of antibodies, e.g., scFv molecules, so long as they exhibit the desired neutralizing activity.

As noted above, the monoclonal antibody of the present invention can be a humanized antibody. Humanized antibodies are antibodies that contain minimal sequences from non-human (e.g., murine) antibodies within the variable regions. Such antibodies are used therapeutically to reduce antigenicity and human anti-mouse antibody responses when administered to a human subject. An antibody can be humanized by substituting the complementarity determining region (CDR) of a human antibody with that of a non-human antibody (e.g., mouse, rat, rabbit, hamster, etc.) having the desired specificity, affinity, and capability (Jones et al., "Replacing the Complementarity-Determining Regions in a Human Antibody With Those From a Mouse," *Nature* 321: 522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability. Polyclonal antibodies can be prepared by any method known in the art. Polyclonal antibodies can be raised by immunizing an animal (e.g., a rabbit, rat, mouse, donkey, etc.) with multiple subcutaneous or intraperitoneal injections of the relevant antigen (e.g., an isolated scaffold polypeptide, fusion protein, or immunogenic conjugate) diluted in sterile saline and combined with an adjuvant (e.g., Complete or Incomplete Freund's Adjuvant) to form a stable emulsion. The polyclonal antibody is then recovered from blood or ascites of the immunized animal. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc. Polyclonal antiserum can also be rendered monospecific using standard procedures (see e.g., Agaton et al., "Selective Enrichment of Monospecific Polyclonal Antibodies For Antibody-Based Proteomics Efforts," *J. Chromatography A* 1043(1):33-40 (2004), which is hereby incorporated by reference in its entirety).

Monoclonal antibodies can be prepared using hybridoma methods, such as those described by Kohler and Milstein, "Continuous Cultures of Fused Cells Secreting Antibody of Predefined Specificity," *Nature* 256:495-7 (1975), which is hereby incorporated by reference in its entirety. Using the hybridoma method, a mouse, hamster, or other appropriate host animal, is immunized to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against the scaffold, as determined by immunoprecipitation, immunoblotting, or by an in vitro binding assay such as radioimmunoassay (RIA) or enzyme-linked immunosorbent assay (ELISA) can then be propagated either in in vitro culture using standard methods (JAMES W. GODING, MONOCLONAL ANTIBODIES: PRINCIPLES AND PRACTICE (Academic Press 1986), which is hereby incorporated by reference in its entirety) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567 to Cabilly et al, which is hereby incorporated by reference in its entirety. Polynucleotides encoding a monoclonal antibody are isolated, from mature B-cells or hybridoma cell, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., "Phage Antibodies: Filamentous Phage Displaying Antibody Variable Domains," *Nature* 348:552-554 (1990); Clackson et al., "Making Antibody Fragments Using Phage Display Libraries," *Nature,* 352: 624-628 (1991); and Marks et al., "By-passing Immunization. Human Antibodies From V-gene Libraries Displayed on Phage," *J. Mol. Biol.* 222:581-597 (1991), which are hereby incorporated by reference in their entirety).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

A third aspect of the present invention relates to an immunogenic composition including the isolated immunogenic polypeptide according to the first aspect of the present invention and/or the trimeric structure according to the second aspect of the present invention. The immunogenic composition also includes an immunologically and pharmaceutically acceptable vehicle or excipient.

Immunogenic polypeptides and trimeric structures are described above.

Immunologically and pharmaceutically acceptable vehicle or excipients include, but are not limited to sterile liquids, such as water and oils, with or without the addition of a surfactant and other pharmaceutically and physiologically acceptable carriers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

The polypeptide, DNA molecule, antibody, or expression vector described herein, and immunogenic compositions comprising the same can be incorporated into a delivery vehicle to facilitate administration. Such delivery vehicles include, but are not limited to, biodegradable microspheres (MARK E. KEEGAN & W. MARK SALTZMAN, Surface Modified Biodegradable Microspheres for DNA Vaccine Delivery, in DNA VACCINES: METHODS AND PROTOCOLS 107-113 (W. Mark Saltzman et al., eds., 2006), which is hereby incorporated by reference in its entirety), microparticles (Singh et al., "Nanoparticles and Microparticles as Vaccine Delivery Systems," Expert Rev. Vaccine 6(5):797-808 (2007), which is hereby incorporated by reference in its entirety), nanoparticles (Wendorf et al., "A Practical Approach to the Use of Nanoparticles for Vaccine Delivery," J. Pharmaceutical Sciences 95(12):2738-50 (2006) which is hereby incorporated by reference in its entirety), liposomes (U.S. Patent Application Publication No. 2007/0082043 to Dov et al. and Hayashi et al., "A Novel Vaccine Delivery System Using Immunopotentiating Fusogenic Liposomes," Biochem. Biophys. Res. Comm. 261(3): 824-28 (1999), which are hereby incorporated by reference in their entirety), collagen minipellets (Lofthouse et al., "The Application of Biodegradable Collagen Minipellets as Vaccine Delivery Vehicles in Mice and Sheep," Vaccine 19(30):4318-27 (2001), which is hereby incorporated by reference in it entirety), and cochleates (Gould-Fogerite et al., "Targeting Immune Response Induction With Cochleate and Liposome-Based Vaccines," Adv. Drug Deliv. Rev. 32(3):273-87 (1998), which is hereby incorporated by reference in its entirety).

A fourth aspect of present invention relates to a method of inducing, in a subject, an antibody response against a pathogen. The method involves administering to the subject the immunogenic polypeptide according to the first aspect of the present invention and/or the isolated trimeric structure according to the second aspect of the present invention under conditions effective to induce, in the subject, an antibody response against the pathogen.

A fifth aspect of the present invention relates to a method of inducing, in a subject, an antibody response against a pathogen. The method involves administering to the subject the immunogenic composition according to the third aspect of the present invention under conditions effective to induce, in the subject, an antibody response against the pathogen.

Immunogenic polypeptides, isolated trimeric structures, and immunogenic compositions are described above.

In one embodiment, the immunogenic composition further comprises an adjuvant or immunostimulatory peptide or polypeptide that is different from said immunogenic polypeptide. For example, (a) ISAF-1 (5% squalene, 2.5% pluronic L121, 0.2% Tween 80) in phosphate buffered solution with 0.4 mg of threonyl-muramyl dipeptide; (b) de-oiled lecithin dissolved in an oil; (c) aluminum hydroxide gel; (d) a mixture of (b) and (c); (e) QS-21; (f) monophosphoryl lipid A adjuvant; or (g) incomplete Freund's adjuvant may be suitable adjuvants for use in the present invention.

Also contemplated are immunogenic polypeptides comprising the immunogenic polypeptide and/or the one or more epitopes described herein either fused to or chemically coupled to an immunostimulatory peptide or polypeptide. In one embodiment, the immunostimulatory peptide or polypeptide comprises an Fc region. As known in the art, the term "Fc region" is used to define a C-terminal region of an immunoglobulin heavy chain. The "Fc region" (also known as the "fragment crystallizable" or "tail" region) may be a native sequence Fc region or a variant Fc region. The Fc region of an immunoglobulin generally comprises two constant domains, $C_H2$ and $C_H3$. Typically, an Fc region includes a $C_H2$ and a $C_H3$ domain and can include at least a portion of the hinge domain, but does not usually include the entire $C_H1$ domain. Thus Fc refers to the last two constant region immunoglobulin domains of IgA, IgD, and IgG, and the last three constant region immunoglobulin domains of IgE and IgM. In one embodiment, the Fc domain is derived from a mammalian (including, e.g., human, rodent, non-human primate, rabbit, etc.) immunoglobulin. In one embodiment, the Fc domain is derived from the mammalian Fc region consisting of the heavy chain hinge and the $C_H2$ and $C_H3$ regions.

The immunoglobulin Fc region used as a fusion partner in the polypeptides describe herein generally may be from any mammalian species. Where it is undesirable to elicit an immune response in the host cell or animal against the Fc region, the Fc region may be derived from the same species as the host cell or animal. For example, a human immunoglobulin Fc region can be used when the host animal or cell is human; likewise, a murine immunoglobulin Fc region can be used where the host animal or cell will be a mouse.

The Fc-region or domain of the fusion polypeptides described herein may impart non-antigen binding functions to the polypeptide, termed "effector functions," such as complement binding, antibody-dependent cell cytotoxicity (ADCC), and other functions mediated through the binding of subregions of this dimeric structure with immune cell surface receptors, Fc-receptors. Certain natural and synthetic variants of the Fc-region polypeptides sequences with altered effector functions that are suitable for use in the fusion polypeptides described herein include the subclass variants; e.g. IgGi, IgG2i, IgG3i, IgG24; and mutant polypeptides as described in e.g. U.S. Pat. No. 5,624,821 to Winter, U.S. Pat. No. 6,528,624 to Idusogie, U.S. Pat. No. 7,183,387 to Presta, and U.S. Pat. No. 7,317,091 to Lazar et al., which are hereby incorporated by reference in their entirety.

In another embodiment, the immunogenic polypeptide and/or the one or more epitopes described herein may be further linked in-frame to an adjuvant polypeptide. The adjuvant polypeptide can be any adjuvant polypeptide known in the art, including, but not limited to, cholera toxin B, flagellin, human papillomavirus L1 or L2 protein, herpes simplex glycoprotein D (gD), complement C4 binding protein, TL4 ligand, and IL-1β. In one embodiment, the adjuvant polypeptide is cholera toxin B. The immunogenic polypeptides and/or the one or more epitopes may be linked directly to the adjuvant polypeptide or coupled to the adjuvant by way of a short linker sequence. Suitable linker sequences include glycine or serine-rich linkers described supra or other flexible immunoglobulin linkers as disclosed in U.S. Pat. No. 5,516,637 to Huang et al, which is hereby incorporated by reference in its entirety.

In another embodiment, the immunogenic polypeptides and/or the one or more epitopes described herein may be conjugated to an immunogenic carrier molecule. The immunogenic carrier molecule can be covalently or non-covalently bonded to the immunogenic polypeptide and/or the one or more epitopes described herein. Suitable immunogenic carrier molecules include, but are not limited to, serum albumins, chicken egg ovalbumin, keyhole limpet hemocyanin, tetanus toxoid, thyroglobulin, pneumococcal capsular polysaccharides, CRM 197, immunoglobulin molecules, alum, and meningococcal outer membrane proteins. Other suitable immunogenic carrier molecules include T-cell epitopes, such as tetanus toxoid (e.g., the P2 and P30 epitopes), Hepatitis B surface antigen, pertussis, toxoid, diphtheria toxoid, measles virus F protein, *Chlamydia trachomatis* major outer membrane protein, *Plasmodium falciparum* circumsporozite T, *P. falciparum* CS antigen, *Schistosoma mansoni* triose phosphate isomerase, *Escherichia coli* TraT, and Influenza virus hemagluttinin (HA). Other suitable immunogenic carrier molecules include promiscuous T helper cell epitopes which are derived from hepatitis B virus, *Bordetella pertussis, Clostridium tetani, Pertusaria trachythallina, E. coli, Chlamydia trachomatis*, Diphtheria, *P. falciparum*, and *Schistosoma mansoni* (see U.S. Pat. No. 6,906,169 to Wang; U.S. Patent Application Publication No. 20030068325 to Wang, and WO/2002/096350 to Wang, which are hereby incorporated by reference in their entirety). Yet other suitable carriers include T-helper cell epitopes derived from tetanus toxin, cholera toxin B, pertussis toxin, diphtheria toxin, measles virus F protein, hepatitis B virus surface antigen, *C. trachomitis* major outer membrane protein, *P. falciparum* circumsporozoite, *S. mansoni* triose phosphate isomerase, or *E. coli* TraT (see WO01/42306 to Chain, which is hereby incorporated by reference in its entirety). In one embodiment, the immunogenic carrier molecule is cholera toxin B covalently conjugated to the immunogenic polypeptides and/or the one or more epitopes described herein.

The immunogenic polypeptides and/or the one or more epitopes described herein can be linked to immunogenic carrier molecules by chemical crosslinking. Techniques for linking a peptide immunogen to an immunogenic carrier molecule include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine residues on one protein, and an amide linkage through the epsilon-amino on a lysine, or other free amino group in other amino acids. A variety of such disulfide/amide-forming agents are described by Jansen et al., "Immunotoxins: Hybrid Molecules Combining High Specificity and Potent Cytotoxicity," *Immun Rev* 62:185-216 (1982), which is hereby incorporated by reference in its entirety. Other bifunctional coupling agents form a thioether rather than a disulfide linkage. Many of these thio-etherforming agents are commercially available and include reactive esters of 6-maleimidocaproic acid, 2-bromoacetic acid, 2-iodoacetic acid, and 4-(N-maleimido-methyl)cyclohexane-1-carboxylic acid. The carboxyl groups can be activated by combining them with succinimide or 1-hydroxyl-2-nitro-4-sulfonic acid, sodium salt. The functions of immunogenic polypeptides are described above. Thus, the methods are effective to induce antibody-dependent cellular toxicity, antibody-dependent cellular phagocytosis, and/or a neutralizing antibody response.

Any of the compositions described herein can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions. Acceptable pharmaceutical carriers include solutions, suspensions, emulsions, excipients, powders, or stabilizers. The carrier should be suitable for the desired mode of delivery, discussed infra.

It is contemplated that the individual (or subject) to be treated in accordance with the present invention can be any mammal. In certain embodiments, the subject is a human. Veterinary uses are also contemplated. While the individual can be any mammal that is known to be susceptible to a viral or bacterial infection; the polypeptides of the present invention or the pharmaceutical composition containing the same may be derived from a genotype that is specific to the host mammal to be immunized in accordance with the present invention. For example, for inducing an immune response in humans it is preferable that the polypeptide is derived from a human viral or bacterial strain, or at least a strain that is capable of infecting humans. Moreover, the pharmaceutical composition can be multi-valent, containing antigen directed to different viral or bacterial strains, which collectively provide a more protective immune response.

As noted supra, the pharmaceutical composition can be administered by any means suitable for producing the desired immune response. The composition can be delivered repeatedly over a course of time, i.e., according to a prime/boost regimen, that achieves optimal enhancement of the immune response, which is discussed further infra. In the HIV vaccine field, prime/boost regimens are among the most effective for inducing protective antiviral antibodies (Abs) (Zolla-Pazner et al., "Cross-Clade HIV-1 Neutralizing Antibodies Induced with V3-Scaffold Protein Immunogens following Priming with gp120 DNA," *J. Virol.* 85(19): 9887-9898 (2011); Tomaras et al., "Strategies for Eliciting HIV-1 Inhibitory Antibodies," *Curr. Opin. HIV AIDS* 5:421-427 (2010), which are hereby incorporated by reference in their entirety). The mechanism by which prime/boost immunization works follows fundamental immunologic principles in which T and B memory cells are established with priming. Subsequently, activation and proliferation of Ab-producing B cells are stimulated by the boosting immunogen, working in conjunction with cytokines produced by the memory T cells. While nonprotein primes can induce excellent cellmediated immunity, proteins are particularly effective for eliciting Ab responses, and the combination of nonprotein priming and protein boosting gives a much stronger Ab response than does delivery of protein vaccines alone (Zolla-Pazner et al., "Cross-Clade HIV-1 Neutralizing Antibodies Induced with V3-Scaffold Protein Immunogens following Priming with gp120 DNA," *J. Virol.* 85(19): 9887-9898 (2011); Kim et al., "HIV Vaccines: Lessons Learned and the Way Forward," *Curr. Opin. HIV AIDS* 5:428-434 (2010); Lu, "Heterologous Prime-Boost Vaccination," *Curr. Opin. Immunol.* 21:346-351 (2009), which are hereby incorporated by reference in their entirety). The prime/boost regimen may involve administering the pharmaceutical composition according to the present invention in combination with a further pharmaceutical composition. The further pharmaceutical composition may include an immunogenic priming agent. The immunogenic priming agent may be a protein or nonprotein protein priming agent. The immunogenic priming agent may be any immunogenic polypeptide (or immunogenic fragment thereof), as described herein, and/or a nucleotide molecule encoding such an immunogenic polypeptide (or immunogenic fragment thereof). The non-protein priming agent may be derived from a pathogen, as described herein. In one embodiment, the non-protein priming agent comprises a nucleic acid molecule encoding HIV gp120 or a portion thereof. In one embodiment, the nucleic acid molecule is codon optimized. In one embodiment, the non-protein priming agent comprises a nucleic acid molecule encoding HIV gp120 (or portion thereof) from HIV clade C primary isolate ZM109F. In one embodiment, the priming agent comprises the nucleotide sequence of SEQ ID NO: 27 as shown below, or an immunogenic fragment thereof: CTGTGGGTCACCGTGTACTACGGCGTGCCCGTGTGGAAAGAGGCCAAGACCACC CTGTTCTGCGCCAGCGACGCCAAGAGCTACGAGCGCGAGGTGCACAACGTGTGG GCCACCCACGCCTGCGTGCCCACCGACCCTGATCCCCAGGAACTGGTCATGGCC AACGTGACCGAGAACTTCAACATGTGGAAGAACGACATGGTGGACCAGATGCAC GAGGACATCATCAGCCTGTGGGACCAGAGCCTGAAGCCCTGCGTGAAGCTGACC CCCCTGTGCGTGACCCTGAACTGCACAAGCCCTGCCGCCCACAACGAGAGCGAG ACAAGAGTGAAGCACTGCAGCTTCAACATCACCACCGACGTGAAGGACCGGAA GCAGAAAGTGAACGCCACCTTCTACGACCTGGACATCGTGCCCCTGAGCAGCAG CGACAACAGCAGCAACAGCTCCCTGTACCGGCTGATCAGCTGCAACACCAGCAC CATCACCCAGGCCTGCCCCAAGGTGTCCTTCGACCCCATCCCCATCCACTACTGC GCCCCTGCCGGCTACGCCATCCTGAAGTGCAACAACAAGACCTTCAGCGGCAAG GGCCCCTGCAGCAACGTGTCCACCGTGCAGTGCACCCACGGCATCAGACCCGTG GTGTCCACCCAGCTGCTGCTGAACGGCAGCCTGGCCGAAGAGGAAATCGTGATC AGAAGCGAGAACCTGACCGACAACGCCAAGACCATCATCGTGCACCTGAACAA GAGCGTGGAAATCGAGTGCATCAGGCCCGGCAACAACACCAGAAAGAGCATCC GGCTGGGCCCTGGCCAGACCTTCTATGCCACCGGCGACGTGATCGGCGACATCC GGAAGGCCTACTGCAAGATCAACGGCAGCGAGTGGAACGAGACACTGACAAAG GTGTCCGAGAAGCTGAAAGAGTACTTCAACAAGACAATCCGCTTCGCCCAGCAC TCTGGCGGCGACCTGGAAGTGACCACCCACAGCTTCAACTGCAGAGGCGAGTTC TTCTACTGCAACACCTCCGAGCTGTTCAACAGCAACGCCACCGAGAGCAACATC ACCCTGCCCTGCCGGATCAAGCAGATCATCAATATGTGGCAGGGCGTGGGCAGA GCTATGTACGCCCCTCCCATCCGGGGCGAGATCAAGTGCACCTCCAACATCACC GGCCTGCTGCTGACCCGGGACGGCGGAAACAACAACAACAGCACCGAGGAAAT CTTCCGGCCCGAGGGCGGCAACATGCGGGACAATTGGCGGAGCGAGCTGTACAA GTACAAGGTGGTGGAAATCAAGCCCCTGGGAATCGCCCCCACCGAGGCCAAGCG GCGGGTGGTGCAG (SEQ ID NO: 27) In one embodiment, the priming agent possesses at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with that of SEQ ID NO: 27. The priming agent may be administered sequentially or simultaneously with the pharmaceutical composition according to the present invention.

For prophylactic treatment against viral or bacterial infection, it is intended that the composition(s) described herein can be administered prior to exposure of an individual to the virus or bacteria and that the resulting immune response can inhibit or reduce the severity of the viral or bacterial infection such that the virus or bacteria can be eliminated from the individual. The pharmaceutical compositions of the present invention can also be administered to an individual for therapeutic treatment. In accordance with one embodiment, it is intended that the composition(s) of the present invention can be administered to an individual who is already exposed to the virus or bacteria. The resulting enhanced immune response can reduce the duration or severity of the existing viral or bacterial infection, as well as minimize any harmful consequences of untreated viral or bacterial infections. The composition(s) can also be administered in combination other therapeutic anti-viral or anti-bacterial regimen. In asymptomatic patients, treatment can begin at any age (e.g., 10, 20, 30 years of age). Treatment typically entails multiple dosages over a period of time. Treatment can be monitored by assaying antibody, or activated T-cell or B-cell responses to the therapeutic agent over time. If the response falls, a booster dosage is indicated.

In prophylactic applications, pharmaceutical compositions containing the immunogenic polypeptides are administered to a patient susceptible to, or otherwise at risk of, the particular viral or bacterial infection in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions containing an antibody according to the present invention are administered to a patient suspected of, or already suffering from, such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

The presence of a humoral immunological response can be determined and monitored by testing a biological sample (e.g., blood, plasma, serum, urine, saliva feces, CSF or lymph fluid) from the subject for the presence of antibodies directed to the immunogenic polypeptide. Methods for detecting antibodies in a biological sample are well known in the art, e.g., ELISA, Dot blots, SDS-PAGE gels or ELISPOT. The presence of a cell-mediated immunological response can be determined by proliferation assays (CD4$^+$ T cells) or CTL (cytotoxic T lymphocyte) assays which are readily known in the art.

Effective doses of the compositions of the present invention for the prevention or treatment of the above described viral or bacterial infections vary depending upon many different factors, including mode of administration, target site, physiological state of the patient, other medications administered, and whether treatment is prophylactic or therapeutic. Dosages need to be titrated to optimize safety and efficacy. The amount of immunogen depends on whether adjuvant is also administered, with higher dosages being required in the absence of adjuvant. The amount of an immunogen for administration sometimes varies from 1-500 µg per patient and more usually from 5-500 µg per injection for human administration. Occasionally, a higher dose of 1-2 mg per injection is used. Typically about 10, 20, 50, or 100 µg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for each microgram of immunogen.

The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at time intervals, such as 6 week intervals. Another regimen consists of an immunization followed by booster injections 1, 2, and 12 months later. Another regimen entails an injection every two months for life. Alternatively, booster injections can be on an irregular basis as indicated by monitoring of immune response. In one embodiment, a priming immunization is given at 2 week intervals for the first 4 weeks followed by booster injections 6 and 10 weeks later. In another embodiment, a priming immunization is given at 4 week intervals for the first 8 weeks followed by booster injections 6 and 10 weeks later. In another embodiment, immunizations are given at 4 weeks, 12 weeks, and 20 weeks.

For passive immunization with an antibody raised against an immunogenic polypeptide according to the present invention, or a binding fragment thereof, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly, or yearly. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogenic polypeptides range from about 10 ng to 1 g, 100 ng to 100 mg, 1 µg to 10 mg, or 30-300 µg DNA per patient. Doses for infectious viral vectors vary from 10-100, or more, virions per dose.

A sixth aspect of the present invention relates to an isolated immunogenic polypeptide. The isolated immunogenic polypeptide includes a scaffold polypeptide having a native loop. The native loop is modified to include one or more epitopes heterologous to the scaffold polypeptide and from an amino acid loop linked by a disulfide bond, where the scaffold polypeptide directs self-assembly with four other of said scaffold polypeptides to form a pentameric structure. The pentameric structure constrains the one or more epitopes to a conformation capable of binding an antibody reactive to one or more native pathogen epitopes.

In certain embodiments, the isolated immunogenic polypeptide includes a scaffold polypeptide having a native loop. The native loop is modified to include an epitope heterologous to the scaffold polypeptide and from an amino acid loop linked by a disulfide bond, where the scaffold polypeptide directs self-assembly with four other of said scaffold polypeptides to form a pentameric structure. The pentameric structure constrains the epitope to a conformation capable of binding an antibody reactive to a native pathogen epitope.

As used herein, the "native loop" is contemplated to encompass, for example, a naturally occurring amino acid loop formed or linked by a disulfide bond, a hairpin loop, and any other amino acid loop structure of the scaffold polypeptide described herein.

Exemplary pathogens are described above. In one embodiment the pathogen is HIV. In one embodiment, the antibody is reactive to the V1 and/or V2 region of the HIV-1 surface envelope glycoprotein gp120, as described above. In another embodiment, the antibody is reactive to the V3 region of HIV-1 surface envelope glycoprotein gp120.

Suitable epitope(s) for use in accordance with this and related aspects described herein are the same as those set forth above.

In one embodiment, the scaffold polypeptide is a modified typhoid toxin subunit B ("TTB"). Typhoid toxin is an AB-type toxin, meaning that it consists of an active "A" component and a binding "B" component. In particular, typhoid toxin contains two A subunits (PltA, an ADP ribosyltransferase, and CdtB, a DNAase that induces cell-cycle arrest) bound to a pentamer of B subunits (PltB) (See Song et al., "Structure and Function of the *Salmonella Typhi* Chimeric A(2)B(5) Typhoid Toxin," *Nature* 499:350-354 (2013), which is hereby incorporated by reference in its entirety). The crystal structure of TTB and the related sequence information is found at Protein Data Bank (PDB) ID 4K6L (Song et al., 10.2210/pdb4k6l/pdb, Released Jul. 17, 2013, which is hereby incorporated by reference in its entirety). The amino acid sequence for unmodified TTB is as follows:

(SEQ ID NO: 11)
EWTGDNTNAYYSDEVISELHVGQIDTSPYFCIKTVKANGSGTPVVAC
AVSKQSIWAPSFKELLDQARYFYSTGQSVRIHVQKNIWTYPLFVNTF
SANALVGLSSCSATQCFGPK

Those portions retained in the immunogenic polypeptide of SEQ ID NO: 11, described below, are presented in bold; the amino acids in the native loop replaced with an epitope described herein are shown in underline. Although 4 amino acids were replaced in the native loop, any number of amino acids in the loop region may be replaced.

Also contemplated for use in accordance with embodiments described herein are variants, isoforms, and homologs of TTB. Such molecules may possess at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with that of TTB.

In one embodiment, the immunogenic polypeptide includes the amino acid sequence of SEQ ID NO: 12. In another embodiment, the immunogenic polypeptide includes the amino acid sequence of SEQ ID NO: 14. These sequences are shown below.

V1V2(ZM109)-TTB has the amino acid sequence:

(SEQ ID NO: 12)
EWTGDNTNAYYSDEVISELHVGQIDTSPYFCIKTVKANGAGTPVVACAVS

KQSIWAPSFKELLDQARYFYSTGQSVRIHVQKNIWTYPLFVNTFSANALV

GLSSCVKLTPLCVTLNCTSPAAHNESETRVKHCSFNITTDVKDRKQKVNA

TFYDLDIVPLSSSDNSSNSSLYRLISCNTSTITQACFGPKLEVLFQGPGH

HHHHHHHAWSHPQFEK.

V3(ZM109)-TTB has the amino acid sequence:

(SEQ ID NO: 14)
EWTGDNTNAYYSAEVISELHVGQIDTSPYFCIKTVKANGAGTPVVACAVS

KQSIWAPSFKELLDQARYFYSTGQSVRIEVQKNIWTYPLFVNTFSANALV

GLSSCIRPGNNTRKSIRLGPGQTFYATGDVIGDIRKAYCFGPKLEVLFQG

PGHHHHHHHSAWSHPQFEK.

The immunogenic polypeptide may also comprise an immunogenic fragment of SEQ ID NO:12 or SEQ ID NO:14. In one embodiment the immunogenic polypeptide possesses at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with that of SEQ ID NO: 12. In one embodiment the immunogenic polypeptide possesses at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with that of SEQ ID NO: 14.

A seventh aspect of the present invention relates to an isolated pentameric structure including five monomeric immunogenic polypeptide subunits assembled in a pentameric structure. Each of the immunogenic polypeptide subunits includes the isolated immunogenic polypeptide according to the sixth aspect of the present invention, where the pentameric structure constrains the one or more epitopes to the conformation that binds the antibody reactive to the pathogen.

In one embodiment, the pentameric structure hosts five copies of a V1V2 epitope from HIV-1 gp120 and constrains the epitopes such that they are recognized by V2q and V2l antibodies. In one embodiment, the pentameric structure hosts five copies of a V3 epitope from HIV-1 gp120 and constrains the epitopes such that they are recognized by V2q and V2l antibodies.

In one embodiment, the scaffold polypeptide of the isolated pentameric structure is a modified typhoid toxin subunit B ("TTB") as described above.

In one embodiment, the unmodified scaffold polypeptide comprises the amino acid sequence of SEQ ID NO: 11.

An eighth aspect of the present invention relates to an immunogenic composition including the isolated immunogenic polypeptide according to the sixth aspect of the present invention or the pentameric structure of the seventh aspect of the present invention. The immunogenic composition also includes an immunologically and pharmaceutically acceptable vehicle or excipient. Immunogenic polypeptides and pentameric structures are described above. Suitable immunogenic compositions and uses thereof (including, e.g., suitable components, modes of administration, dosing, etc.) are also described above.

Also contemplated accordance with embodiments described herein are immunogenic compositions comprising combinations of one or more different immunogenic polypeptides, trimeric structures, and/or pentameric structures described herein and use of such compositions in accordance with the methods of the present invention described herein inducing, in a subject, an antibody response against a pathogen. For example, in certain embodiments the immunogenic composition comprises: (a) two or more different immunogenic polypeptides according to the present invention where the scaffold polypeptide directs self-assembly with two other of the scaffold polypeptides to form a trimeric structure, as described herein above; (b) two or more different trimeric structures according to the present invention, as described herein above; (c) two or more different immunogenic polypeptides of the present invention where the scaffold polypeptide directs self-assembly with four other of the scaffold polypeptides to form a pentameric structure, as described above; (c) two or more different pentameric structures according to the present invention, as described herein above; (d) one or more immunogenic polypeptides according to the present invention where the scaffold polypeptide directs self-assembly with two other of the scaffold polypeptides to form a trimeric structure (as described herein above) in combination with one or more immunogenic polypeptides of the present invention where the scaffold polypeptide directs self-assembly with four other of the scaffold polypeptides to form a pentameric structure (as described herein above); (e) one or more trimeric structures according to the present invention (as described herein above) in combination with one or more pentameric structures according to the present invention (as described herein above) or (f) any combination of (a), (b), (c), (d), and (e). In certain embodiments, for example, the immunogenic composition comprises one or more of V1V2(ZM53)-2F5K (SEQ ID NO:8), V1V2(ZM53)-2J9C (SEQ ID NO:9), V1V2 (A244)-2J9C (SEQ ID NO:10), V1V2(ZM109)-TTB (SEQ ID NO:12), and V3 (ZM109)-TTB (SEQ ID NO:14). In certain embodiments, for example, the immunogenic composition comprises one or more of: a trimeric structure comprising three monomeric immunogenic polypeptides of V1V2(ZM53)-2F5K (SEQ ID NO:8) assembled in a trimeric structure; a trimeric structure comprising three monomeric immunogenic polypeptides of V1V2(ZM53)-2J9C (SEQ ID NO:9) assembled in a trimeric structure; a trimeric structure comprising three monomeric immunogenic polypeptides of V1V2(A244)-2J9C (SEQ ID NO:10) assembled in a trimeric structure; a pentameric structure comprising five monomeric immunogenic polypeptides of V1V2(ZM109)-TTB (SEQ ID NO:12) assembled in a pentameric structure; and a pentameric structure comprising five monomeric immunogenic polypeptides of V3 (ZM109)-TTB (SEQ ID NO:14) assembled in a pentameric structure. In one embodiment, the immunogenic composition comprises V1V2/ZM53-2F5K (SEQ ID NO:8) and V3/ZM109-TTB (SEQ ID NO:14). In one embodiment, the immunogenic composition comprises a trimeric structure comprising three monomeric immunogenic peptides of V1V2/ZM53-2F5K (SEQ ID NO:8) assembled in a trimeric structure and a pentameric structure comprising five monomeric immunogenic polypeptides of V3/ZM109-TTB (SEQ ID NO:14) assembled in a pentameric structure.

In one embodiment, the immunogenic composition further comprises an adjuvant or immunostimulatory peptide or polypeptide that is different from the immunogenic polypeptide.

A ninth aspect of the present invention relates to a method of inducing, in a subject, an antibody response against a pathogen. The method involves administering to the subject the immunogenic polypeptide according to the sixth aspect of the present invention and/or the isolated pentameric structure according to the seventh aspect of the present invention under conditions effective to induce, in the subject, an antibody response against the pathogen.

A tenth aspect of the present invention relates to a method of inducing, in a subject, an antibody response against a pathogen. The method involves administering to the subject the immunogenic composition according to the eighth aspect of the present invention under conditions effective to induce, in the subject, an antibody response against the pathogen.

Immunogenic polypeptides, isolated pentameric structures, immunogenic compositions, and methods of administration are described above.

In one embodiment, the immunogenic composition further comprises an adjuvant or immunostimulatory peptide or polypeptide that is different from the immunogenic polypeptide.

The functions of immunogenic polypeptides are described above. Thus, the methods are effective to induce antibody-dependent cellular toxicity, antibody-dependent cellular phagocytosis, and/or a neutralizing antibody response.

EXAMPLES

The examples below are intended to exemplify the practice of the present invention but are by no means intended to limit the scope thereof.

Materials and Methods for Examples 1-4

Ethics statement. Rabbit experiments were performed according to the guidelines of the Animal Welfare Act at University of Massachusetts Medical School in its animal facility which is fully accredited by AAALAC International with a current Animal Welfare Assurance on file (OLAW A3886-01). The immunization protocol was reviewed and approved by the Institutional Animal Care and Use Committees of both the University of Massachusetts Medical School and the NYU School of Medicine.

Design of trimeric V1V2 Scaffolds. Two trimeric V1V2 scaffold immunogens, V1V2(ZM53)-2J9C and V1V2 (ZM109)-2F5K, were designed using the Internal Coordinate Mechanics (ICM) molecular modeling environment (Abagyan et al., "ICM—A New Method for Protein Modeling and Design—Applications to Docking and Structure Prediction from the Distorted Native Conformation," *Journal of Computational Chemistry* 15:488-506 (1994), which is hereby incorporated by reference in its entirety). A pipeline of filters was implemented to screen the protein databank (PDB; www.rcsb.org/pdb/) for scaffolds with desired structural features. Briefly, a low resolution EM density map (EMD-2241) from the electron microscopy study of the BG505 SOSIP/PG9 complex (Julien et al., "Asymmetric Recognition of the HIV-1 Trimer By Broadly Neutralizing Antibody PG9," *Proc. Natl. Acad. Sci. USA* 110:4351-4356 (2013), which is hereby incorporated by reference in its entirety), and the X-ray structure of scaffolded V1V2 domain in complex with PG9 (McLellan et al., "Structure of HIV-1 gp120 V1/V2 Domain With Broadly Neutralizing Antibody PG9," *Nature* 480:336-343 (2011), which is hereby incorporated by reference in its entirety) was used to reconstruct approximately the location of the V1V2 domain within the trimer context. Using this reconstruction, trimeric scaffold proteins were sought that could potentially position engrafted V1V2 domains in a similar manner. Given approximate nature of the starting data, it was not expected to reproduce native trimer configuration exactly. Rather, it was hypothesized that (1) even approximately correct configuration should reduce exposure of irrelevant epitopes and possibly enhance presentation of quaternary-dependent epitopes; and (2) interactions between V1V2 protomers can be expected to promote native-like configurations provided sufficient degree of flexibility is retained at the graft-scaffold junction.

In the scaffolded V1V2/PG9 complex structure, the V1V2 domain extends from a beta-hairpin present on the scaffold (1FD6), indicating that V1V2 can be potentially installed and folded correctly on beta-hairpins within other proteins. Therefore, trimeric proteins with beta-hairpins that are oriented in such a way that V1V2 domains, when engrafted in these hairpins, could form native trimer-like configuration were sought.

Symmetric homotrimeric structures were extracted from PDB. Within each structure, beta-hairpins (if present) were identified. Each hairpin was checked for surface exposure so that a domain grafted on it could potentially extend into open space without colliding with the scaffold. For each hairpin, its position and orientation with respect to the 3-fold axis of the trimeric assembly was assessed in terms of distance from the trimer axis and two angles (FIG. 1).

Target parameters inferred from the approximate reconstruction of the V1V2 domain position within the trimer were as follows: center mass of the residue pair (Ala125 and Gln197) immediately preceding the disulfide (Cys126 and Cys196) that delimits V1V2 domain was ~12 Å from the trimer axis, and the vector of the β-hairpin direction was tilted ~20 degrees both outwards and clockwise around the axis (when looking from above the trimer apex). Scaffolds that had these three parameters closest to the target were further evaluated by superimposing N- and C-terminal strands of the V1V2 domain structure onto corresponding strands of the scaffold hairpin to create a simple model of the graft-scaffold construct, which was assessed for clashes between the V1V2 domain and the scaffold or between the V1V2s themselves. Finally, complete models were built for the best candidates, energy-minimized, and final scaffold selection was made upon visual inspection of the models.

Typhoid toxin subunit B (TTB)-based immunogen. A crystal structure of typhoid toxin complex (PDB ID 4K6L) was used to identify a disulfide bond at the C-terminus of subunit B that is suitable for insertion of the V1V2 domain (Song et al., "Structure and Function of the *Salmonella Typhi* Chimaeric A(2)B(5) Typhoid Toxin," *Nature* 499:350-354 (2013), which is hereby incorporated by reference in its entirety). A small loop between residues Cys128 and Cys133 in TTB was replaced with V1V2 amino acids between Cys126 and Cys196 of ZM109 gp120. The structure of V1V2 in the PG9 complex was used to model the scaffolded pentamer, which showed that there were no clashes between the V1V2 regions in the pentamer (FIG. 1D). This construct is named V1V2(ZM109)-TTB.

Fc-linked immunogens. Two types of Fc-linked immunogens were constructed based on the available V1V2 scaffolds by linking them with the rabbit Fc fragment consisting of the heavy chain hinge and the CH2 and CH3 regions. The first type V1V2(ZM109)-1FD6-Fc, based on the 1FD6 scaffolded V1V2 used in crystallizing V2q mAbs (McLellan et al., "Structure of HIV-1 gp120 V1/V2 Domain With Broadly Neutralizing Antibody PG9," *Nature* 480:336-343 (2011); Pancera et al., "Structural Basis for Diverse N-Glycan Recognition by HIV-1-Neutralizing V1-V2-Directed Antibody PG16," *Nat. Struct. Mol. Biol.* 20:804-813 (2013), each of which is hereby incorporated by reference in its entirety), is structurally constrained. The second type V1V2 (1086)-Fc and V1V2(ZM109)-Fc, based on the V1V2 tags (Liao et al., "Vaccine Induction of Antibodies Against a Structurally Heterogeneous Site of Immune Pressure Within HIV-1 Envelope Protein Variable Regions 1 and 2," *Immunity* 38:176-186 (2013), which is hereby incorporated by reference in its entirety), is structurally unconstrained. The rabbit Fc gene was first cloned into the XbaI/BamHI sites of the mammalian expression vector pVRC8400 (40), and an NheI site was engineered preceding the rabbit Fc gene, encoded in a spacer between the genes of the V1V2 domain or scaffold and Fc. V1V2(ZM109)-1FD6, V1V2(1086), or V1V2(ZM109) was cloned into the EcoRV/NheI sites of the modified expression vector pVRC8400.

Production of V1V2 immunogens. Gene constructs were codon optimized for mammalian cell expression and synthesized by commercial vendors with a secretion signal, and, for non-Fc linked ones, a C-terminal Human Rhinovirus (HRV) 3C protease cleavage site, an 8×His tag, and a Strep-Tag II. They were then cloned into the modified expression vector pVRC8400 (kindly provided by Vaccine Research Center, National Institutes of Health) (Barouch et al., "A Human T-cell Leukemia Virus Type 1 Regulatory Element Enhances the Immunogenicity of Human Immunodeficiency Virus Type 1 DNA Vaccines in Mice and Nonhuman Primates," *J. Virol.* 79:8828-8834 (2005), which is hereby incorporated by reference in its entirety). Plasmid DNAs encoding these immunogens were transiently transfected into HEK293S GnTI-/- cells (Reeves et al., "Structure and Function in Rhodopsin: High-Level Expression of Rhodopsin With Restricted and Homogeneous N-Glycosylation by a Tetracycline-Inducible N-Acetylglucosaminyltransferase I-Negative HEK293S Stable Mammalian Cell Line," *Proc. Natl. Acad. Sci. USA* 99:13419-13424 (2002), which is hereby incorporated by reference in its entirety), cultured in Erlenmeyer flasks using 15-25% of the nominal volume and rotated at 110-130 rpm under standard humidified conditions (37° C. and 5% CO2). Cells were allowed to secrete the V1V2 immunogens for 72 hours. For V1V2 (ZM53)-2J9C, V1V2(ZM53)-2F5K, and V1V2(ZM109)-TTB, cell supernatants were concentrated, and filtered and loaded onto Ni-NTA beads, and proteins were eluted with 600 mM imidazole. For V1V2(ZM109)-1FD6-Fc, V1V2 (1086)-Fc and V1V2(ZM109)-Fc, cell supernatants were concentrated, filtered, and loaded onto Protein A columns; proteins were eluted with citric acid. The immunogens were flash frozen and stored at −80° C. The antigenicity of the V1V2-scaffold proteins was tested by ELISA with various human monoclonal antibodies.

Chemical conjugation of V1V2(ZM109)-1FD6 and Cholera Toxin B subunit (CTB). Purified cholera toxin subunit B (CTB, Sigma-Aldrich) and V1V2(ZM109)-1FD6 were chemically conjugated using the heterobifunctional crosslinker N-succinimidyl 3-(2-pyridyldithio) propionate (SPDP; Thermo Scientific). One milligram of V1V2 (ZM109)-1FD6 (2 mg/ml in PBS) was incubated with SPDP (0.6 mM, final concentration) for 1 hour at room temperature to add pyridyl disulfide groups to the primary amines of the protein. The reaction mixture was then desalted and buffer-exchanged to PBS by a size exclusion membrane filter to remove excess reagent and by-products (pyridine 2-thione). Similarly, 1 mg of CTB (2 mg/ml in PBS) was incubated with SPDP (0.6 mM, final concentration) for 1 hour at room temperature and then desalted and buffer-exchanged to PBS. Pyridyldithiol-activated CTB was then incubated with dithiothreitol (DTT; 50 mM) for 30 min at room temperature to expose the sulfhydryl groups and then desalted and buffer exchanged to PBS as before. Finally, equal amounts of pyridyldithiol-activated V1V2(ZM109)-1FD6 and sulfhydryl-activated CTB were mixed, followed by incubation at room temperature overnight for conjugation. The conjugated sample was desalted as before, and the endotoxin content was measured to confirm that there had been no significant contamination during the conjugation process.

Immunization of rabbits. Female New Zealand White rabbits, 6 to 8 weeks old (with a body weight of ~2 kg), were purchased from Harlan Laboratories (Indianapolis, Ind.) and housed in the animal facility managed by the Department of Animal Medicine at the University of Massachusetts Medical School in accordance with an IACUC-approved protocol. Three to five rabbits were included in each immunization group. For the priming immunizations, all rabbits received codon-optimized gp120.ZM109F DNA in the pJW4303 plasmid and were immunized at weeks 0, 2, and 4 using a Bio-Rad Helios gene gun (Bio-Rad Laboratories, Hercules, Calif.). The gp120 DNA vaccine plasmids were applied as a coating onto 1.0 µm gold beads at a ratio of 2 µg of DNA per mg of gold. Each gene gun shot delivered 1 µg of DNA to a total of 36 non-overlapping sites on the shaved abdominal skin for each DNA immunization. In two of the groups (H3.4 and H3.5; see Table 3), the rabbits also received protein immunogens at the same time as DNA. For the boosting immunizations, the animals received two doses of either gp120(ZM109) or one of the V1V2-scaffold immunogens at weeks 10 and 14. For all protein immunizations, a total of 100 µg of the gp120 protein or an individual V1V2-scaffold protein together with incomplete Freund adjuvant (IFA) was administered intramuscularly (IM). Serum samples were collected prior to immunization and 2 weeks after each immunization.

ELISA analysis of V1V2 mAbs and antibodies in sera from immunized rabbits. ELISAs were performed using Immulon 4HBX plates coated with antigens at a concentration of 1 µg/ml and incubating overnight at 4° C. After blocking with PBS with 3% BSA for 1.5 hours, mAbs were added at a concentration of 10 µg/ml. For serial titration of test sera, ELISAs were performed with a starting dilution of 1:100, and individual pre-immune sera were used as negative controls. Following a 2-hour incubation and three washes with PBS-Tween20 (0.05%), a 1:2000 dilution of alkaline phosphatase-conjugated goat anti-rabbit IgG (Southern Biotech) was added. After a 1-hour incubation, plates were washed three times with PBS-Tween20. Alkaline phosphatase substrate (Sigma) was added, and plates were read 30 min later at a wavelength of 405 nm. The endpoint titer for each serum was determined by the last dilution that gave twice the signal of the background reading.

Competition antibody binding assay. A competition ELISA was used to determine epitope specificity, i.e., whether sera from vaccinated animals contain Abs recognizing epitopes similar to those well-characterized Env-specific mAbs PG9, CH58, 697-D, and 830A. Dilutions of sera were pre-incubated in wells of plates coated with antigens at a concentration of 1 µg/ml followed by incubation with a biotinylated PG9, CH58, 697-D, or 830A. Plates were washed with PBS containing 0.02% Tween 20 before incubation with a streptavidin-Sulfo tag reporter reagent. Plates were read at a wavelength of 450 nm. A reduction in signal reflects the presence of Abs in serum that competed with labeled mAbs for binding to the plate-bound antigen.

Neutralization Assays. For detection of neutralizing Abs (nAbs) in rabbit immune sera, clade C MW965.26 (tier 1A) and ZM109F.PB4 (tier 1B) pseudoviruses from the standard pseudovirus panels were used (Seaman et al., "Tiered Categorization of a Diverse Panel of HIV-1 Env Pseudoviruses for Assessment of Neutralizing Antibodies," *J. Virol.* 84:1439-1452 (2010), which is hereby incorporated by reference in its entirety). The standard TZM.b1 pseudovirus neutralization assay was performed (Seaman et al., "Tiered Categorization of a Diverse Panel of HIV-1 Env pseudoviruses for Assessment of Neutralizing Antibodies," *J. Virol.* 84:1439-1452 (2010); Li et al., "Human Immunodeficiency Virus Type 1 Env Clones From Acute And Early Subtype B Infections for Standardized Assessments of Vaccine-Elicited Neutralizing Antibodies," *J. Virol.* 79:10108-10125 (2005), which are hereby incorporated by reference in their entirety). Briefly, serial dilutions of heat-inactivated sera were prepared starting at a dilution of 1:10. The serum/pseudovirus mixtures were then incubated with the TZM.b1 target cells, and luciferase activity was measured 30 min or 24 hours later. Pools of pre-bleed sera were tested as negative controls against each pseudovirus, and all sera were also tested against a negative-control pseudovirus carrying the envelope of murine leukemia virus. The percent neutralization was calculated relative to the effect of the pre-immune serum from the same rabbit at the same dilution. All sera were assayed in duplicate in at least two experiments against each virus. The 50%, 80%, and 90% inhibitory dose titers were calculated as the serum dilution that caused these percentages of reduction in relative luminescence units compared to the level in the virus control wells.

Example 1

Design and Construction of Structurally Unconstrained and Constrained Immunogens Presenting V1V2 Epitope Types First, a couple of V1V2 immunogens mimicking the trimeric V1V2 conformation in the stabilized BG505 SOSIP.664 gp140 context (Sanders et al., "A Next-Generation Cleaved, Soluble HIV-1 Env Trimer, BG505 SOSIP.664 Gp140, Expresses Multiple Epitopes For Broadly Neutralizing But Not Non-Neutralizing Antibodies," *PLoS Pathog* 9:e1003618 (2013), which is hereby incorporated by reference in its entirety) were designed. The initial design was based on the structures then available: the low-resolution cryo-EM structure of BG505 SOSIP/PG9 complex and a 1.8 Å resolution crystal structure of a V1V2-1FD6 scaffold/PG9 complex (McLellan et al., "Structure of HIV-1 gp120 V1/V2 Domain With Broadly Neutralizing Antibody PG9," *Nature* 480:336-343 (2011); Julien et al., "Asymmetric Recognition of the HIV-1 Trimer By Broadly Neutralizing Antibody PG9," *Proc. Natl. Acad. Sci. USA* 110:4351-4356 (2013), which are hereby incorporated by reference in their entirety). The latter structure demonstrated that V1V2 could be grafted onto β-hairpins within another protein. The PDB was searched for homo-trimeric structures with exposed β-hairpins and suitable spatial parameters for scaffolding V1V2 (FIGS. 1A and 1B). It was identified that the trimer of the MRG15 chromo-domain (PDB ID 2F5K) has a β-hairpin that would accommodate V1V2 with the orientation present in the SOSIP trimer. A V1V2-scaffold immunogen based on these structures was designed, using the ZM53 sequence that has relatively short V1 and V2 hypervariable loops. The chimeric structure included the complete V1V2 domain with the terminal Cys126 and Cys196 of ZM53 fused at the match points to 2F5K, excluding the turn residues in the original scaffold hairpin; this immunogen is named V1V2(ZM53)-2F5K (see Table 1 below).

TABLE 1

Amino acid sequences of the rationally designed immunogens used in rabbit experiments H2 and H3.

| Name | Amino acid sequence |
|---|---|
| V1V2 (ZM53)-2F5K SEQ ID NO: 8 | PKPKFQEGERVLCFHGPLLYEAKCVKVAILAACVTLNCSKLNNATDGEMKNCSFNATT ELRDKKKQVYALFYKLDIVPLDGRNNSSEYRLINCEETVKYFIHYSGWNKNWDEWVPE SRVLKYVDTNLQKQRELQKANQEQYAEGKGLEVLFQGPGHHHHHHHHSAWSHPQFEK |
| V1V2 (ZM53)-2J9C SEQ ID NO: 9 | GSMKKVEAIIRPEKLEIVKKALSDAGYVGMTVSEVKGRGVQGGIVERYCVTLNCSKLN NATDGEMKNCSFNATTELRDKKKQVYALFYKLDIVPLDGRNNSSEYRLINCREYIVDL IPKVKIELVVKEEDVDNVIDIICENARTGDPGDGKIFVIPVERVVRVRTKEEGKEALL EHGLEVLFQGPGHHHHHHHHSAWSHPQFEK |
| V1V2 (ZM109)-TTB SEQ ID NO: 12 | EWTGDNTNAYYSDEVISELHVGQIDTSPYFCIKTVKANGAGTPVVACAVSKQSIWAPS FKELLDQARYFYSTGQSVRIHVQKNIWTYPLFVNTFSANALVGLSSCVKLTPLCVTLN CTSPAAHNESETRVKHCSFNITTDVKDRKQKVNATFYDLDIVPLSSSDNSSNSSLYRL ISCNTSTITQACFGPKLEVLFQGPGHHHHHHHHSAWSHPQFEK |
| V1V2 (ZM109)-1FD6-Fc SEQ ID NO: 22 | MTTFKLAACVTLNCTSPAAHNESETRVKHCSFNITTDVKDRKQKVNATFYDLDIVPLS SSDNSSNSSLYRLISCQTTTTEAVDAATAAKVFKQYANDNGIDGEWTYDDATKTFTVT EGLEVLFQGASGGSKPTCPPPELLGGPSVFIFPPKPKDTLMISRTPEVTCVVVDVSQD DPEVQFTWYINNEQVRTARPPLREQQFNSTIRVVSTLPIAHQDWLRGKEFKCKVHNKA LPAPIEKTISKARGQPLEPKVYTMGPPREELSSRSVSLTCMINGFYPSDISVEWEKNG KAEDNYKTTPAVLDSDGSYFLYSKLSVPTSEWQRGDVFTCSVMHEALHNHYTQKSISR SPGK |
| V1V2 (1086)-Fc SEQ ID NO: 23 | SLKPCVKLTPLCVTLNCTNVKGNESDTSEVMKNCSFKATTELKDKKHKVHALFYKLDV VPLNGNSSSSGEYRLINCNTSAITQACPKVSGASGGSKPTCPPPELLGGPSVFIFPPK PKDTLMISRTPEVTCVVVDVSQDDPEVQFTWYINNEQVRTARPPLREQQFNSTIRVVS |

TABLE 1-continued

Amino acid sequences of the rationally designed immunogens used in rabbit experiments H2 and H3.

| Name | Amino acid sequence |
|---|---|
| | TLPIAHQDWLRGKEFKCKVHNKALPAPIEKTISKARGQPLEPKVYTMGPPREELSSRS VSLTCMINGFYPSDISVEWEKNGKAEDNYKTTPAVLDSDGSYFLYSKLSVPTSEWQRG DVFTCSVMHEALHNHYTQKSISRSPGK |
| V1V2 (ZM109)-Fc SEQ ID NO: 24 | SLKPCVKLTPLCVTLNCTSPAAHNESETRVKHCSFNITTDVKDRKQKVNATFYDLDIV PLSSSDNSSNSSLYRLISCNTSTITQACPKVSGASGGSKPTCPPPELLGGPSVFIFPP KPKDTLMISRTPEVTCVVVDVSQDDPEVQFTWYINNEQVRTARPPLREQQFNSTIRVV STLPIAHQDWLRGKEFKCKVHNKALPAPIEKTISKARGQPLEPKVYTMGPPREELSSR SVSLTCMINGFYPSDISVEWEKNGKAEDNYKTTPAVLDSDGSYFLYSKLSVPTSEWQR GDVFTCSVMHEALHNHYTQKSISRSPGK |

Figures 2A, 2B, 2C, 2D:
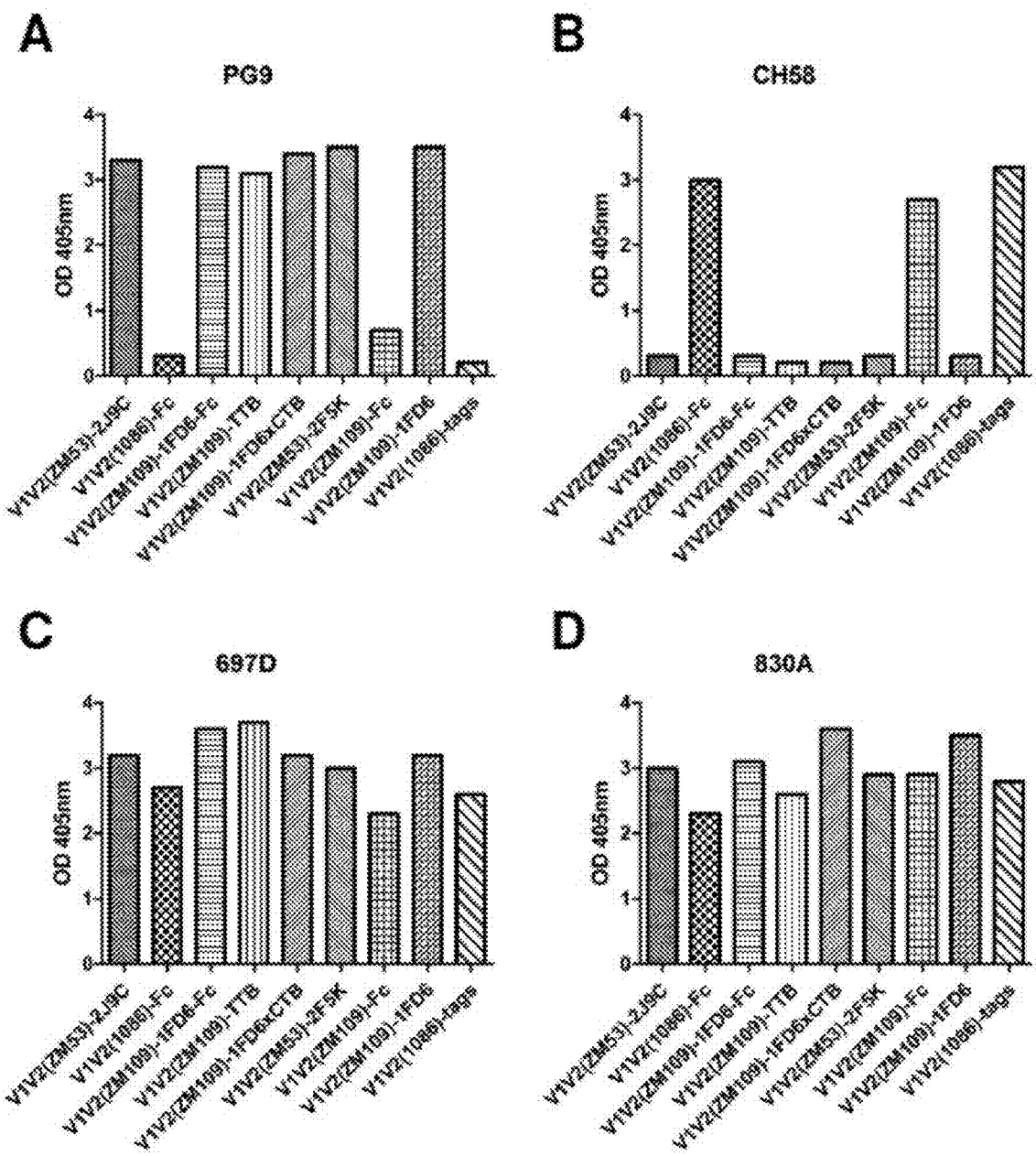
FIGS. 2A-2F show antigenicity tests of V1V2 immunogens. Binding of V1V2 immunogens to V2q mAb PG9 (FIG. 2A), V2p mAb CH58 (FIG. 2B), and V2i mAbs 697-D and 830A (FIGS. 2C and 2D) analyzed by ELISA is shown. Note that, in the top two panels, immunogens that bound well to the V2q mAb PG9 bind poorly to the V2p mAb CH58, and vice versa.
Figure 2E:
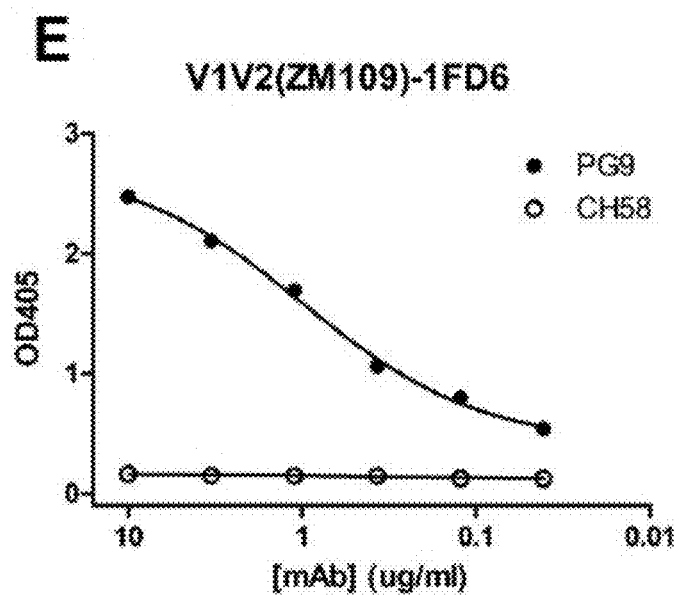
Figure 2F:
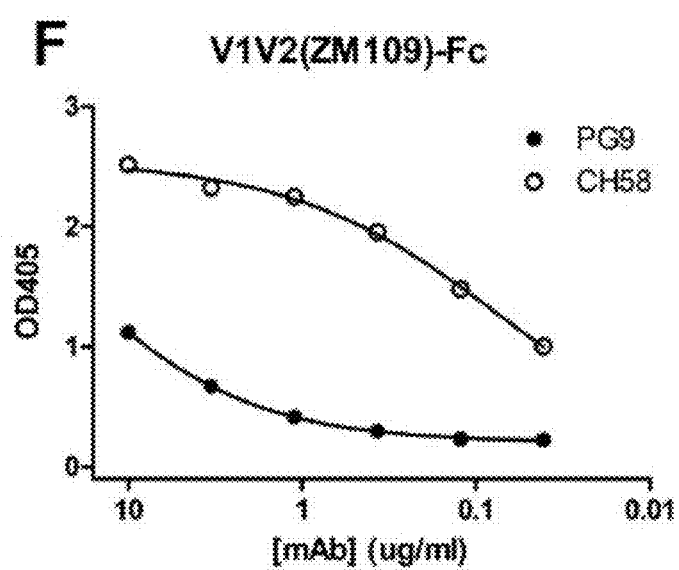

Meanwhile, a crystal structure of V1V2(ZM109)-1FD6 in complex with a V2i mAbs, 830A was determined, and revealed that the V1V2 domain can adopt a 5-strand β-barrel conformation (Pan et al., "The V1V2 Region of HIV-1 gp120 Forms a Five-Stranded Beta Barrel," *J. Virol.* 89:8003-8010 (2015), which is hereby incorporated by reference in its entirety) that is distinct from the 4-strand structure observed in complexes with mAbs PG9 and PG16 (McLellan et al., "Structure of HIV-1 gp120 V1/V2 Domain With Broadly Neutralizing Antibody PG9," *Nature* 480: 336-343 (2011); Pancera et al., "Structural Basis For Diverse N-Glycan Recognition by HIV-1-Neutralizing V1-V2-Directed Antibody PG16," *Nat. Struct. Mol. Biol.* 20:804-813 (2013), which are hereby incorporated by reference in their entirety). Remarkably, this change is accompanied by the bending of the V1V2 stem β-strands so that the tilt of the β-barrel with respect to the stem strands is different (FIG. 1B). Search of the PDB showed that the structure of the GlnK1 protein from *Methanococcus jannaschii* (PDB ID 2J9C) would be suitable for scaffolding this V1V2 conformation. Thus, another trimeric V1V2 scaffold V1V2 (ZM53)-2J9C (Table 1 and FIG. 1C) was constructed. These trimeric V1V2-scaffold proteins were produced in the HEK 293S GnTI-/- cells that produce only high-mannose glycans, which are more homogeneous than complex glycans (Reeves et al., "Structure and Function in Rhodopsin: High-Level Expression of Rhodopsin With Restricted and Homogeneous N-Glycosylation by a Tetracycline-Inducible N-Acetylglucosaminyltransferase I-Negative HEK293 S Stable Mammalian Cell Line," *Proc. Natl. Acad. Sci. USA* 99:13419-13424 (2002), which is hereby incorporated by reference in its entirety). Antigenicity tests showed that both V1V2(ZM53)-2F5K and V1V2(ZM53)-2J9C could bind PG9 as well as 697-D and 830A; thus they harbor V2q and V2i epitopes (FIG. 2A and Table 2).

TABLE 2

Types of epitopes carried by the immunogens and antigens used in this study.

| Antigen | V2q (Reactive with PG9) | V2i (Reactive with 697-D &/or 830A) | V2p (Reactive with CH58) |
|---|---|---|---|
| V1V2/ZM53-2J9C | + | + | − |
| V1V2/1086-Fc | − | + | + |
| V1V2/ZM109-1FD6-Fc | + | + | − |
| V1V2/ZM109-TTB | + | + | − |
| VlV2/ZM109-1FD6xCTB | + | + | − |
| V1V2/ZM53-2F5K | + | + | − |
| V1V2/ZM109-Fc | − | + | + |

TABLE 2-continued

Types of epitopes carried by the immunogens and antigens used in this study.

| Antigen | V2q (Reactive with PG9) | V2i (Reactive with 697-D &/or 830A) | V2p (Reactive with CH58) |
|---|---|---|---|
| V1V2/ZM109-1FD6 | + | + | − |
| V1V2/1086-tags | − | + | + |

As noted above, trimeric arrangement of V1V2 domains in V1V2(ZM53)-2F5K and V1V2(ZM53)-2J9C constructs was based on approximate geometry deduced from low-resolution electron microscopy structures. After the constructs were designed and entered experimental evaluation, high-resolution X-ray structures of SOSIP trimers became available (Pancera et al., "Structure and Immune Recognition of Trimeric Pre-Fusion HIV-1 Env," *Nature* 514:455-461 (2014); Julien et al., "Crystal Structure of a Soluble Cleaved HIV-1 Envelope Trimer," *Science* 342:1477-1483 (2013), which are hereby incorporated by reference in their entirety). The configurations of V1V2 domains in the construct models were compared with the SOSIP structure (PDB ID 4TVP). It was found that the positions of the center of mass of the V1V2 domains deviated by only 1.9 Å and 1.6 Å for 2F5K- and 2J9C-based constructs, respectively. The V1V2 domain was also rotated by 18° in the 2F5K-based construct, while in the 2J9C-based construct, rotation angle reached 96°. Thus, the 2F5K-based construct design is predicted to achieve a V1V2 domain configuration that is significantly closer to the native-like closed spike trimer state. It should be noted that the β-strands connecting the V1V2 domains to the scaffold are likely to be substantially flexible and therefore domain orientations are expected to sample a range of positions around the modeled one.

The scaffold molecule V1V2(ZM109)-1FD6 used in crystallization with PG9 and PG16 (McLellan et al., "Structure of HIV-1 gp120 V1/V2 Domain With Broadly Neutralizing Antibody PG9," *Nature* 480:336-343 (2011), which is hereby incorporated by reference in its entirety) naturally carries the V2q type of epitopes. However, the molecule is rather small (~25 kDa with glycans) and was not very immunogenic in rabbits (data not shown). Therefore, an effort was made to improve its immunogenicity by attaching at its C-terminus the rabbit Fc fragment. In the antigenicity test, this bivalent immunogen, V1V2(ZM109)-1FD6-Fc (Table 1), was able to bind PG9 as well as 697-D and 830A (FIGS. 2A, 2C-2D); thus this immunogen harbors the V2q and V2i epitopes (Table 2).

Two immunogens were also constructed based on pentameric bacterial toxin B subunits. Cholera toxin B subunit (CTB)-based immunogens carrying HIV-1 V3 epitopes had been previously tested and showed that they were highly immunogenic and elicited cross-clade neutralizing Ab responses in rabbits (Totrov et al., "Structure-Guided Design and Immunological Characterization Of Immunogens Presenting The HIV-1 Gp120 V3 Loop on a CTB Scaffold," *Virology* doi:S0042-6822(10)00409-5 [pii] (2010); Zolla-Pazner et al., "Focusing the Immune Response on the V3 Loop, A Neutralizing Epitope of the HIV-1 gp120 Envelope," *Virology* 372:233-246 (2008); Zolla-Pazner et al., "Cross-Clade HIV-1 Neutralizing Antibodies Induced With V3-Scaffold Protein Immunogens Following Priming With gp120 DNA," *Journal of Virology* 85:9887-9898 (2011), which are hereby incorporated by reference in their entirety). To test CTB's effects on V1V2 immunogens, the structurally constrained V1V1(ZM109)-1FD6 was chemically conjugated with CTB and showed that it preserved the V2q and V2i epitopes in the V1V2 scaffold (FIGS. 2A, 2C-2D). A V1V2-typhoid toxin B subunit (TTB) fusion protein V1V2 (ZM109)-TTB (Table 1) was also created, taking advantage of the fact that TTB harbors a disulfide bond near its C-terminus which is a naturally suitable place for grafting the disulfide linked V1V2 domain (PDB ID 4K6L; FIG. 1D). Computer modeling showed that the pentameric TTB can host five copies of V1V2 without any structural hindrances (FIG. 1D). Interestingly, V1V2(ZM109)-TTB harbors the structurally constrained V2q and V2i epitopes (FIGS. 2A, 2C-2D) although its pentameric form does not resemble in any way that of V1V2 in the gp120 trimer.

To construct structurally unconstrained V1V2 molecules, the V1V2 domains of clade C strains 1086 or ZM109 were fused to rabbit Fc (Table 1). Since only the C-terminus of the V1V2 (post the V1V2 disulfide bond) is linked to the flexible N-terminus of Fc, there are no constraints imposed on the V1V2 β-hairpin stem. Indeed, antigenicity tests showed that V1V2(1086)-Fc and V1V2(ZM109)-Fc were recognized by the V2p mAb CH58 but not by V2q mAb PG9 (FIGS. 2A, 2B, 2E, and 2F); thus these unconstrained V1V2 harbor the V2p epitopes (Table 2).

These data describe a panel of immunogens that can present the V2q, V2p and V2i epitopes (Tables 1 and 2). The V2q epitopes can only be presented by the immunogens with structurally constrained V1V2s, while the V2p epitopes can only be presented by the immunogens with unconstrained V1V2s. In contrast, V2i epitopes can be presented by immunogens with either constrained or unconstrained V1V2s.

Example 2

DNA Prime-Protein Boost Regimen Using Rationally Designed Immunogens Elicited Strong Ab Responses Targeting Gp120 V1V2

To test the immunogenicity of the immunogens, two rabbit experiments, H2 and H3, were carried out (see Table 3 below).

TABLE 3

The design of rabbit studies H2 and H3.

| Study group | No. of rabbits | Rabbit #s | Prime* | Boosts** |
|---|---|---|---|---|
| H2.1 | 3 | H2.1.1-3 | gp120.ZM109 DNA | gp120(ZM109) |
| H2.2 | 4 | H2.2.1-4 | | V1V2(ZM53)-2J9C |
| H2.3 | 4 | H2.3.1-4 | | V1V2(1086)-Fc |
| H2.4 | 5 | H2.4.1-5 | | V1V2(ZM109)-1FD6-Fc |
| H2.5 | 5 | H2.5.1-5 | | V1V2(ZM109)-TTB |
| H2.6 | 4 | H2.6.1-4 | | V1V2(ZM109)-1FD6 x CTB |
| H3.1 | 5 | H3.1.1-5 | gp120.ZM109 DNA | V1V2(ZM53)-2F5K |
| H3.2 | 5 | H3.2.1-5 | | V1V2(ZM109)-1FD6-Fc |
| H3.3 | 5 | H3.3.1-5 | | V1V2(ZM109)-Fc |
| H3.4 | 5 | H3.4.1-5 | gp120.ZM109 DNA + V1V2(ZM53)-2J9C | V1V2(ZM53)-2J9C |
| H3.5 | 5*** | H3.5.1-3, 5 | gp120.ZM109 DNA + V1V2(ZM109)-TTB | V1V2(ZM109)-TTB |

*For the priming immunizations, the codon optimized gp120.ZM109 DNA vaccine (36 mg/dose, 1 mg/shot) was delivered by gene gun at Weeks 0, 2 and 4, in all groups. In Groups H3.4 and H3.5, the rabbits also received V1V2 scaffold protein boosts (100 mg/dose) formulated with IFA adjuvant by intramuscular (IM) route at the same time of DNA immunization as indicated.
**For the boosting immunizations, the individual V1V2 scaffold protein (100 mg/dose) formulated with IFA adjuvant was administered by IM.
***One animal (#4) had to be terminated early due to health issues.

In rabbit experiment H2, six immunogens were tested, including the gp120(ZM109) monomer (rabbit group H2.1), the trimeric, structurally constrained V1V2(ZM53)-2J9C (H2.2), the structurally unconstrained V1V2(1086)-Fc (H2.3), the structurally constrained V1V2(ZM109)-1FD6-Fc (H2.4), the pentameric, structurally constrained toxin subunit B-based V1V1(ZM109)-TTB (H2.5) and the structurally constrained cross-linked construct V1V2(ZM109)-1FD6×CTB (H2.6). In this experiment, a DNA prime/protein boost regimen was used (with three consecutive DNA primes followed by three protein boosts) that that was previously successful in inducing Ab responses in rabbits (Zolla-Pazner et al., "Focusing the Immune Response on the V3 Loop, a Neutralizing Epitope of the HIV-1 gp120 Envelope," *Virology* 372:233-246 (2008); Zolla-Pazner et al., "Cross-Clade HIV-1 Neutralizing Antibodies Induced With V3-Scaffold Protein Immunogens Following Priming with gp120 DNA," *Journal of Virology* 85:9887-9898 (2011); Wang et al., "Polyvalent HIV-1 Env Vaccine Formulations Delivered by the DNA Priming Plus Protein Boosting Approach Are Effective in Generating Neutralizing Antibodies Against Primary Human Immunodeficiency Virus Type 1 Isolates From Subtypes A, B, C, D and E," *Virology* 350:34-47 (2006), which are hereby incorporated by reference in their entirety). The DNA prime was a plasmid DNA encoding monomeric gp120(ZM109). In experiment H3 (Table 3), another trimeric immunogen V1V2(ZM53)-2F5K (group H3.1) was tested, and the structurally constrained V1V2(ZM109)-1FD6-Fc (H3.2) was repeated in comparison with an immunogen with the same V1V2 sequence but structurally unconstrained V1V2(ZM109)-Fc (H3.3). In addition, a new regimen in which animals were primed with the DNA as well as the protein (Table 3) (Pissani et al., "Improvement of Antibody Responses by HIV Envelope DNA and Protein Co-Immunization," *Vaccine* 32:507-513 (2014), which is hereby incorporated by reference in its entirety) was tested, using DNA and two protein immunogens were tested in the rabbit H2 experiment, V1V2(ZM53)-2J9C (H3.4) and V1V2(ZM109)-TTB (H3.5). The priming was then followed by two protein boosts with the same protein immunogen.

Figures 3A, 3B, 3C:
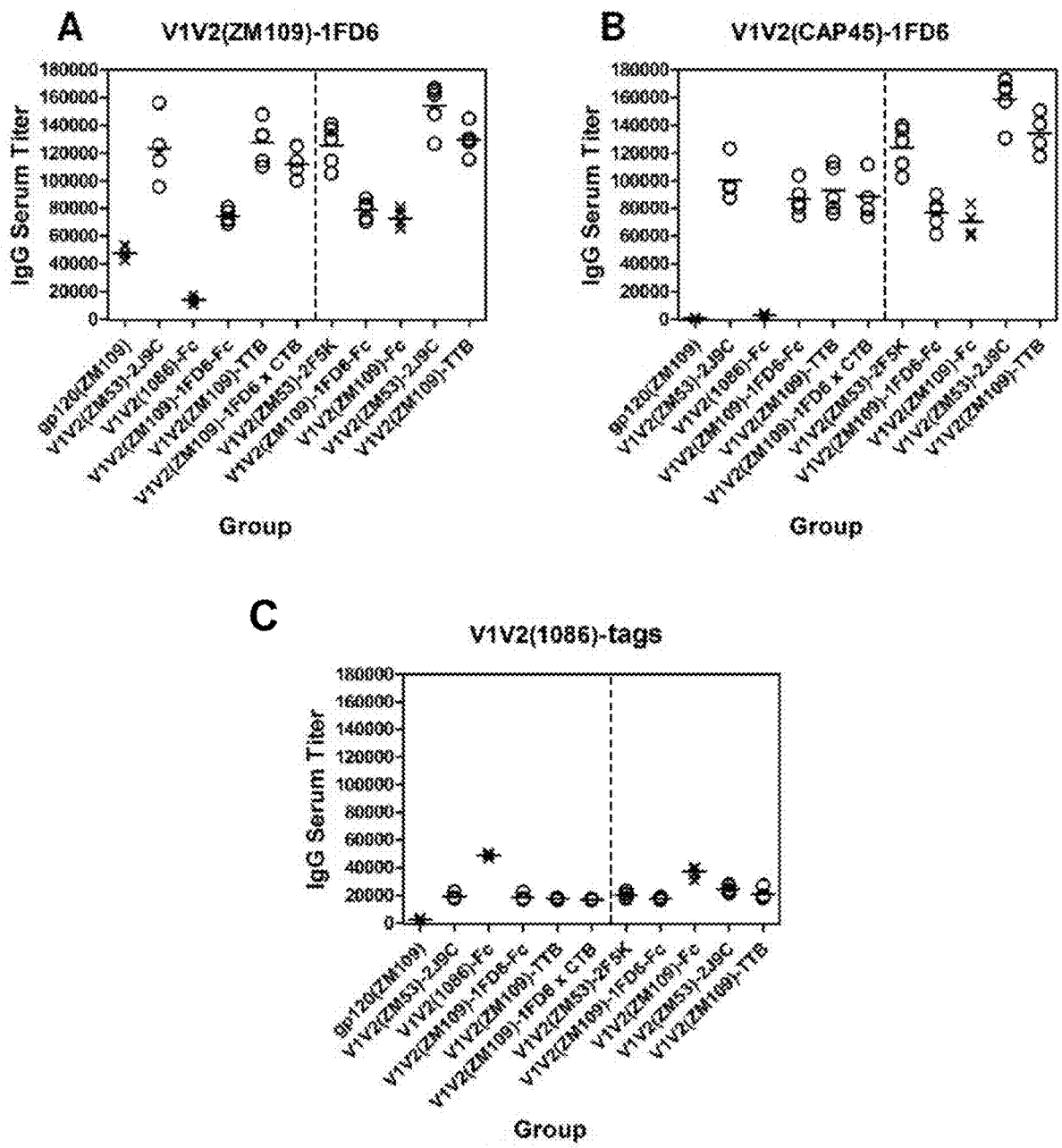
FIGS. 3A-3C show end point titers of the rabbit Ab responses to the V1V2 immunogens. Endpoint binding titers of sera for all the H2 and H3 rabbits measured by ELISA against the structurally constrained V1V2(ZM109)-1FD6 (FIG. 3A), V1V2(CAP45)-1FD6 (FIG. 3B) and the unconstrained V1V1(1086)-tags (FIG. 3C) are shown. Each point represents the average titer calculated from duplicate samples of individual rabbits. The data points of sera from animals immunized with structurally unconstrained immunogens are marked by crosses while that with the constrained immunogens by open circles. The vertical dashed line in each panel separates the H2 and H3 animal groups.
Figures 4A, 4B, 4C, 4D:
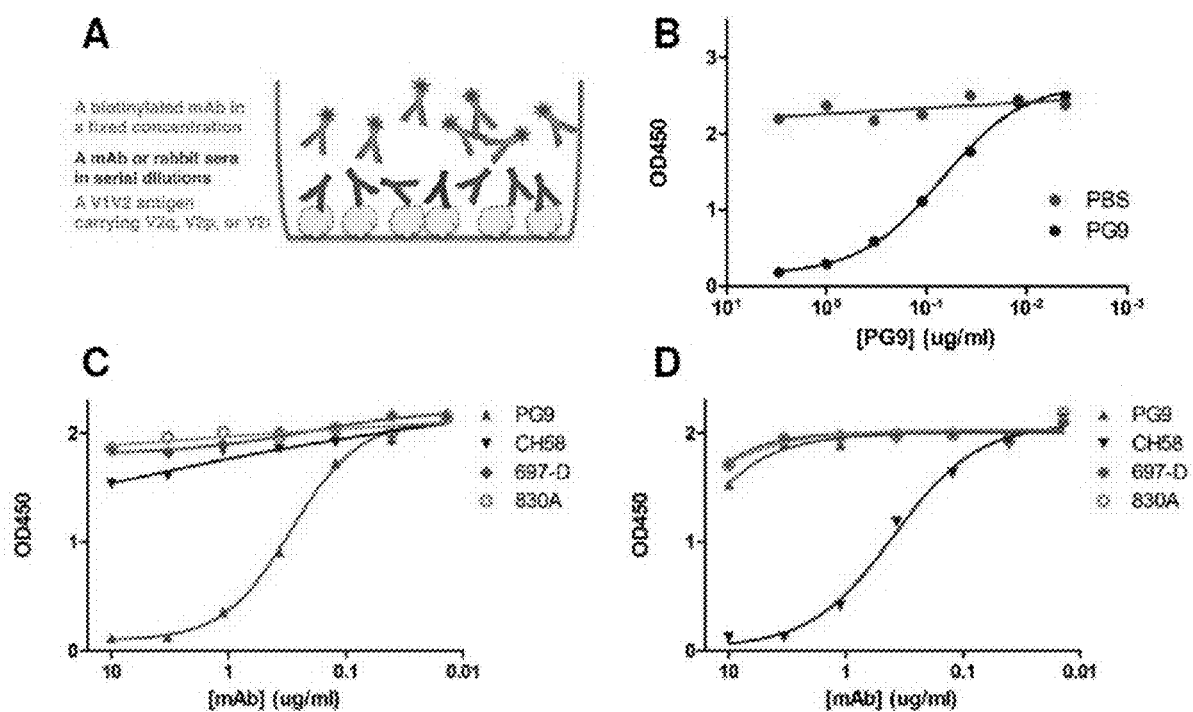
FIGS. 4A-4F show competition of V1V2 mAbs against each other.
Figure 4E:
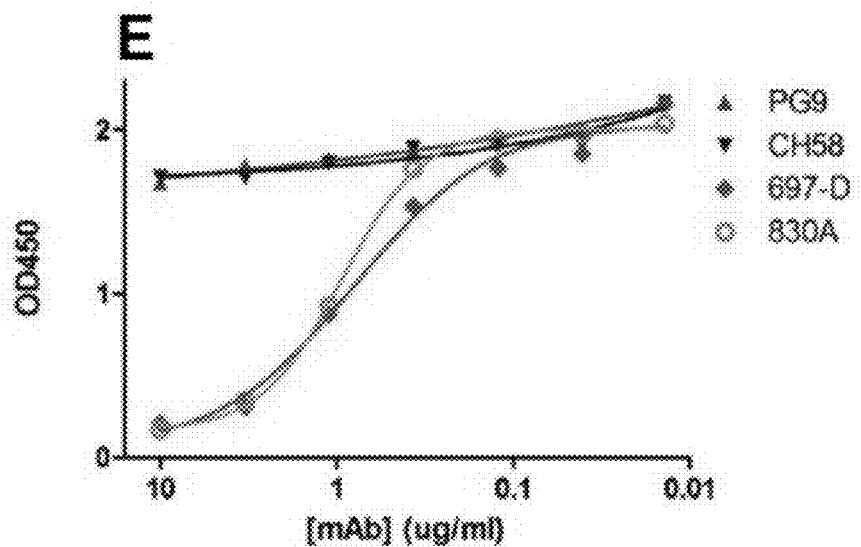
Figure 4F:
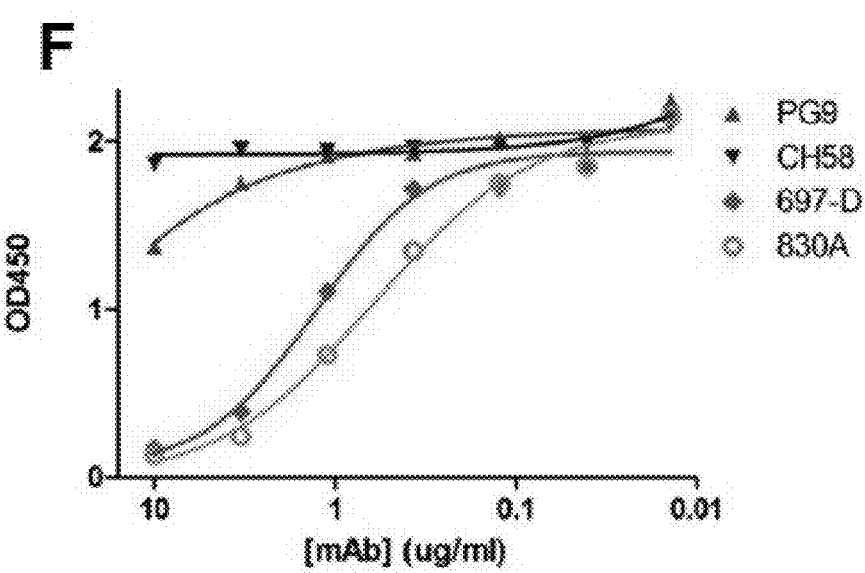

Sera from the animals for both H2 and H3 experiments displayed strong and distinct Ab responses to the immunogens as assessed by ELISA. To detect the Ab responses three V1V2 antigen probes were used, including the structurally constrained V1V2(ZM109)-1FD6 (FIG. 3A) and V1V2 (CAP45)-1FD6 (FIG. 3B), which had been used in complex with PG9 and PG16 for crystallization (McLellan et al., "Structure of HIV-1 gp120 V1N2 Domain With Broadly Neutralizing Antibody PG9," Nature 480:336-343 (2011), which is hereby incorporated by reference in its entirety), as well as the unconstrained V1V2(1086)-tags (FIG. 3C) (Liao et al., "Vaccine Induction of Antibodies Against a Structurally Heterogeneous Site of Immune Pressure Within HIV-1 Envelope Protein Variable Regions 1 and 2," Immunity 38:176-186 (2013), which is hereby incorporated by reference in its entirety). All three antigens used in ELISA carried V1V2 regions derived from clade C viruses but their sequences differ. The Ab responses clearly separated into two distinct groups based on their ELISA binding to the structurally constrained probes (FIGS. 3A and 3B) and the unconstrained probe (FIG. 3C). Thus the structurally constrained V1V2 immunogens induced strong Ab responses reactive with the structurally constrained antigen probes V1V2(ZM109)-1FD6 and V1V2(CAP45)-1FD6, while the unconstrained immunogens, V1V2(1086)-Fc and V1V2(ZM109)-Fc, were the only immunogens that induced Abs recognized, but weaker, by the unconstrained antigen V1V2 (1086)-tags. Although Ab responses induced by gp120 (ZM109) induced Abs that could recognize V1V2(ZM109)-1FD6, its binding was reduced against the heterologous V1V2(CAP45)-1FD6 probe, suggesting that gp120(ZM109) induced more sequence-specific Ab responses. Interestingly, in experiment H3, the structurally unconstrained V1V2 (ZM109)-Fc was able to induce strong Ab responses against the constrained scaffolded V1V2 probes, substantially different from the results of the V1V2(1086)-Fc in experiment H2 (FIGS. 3A and 3B). However, the epitope specificity of the Ab responses induced by the structurally unconstrained V1V2(ZM109)-Fc was different from the constrained V1V2 (ZM109)-1FD6-Fc as revealed by the competition assay (see below).

Example 3

Figures 5A, 5B, 5C, 5D:
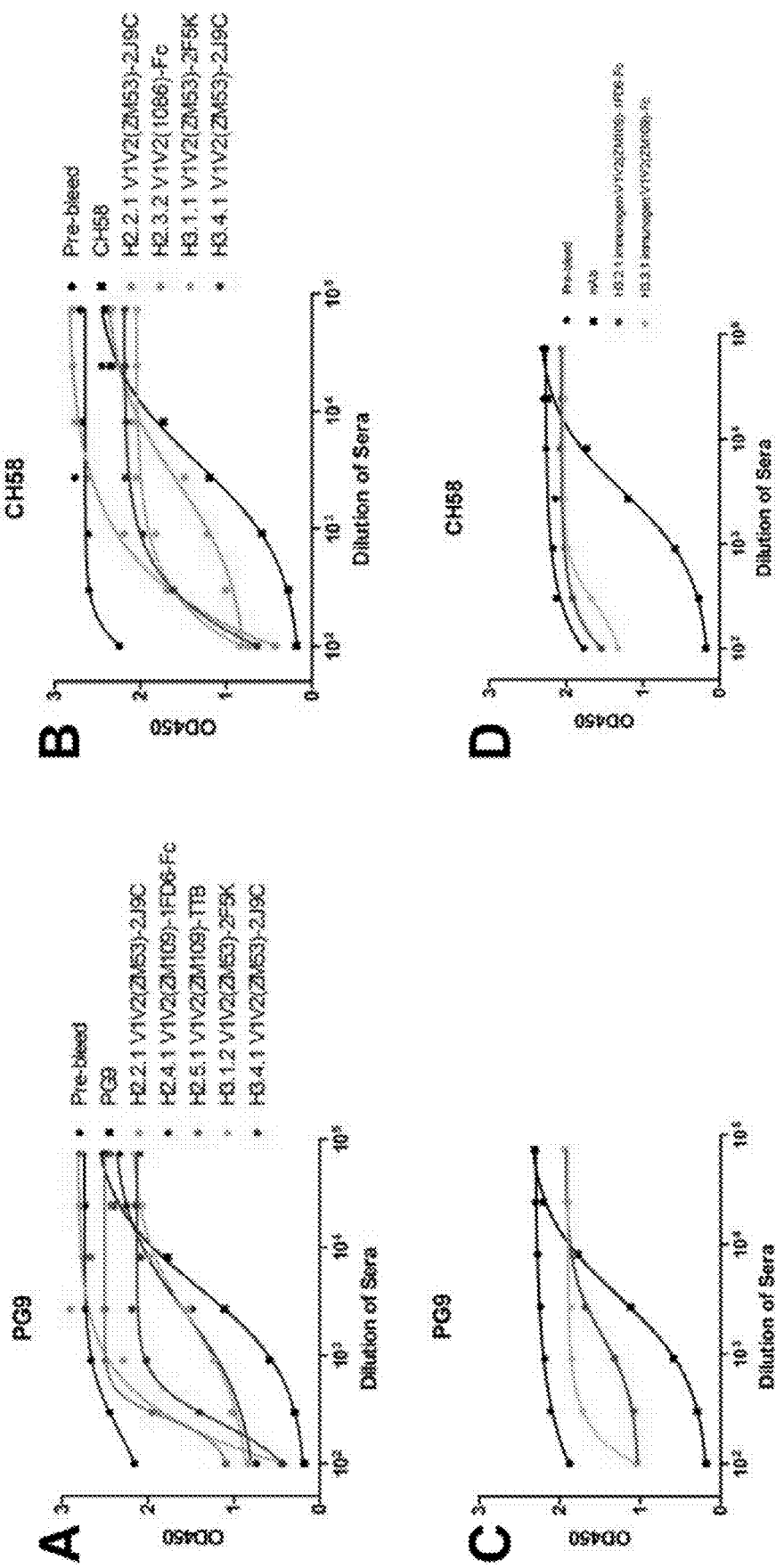
FIGS. 5A-5D show competition of rabbit sera against V1V2 mAbs.

V1V2-Scaffold Immunogens Induce Distinct Conformation-Specific V1V2-Directed Ab Responses To gain additional understandings of the conformational-specificities of the Ab responses induced by V1V2-scaffold immunogens in rabbit, an Ab competition assay was performed for the rabbit immune sera with the V2q mAb PG9, V2p mAb CH58, and V2i mAbs 697-D and 830A (FIGS. 4A-4F and 5A-5D). In this assay, the plates were coated with antigen probes that carry different epitope types and competed the rabbit sera with biotinylated mAbs. These representative V1V2 mAbs were used first to compete against each other (FIGS. 4A-4F). The data showed that only the two V2i mAbs, 697-D and 830A, competed against each other, further illustrating the distinctness of the three types of V1V2 epitopes. Rabbit sera taken two weeks after the last protein boost were then used to against each V1V2 mAbs (FIGS. 5A-5D). Sera from rabbit groups immunized by the structurally constrained immunogens V1V2(ZM53)-2J9C (FIG. 5A; represented by rabbit numbers H2.2.1 and H3.4.1), V1V2(ZM109)-TTB (FIG. 5A; H2.5.1), and V1V2 (ZM109)-1FD6-Fc (FIG. 5A; H2.4.1) showed pronounced competition against PG9 for the binding of V1V2(ZM109)-1FD6, suggesting that these immunogens induced Abs whose epitopes overlap, and conformationally similar to, the V2q epitopes. On the other hand, sera from rabbits of the group immunized with V1V2(1086)-Fc (H2.3.2) competed well with the V2p mAb CH58 for binding to V1V2(1086)-tags. Interestingly, sera from rabbits immunized with the trimeric immunogens V1V2(ZM53)-2J9C (FIG. 5B; H2.2.1 and H3.4.1) and V1V2(ZM53)-2F5K (FIG. 5B; H3.1.1) could also compete with CH58 with modest strength. By contrast, no sera gave very strong competition against the V2i mAbs 697-D and 830A (not shown). FIGS. 5C and 5D illustrated the difference of Abs induced by the two immunogens V1V2(ZM109)-1FD6-Fc and V1V2(ZM109)-Fc that have the same V1V2 sequence. The structurally constrained V1V2(ZM109)-1FD6-Fc clearly induced Abs that could compete strongly with PG9, while that induced by the unconstrained V1V2(ZM109)-Fc could compete very little (FIG. 5C). Interestingly V1V2(ZM109)-Fc (FIG. 5D) did not induce Abs that can compete strongly with CH58, different from that of V1V2(1086)-Fc (FIG. 5B; H2.3.2).

Example 4

V1V2 Immunogen-Induced Antibody Neutralization

Figures 6A, 6B:
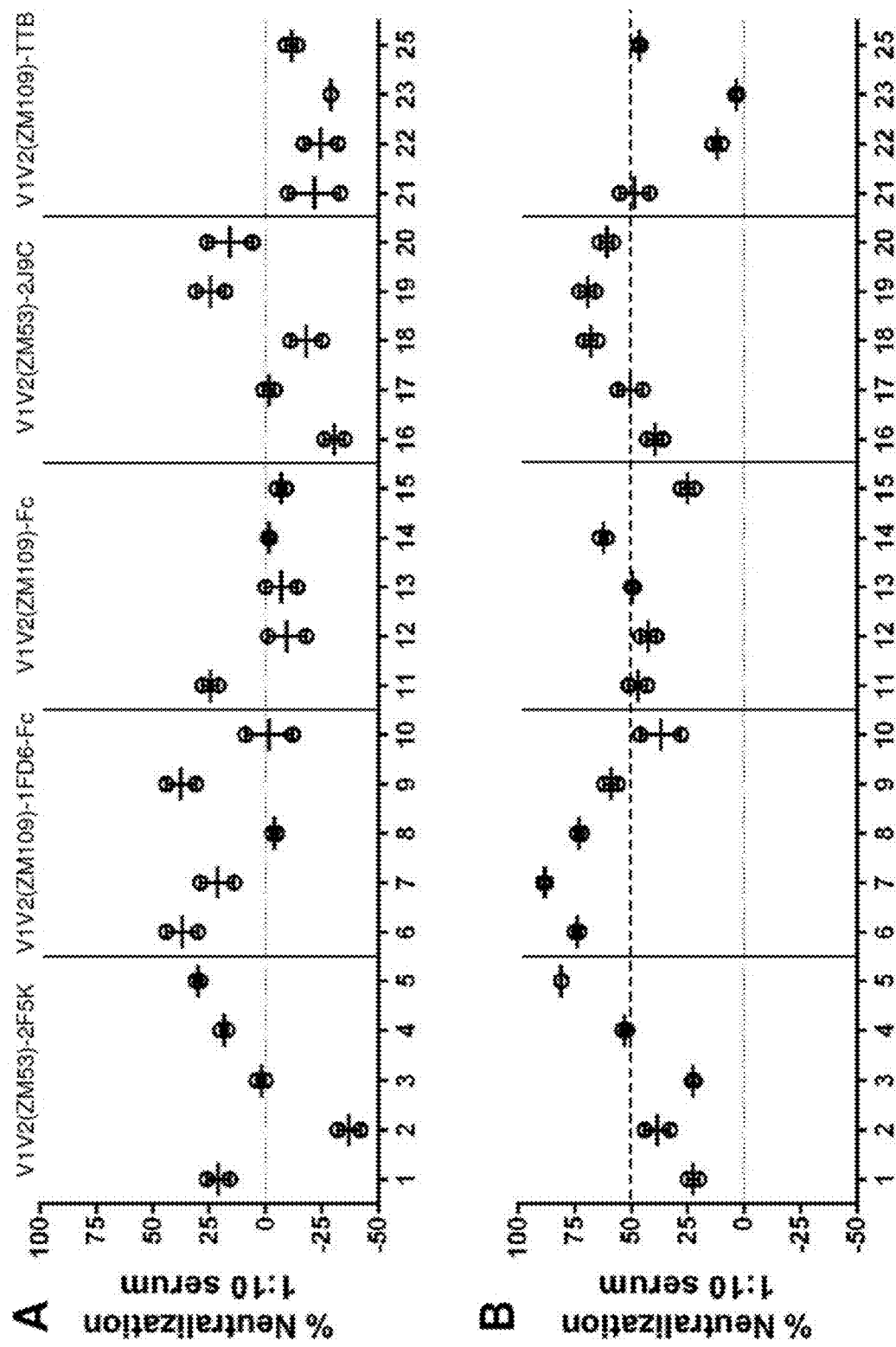
FIGS. 6A-6B show results of neutralization assays.

The neutralizing activity of all immune sera from experiment H3 was assessed using the TZM.b1 assay under conditions in which the virus and sera were incubated together for either 30 min or 24 hours prior to addition to cells, as per previous studies (Upadhyay et al., "Distinct Mechanisms Regulate Exposure of Neutralizing Epitopes in the V2 and V3 Loops of HIV-1 Envelope," J. Virol. 88:12853-12865 (2014), which is hereby incorporated by reference in its entirety); the pseudoviruses of strains MW965 and ZM109 were used (Table 4 (FIG. 6C) and FIGS. 6A-B, respectively).

Although strains MW965 (tier 1A) and ZM109 (tier 1B) are neutralization sensitive viruses, they could not be neutralized by the RV144 V2p mAb CH58 (data not shown). Sera drawn two weeks after the last boost from almost all animals achieved neutralization of 93MW965 in the 30 min assay while all sera achieved 50% neutralization in the 24 hours assay (Table 4, FIG. 6C). In assays using the tier 1B strain ZM109 (FIGS. 6A-6B), in the 24 hours assay, sera from four of the five groups in experiment H3, boosted with the structurally constrained V1V2(ZM109)-1FD6-Fc or V1V2(ZM53)-2J9C gave >50% neutralization (above the dashed line in FIG. 6B). Since the V1V2 sequence of V1V2(ZM53)-2J9C used in immunizing group H3.4 is different from that of ZM109, the immune sera of this group achieve heterologous neutralization in the 24 hour assay. Sera from two animals immunized with another trimeric V1V2(ZM53)-2F5K also achieved heterologous neutralization of ZM109 in the 24 hour assay.

Discussion of Examples 1-4

Data from the RV144 phase III vaccine trial, the only HIV/AIDS vaccine trial that demonstrated modest 31.2% efficacy, suggested that the V1V2 region of HIV-1 gp120 is a key vaccine target (Rerks-Ngarm et al., "Vaccination With ALVAC and AIDSVAX to Prevent HIV-1 Infection in Thailand," N. Engl. J. Med. 361:2209-2220 (2009); Haynes et al., "Immune-Correlates Analysis of an HIV-1 Vaccine Efficacy Trial," *The New England Journal of Medicine* 366:1275-1286 (2012); Zolla-Pazner et al., "Vaccine-Induced IgG Antibodies to V1V2 Regions of Multiple HIV-1 Subtypes Correlate With Decreased Risk of HIV-1 Infection," *PLoS One* 9:e87572 (2014); Zolla-Pazner et al., "Analysis of V2 Antibody Responses Induced in Vaccinees in the ALVAC/AIDSVAX HIV-1 Vaccine Efficacy Trial," *PLoS One* 8:e53629 (2013), which are hereby incorporated by reference in their entirety). Clearly, a more efficacious vaccine is needed. By data of mAbs isolated from an RV144 vaccinee, it is known that V2p Abs were induced (Liao et al., "Vaccine Induction of Antibodies Against a Structurally Heterogeneous Site of Immune Pressure within HIV-1 Envelope Protein Variable Regions 1 And 2," *Immunity* 38:176-186 (2013), which is hereby incorporated by reference in its entirety). However, the absence of strong neutralizing activity in RV144 sera suggests that V2q Abs were not induced (Montefiori et al., "Magnitude and Breadth of the Neutralizing Antibody Response in The RV144 and Vax003 HIV-1 Vaccine Efficacy Trials," *J. Infect. Dis.* 206:431-441 (2012), which is hereby incorporated by reference in its entirety). Which, if any of these types of V2 Abs were directly responsible for the reduced rate of infection is not known at this point. However, the classification of V1V2 epitopes into three distinct types, i.e. the V2q, V2p and V2i types, provided a conceptual framework for designing immunogens that can focus the immune responses to each of these types (Mayr et al., "Epitope Mapping of Conformational V2-Specific Anti-HIV Human Monoclonal Antibodies Reveals an Immunodominant Site in V2," *PLoS One* 8:e70859 (2013); Spurrier et al., "Functional Implications of the Binding Mode of a Human Conformation-Dependent V2 Monoclonal Antibody Against HIV," *J. Virol.* 88:4100-4112 (2014), which are hereby incorporated by reference in their entirety).

Structural studies of V1V2 and the mAbs that bind to V2p/V2q epitope region have illuminated the structural complexity of this region, indicating that it can assume at least two conformation: one which is recognized by V2p mAbs in which the strand C region assumes a helical conformation—which appears to be present in molecules in which V1V2 is not constrained, such as V1V2(1086)-tags (FIG. 2B) (Liao et al., "Vaccine Induction of Antibodies Against a Structurally Heterogeneous Site of Immune Pressure Within HIV-1 Envelope Protein Variable Regions 1 And 2," *Immunity* 38:176-186 (2013), which is hereby incorporated by reference in its entirety), and alternatively, one recognized by V2q mAbs, in which the region is present as a β-strand, as in the case of molecules where V1V2 is constrained, such as V1V2(ZM109)-1FD6 and V1V2 (CAP45)-1FD6 (McLellan et al., "Structure of HIV-1 gp120 V1/V2 Domain with Broadly Neutralizing Antibody PG9," *Nature* 480:336-343 (2011); Pancera et al., "Structural Basis for Diverse N-Glycan Recognition by HIV-1-Neutralizing V1-V2-Directed Antibody PG16," *Nat. Struct. Mol. Biol.* 20:804-813 (2013), which are hereby incorporated by reference in their entirety). However, the V2i epitopes do not overlap with V2p and V2p epitopes (FIG. 4) (Pan et al., "The V1V2 Region of HIV-1 gp120 Forms a Five-Stranded Beta Barrel," *J. Virol.* 89:8003-8010 (2015), which is hereby incorporated by reference in its entirety), and V2i Abs can recognize V1V2 constructs harboring both conformations (Table 2).

It has been shown here that immunogens can be designed targeting the helical V2p and β-stranded V2q epitope types. In particular the structurally constrained V1V2-scaffold proteins such as the trimeric V1V2(ZM53)-2J9C and V1V2 (ZM53)-2F5K and the pentameric V1V2(ZM109)-TTB harbor the constrained helical conformation while the simple Fc-fusion forms of V1V2 carry the structurally unconstrained β-stranded conformation of the epitopes. These epitope scaffold immunogens can induce distinct Ab responses in rabbits, i.e., the Abs induced by the unconstrained immunogens induced Abs that reacted preferentially with the unconstrained V1V2 antigen V1V2(1086)-tags, while the constrained immunogens induced Abs that reacted preferentially with the constrained immunogens V1V2(ZM109)-1FD6 and V1V2(CAP45)-1FD6) (FIGS. 3A-3C). Moreover, the Abs induced by the immunogens carrying the V2q epitopes were able to compete with the V2q mAbs PG9 while that induced by the immunogens carrying the V2p epitopes were able to compete with the V2p mAbs CH58. In addition, sera of several rabbits could neutralize the tier 1A virus MW965, which is heterologous to the immunizing strains, and tier 1B virus ZM109 in the 24 hours incubation assay—a significant improvement from the V1V2 Abs induced by the RV144 vaccines.

These rabbit experiments are a first example that the immune response can be focused on the hypervariable V1V2 region. The cross-reactivity of human V1V2 Abs has long been established though this region has the most sequence and length diversity in the HIV-1 Env (Israel et al., "Prevalence of a V2 Epitope in Clade B Primary Isolates and Its Recognition by Sera from HIV-1-Infected Individuals," *AIDS* 11:128-130 (1997), which is hereby incorporated by reference in its entirety). This immunologic cross-reactivity in the face of variable amino acid sequences as well as insertions and deletions can be explained on the structural data that has emerged in the last few years. Thus, the β-barrel structure that have been described for V1V2 likely forms a conserved functional module (Pan et al., "The V1V2 Region of HIV-1 gp120 Forms a Five-Stranded Beta Barrel," *J. Virol.* 89:8003-8010 (2015), which is hereby incorporated by reference in its entirety), which not only explains the conserved antigenic structure that allows for antigenic cross-reactivity, but also allows the transplantation of the whole domain into scaffolds by rational structural designs.

The Ab response to V1V2 in HIV-infected individuals is less robust than that to V3 or the CD4-binding site (Israel et al., "Prevalence of a V2 Epitope in Clade B Primary Isolates and Its Recognition by Sera from HIV-1-Infected Individuals," *AIDS* 11:128-130 (1997); Kayman et al., "Presentation of Native Epitopes in the V1/V2 and V3 Regions of Human Immunodeficiency Virus Type 1 gp120 by Fusion Glycoproteins Containing Isolated gp120 Domains," *J. Virol.* 68:400-410 (1994); McKeating et al., "Immunogenicity of Full Length and Truncated Forms of the Human Immunodeficiency Virus Type I Envelope Glycoprotein," *Immunol. Lett.* 51:101-105 (1996), which are hereby incorporated by reference in their entirety), and V1V2 Ab responses were of a much smaller magnitude in previous vaccine studies than in RV144, suggesting that despite its prominent location on the Env spike, V1V2 is not an immunodominant epitope region. It has been shown in the data presented here that presenting V1V2 in a multivalent scaffold overcomes its relatively poor immunogenicity as well as inducing cross-reactive Abs. To induce even higher levels of Abs, these constructs can be readily modified to form nanoparticles, such as virus-like particles, which will present the V1V2 domain at even higher valencies capable of improved interaction with B cell receptors. These studies are currently on-going.

The data further demonstrate that one can selectively focus the Ab response on particular conformations of an epitope region. The helical conformation of the V2p epitope is likely a means of masking of the vulnerable β-strand conformation of the same region. Side chains of a helix point away from the helix axis, and helix-specific Abs are generally side chain-specific. From the point of view of the virus, helix-specific Abs would be preferential since virus escape by mutation from such Abs would be relatively simple. Escape from a complex conformational epitope, such as those targeted by V2q and V2i Abs, would be more complicated. The distinct characteristics of the Abs induced by structurally constrained immunogens and those induced by the unconstrained ones (FIGS. 3A-3C) suggest that the rabbit immune system responded differently against the two types of immunogens.

Data presented here suggest that these immunogens could serve as prototype vaccine candidates targeting the V1V2. While novel in the current iterations, improvements could induce Abs that are more V2q-like. For example, trimer specific mAbs like PGT145 were shown to bind close to the axis of the Env trimer and their epitopes are likely V1V2 specific (Sok et al., "Recombinant HIV Envelope Trimer Selects For Quaternary-Dependent Antibodies Targeting The Trimer Apex," *Proc Natl Acad Sci USA* 111:17624-17629 (2014), which is hereby incorporated by reference in its entirety). However, the two trimeric immunogens were not recognized by PGT145 (data not shown). However, since the trimeric scaffolds are recognized by PG9, the C strand of the V1V2 apex is likely correctly formed; however, their orientation toward the trimer axis may deviate from the right epitope of PGT145. Such orientation can be adjusted at the V1V2/scaffold junction, and computational modeling in combination with antigenicity testing will be able to identify improved constructs. In addition, the different functional activity of V1V2(ZM109)-Fc and V1V2(1086)-Fc suggested that the amino acid sequence of V1V2 can also play a role in their function. Sequence selection is another area for potential improvement, with attention paid to both amino acid sequence and variable loop lengths. It is anticipated that a combination of sequence selection, structure-based design and formulation as highly multivalent constructs will likely lead to V1V2 immunogens with superior ability to focus the Ab response on this site of vulnerability and with increased immunogenicity.

Materials and Methods for Examples 5-9

Use of a codon-optimized HIV env DNA, recombinant V1V2-scaffold proteins, and various protein and peptide antigens. Codon-optimized gp120 DNA expressing Env from HIV clade C primary isolate ZM109F (Li et al., "Genetic and Neutralization Properties of Subtype C Human Immunodeficiency Virus Type 1 Molecular Env Clones From Acute and Early Heterosexually Acquired Infections in Southern Africa," *J. Virol.* 80:11776-11790 (2006), which is hereby incorporated by reference in its entirety) was prepared in the pJW4303 vector with a tPA leader sequence as described previously (Wang et al., "Relative Contributions of Codon Usage, Promoter Efficiency and Leader Sequence to the Antigen Expression and Immunogenicity of HIV-1 Env DNA Vaccine," *Vaccine* 24:4531-4540 (2006); Zolla-Pazner et al., "Focusing the Immune Response on the V3 Loop, a Neutralizing Epitope of the HIV-1 gp120 Envelope," *Virology* 372:233246 (2008), which are hereby incorporated by reference in their entirety). The genes of the following proteins were used to prepare the scaffolds of the V1V2-scaffold immunogens: 1FD6 (Ross et al., "Designed Protein G Core Variants Fold to Native-Like Structures: Sequence Selection by ORBIT Tolerates Variation in Backbone Specification," *Protein Sci.* 10:450-454 (2001), which is hereby incorporated by reference in its entirety), typhoid toxin subunit B (TTB) (Song et al., "Structure and Function of the *Salmonella Typhi* Chimaeric A(2)B(5) Typhoid Toxin," *Nature* 499:350-354 (2013), which is hereby incorporated by reference in its entirety), 2J9C (Yildiz et al., "Structure of GlnK1 With Bound Effectors Indicates Regulatory Mechanism for Ammonia Uptake," *EMBO J.* 26:589-599 (2007), which is hereby incorporated by reference in its entirety), and 2F5K (Zhang et al., "Structure of Human MRG15 Chromo Domain and Its Binding to Lys36-Methylated Histone H3," *Nucleic Acids Res.* 34:6621-6628 (2006), which is hereby incorporated by reference in its entirety). The V1V2 sequences of the full-length V1V2 regions used as inserts into the scaffolds are listed in Table 5 below.

TABLE 5

Sequence of V1 and V2 Variable Loops in Immunogens and Antigens

| Strain (clade) | V1V2 Sequence |
|---|---|
| 1086 (c) | CVTLNCTNVKGNESDTSEVMKNCSFKATTELKDKKHKVHALFYKLDVVPLNGNSSSSGEYR LINC (SEQ ID NO: 3) |
| A244 (E) | CVTLHCTNANLTKANLTNVNNRTNVSNIIGNITDEVRNCSFNMTTELRDKKQKVHALFYKL DIVPIEDNNDSSEYRLINC (SEQ ID NO: 5) |
| 92TH023 (E) | CVTLNCTNANVTNVKNITNVPNIIGNITDEVRNCSFNMTTELRDKKQKVHALFYKLDIVPI EDNTSSSEYRLINC (SEQ ID NO: 18) |
| Case A2 (B) | CVTLNCIDLRNATNATSNSNTTNTTSSSGGLMMEQGEIKNCSFNITTSIRDKVQKEYALFY KLDIVPIDNPKNSTNYRLISC (SEQ ID NO: 19) |
| YU2 (B) | CVTLNCTDLRNATNTTSSSWETMEKGEIKNCSFNITTSIRDKVQKEYALFYNLDVVPIDNA SYRLISC (SEQ ID NO: 20) |
| ZM109 (C) | CVTLNCTSPAAHNESETRVKHCSFNITTDVKDRKQKVNATFYDLDIVPLSSSDNSSNSSLY RLISC (SEQ ID NO: 1) |
| CAP45 (C) | CVTLRCTNATINGSLTEEVKNCSFNITTELRDKKQKAYALFYRPDVVPLNKNSPSGNSSEY ILINC (SEQ ID NO: 4) |
| ZM53 (C) | CVTLNCSKLNNATDGEMKNCSFNATTELRDKKKQVYALFYKLDIVPLDGRNNSSEYRLINC (SEQ ID NO: 2) |

TABLE 5-continued

Sequence of V1 and V2 Variable Loops in Immunogens and Antigens

| Strain (clade) | V1V2 Sequence |
|---|---|
| cV2 peptide 92TH023 (E) | CSFNMTTELRDKKQKVHALFYKLDIVPIEDNTSSSEYRLINC (SEQ ID NO: 21) (V2 peptide) |

Genes of the V1V2-scaffolds were chemically synthesized and cloned into the pVRC8400 plasmid, followed by expression in HEK293 GnTI-/- cells and purification by affinity chromatography (Reeves et al., "Structure and Function in Rhodopsin: High-Level Expression of Rhodopsin With Restricted and Homogeneous N-Glycosylation by a Tetracycline-Inducible N-acetylglucosaminyltransferase I-Negative HEK293 S Stable Mammalian Cell Line," *Proc. Nat'l. Acad. Sci. U.S.A.* 99:13419-13424 (2002), which is hereby incorporated by reference in its entirety). Details of the design and constructions of the immunogens are described supra. V1V2(1086)-tags and V1V2(A244)-tags were provided by Dr. H Liao (Duke University), V1V2 (CaseA2)-gp70 and V1V2(92TH023)-gp70 were provided by Dr. A Pinter, and gp120(A244) was provided by Global Solutions for Infectious Diseases (South San Francisco, Calif.). gp120BaL, gp120(ZM53) and gp120(ZM233) were purchased from Immune Tech (New York, N.Y.), and a clade C V3 consensus linear, non-biotinylated 23-mer peptide (NNTRKSIRIGPGQTFYATGDIIG) (SEQ ID NO: 25) and the cyclic V292TH023 (cV292TH023, clade E) biotinylated peptide were purchased from BioPeptide (San Diego, Calif.).

Immunization Protocol. Female New Zealand White rabbits, 6-8 weeks old (with a body weight of ~2 kg), were purchased from Harlan Laboratories (Indianapolis, Ind.) and housed in the animal facility managed by the Department of Animal Medicine at the University of Massachusetts Medical School in accordance with an IACUC-approved protocol. Three to five rabbits were included in each immunization group. All rabbits received three DNA immunizations using a Bio-Rad Helios gene gun (Bio-Rad Laboratories, Hercules, Calif.). The gp120 DNA vaccine plasmids were coated onto 1.0 μm gold beads at a ratio of 2 μg of DNA per mg of gold. Each gene gun shot delivered 1 μg of DNA into a total of 36 non-overlapping sites on the shaved abdominal skin of each rabbit at each of the three priming immunizations. Several groups of rabbits received protein immunogens simultaneously with the three DNA priming immunizations as described below; in addition, all animals received two protein boosts. Each dose of protein immunogen was delivered as a bolus of 100 μg intramuscularly together with adjuvant. Blood was collected prior to immunization and two weeks after each immunization. Rabbits were bled periodically for up to 76 weeks after the initiation of the immunization protocol to assess the longevity of the Ab response. The immunization schedule for each of four rabbit experiments is shown in Table 6 below.

TABLE 6

Immunization Schedule.

| Week no. | Expt. H1 | Expt. H2 | Expt. H3 | Expt. H4 |
|---|---|---|---|---|
| 0 | DNA prime 1 | DNA prime 1 | DNA prime 1 | DNA prime 1 |
| 2 | DNA prime 2 | DNA prime 2 | DNA prime 2 | |
| 4 | DNA prime 3 | DNA prime 3 | DNA prime 3 | DNA prime 2 |
| 6 | | | | |
| 8 | | | | DNA prime 3 |
| 10 | Protein boost 1 | Protein boost 1 | Protein boost 1 | |
| 12 | | | | |
| 14 | Protein boost 2 | Protein boost 2 | Protein boost 2 | Protein boost 1 |
| 16 | | | | |
| 18 | | | | Protein boost 2 |

ELISA method. Immulon 4 plates were coated using 100 μl/well of the designated antigen at a concentration of 1 μg/ml in carbonate buffer, pH 9.6, and incubated overnight at 4° C. Plates were then washed six times with PBS/0.05% Tween. Subsequently, 100 μl/well of rabbit serum was added to the plates after dilution in RPMI medium containing 15% fetal bovine sera. Plates were incubated for 1.5 hr at 37° C. After six washes, bound Abs were detected by adding 100 μl/well of a 1:2000 dilution (in PBS/0.05% Tween) of alkaline phosphatase-conjugated mouse anti-rabbit IgG (Southern Biotech, Birmingham, Ala.) and incubated for 1.5 hr at 37° C. After six washes, 100 μl/well of 10% diethanolamine substrate was added, and after 30 minutes, the plates were read at 405 nm using a Sunrise Tecan™ microplate reader equipped with Magellan 6 software. All samples were tested in duplicate. Various V2 mAbs were used as positive controls and mAb 1418, specific for parvovirus B19, was used as a negative control in each experiment. For assessment of mAb reactivity, the same method was employed, using 10 μg/ml of mAb and alkaline phosphatase-conjugated goat anti-human IgG (Southern Biotech) as the secondary Ab.

Measurement of Ab-dependent cellular phagocytosis. Using the assay developed by Ackerman et. al (Ackerman et al., "A Robust, High-Throughput Assay to Determine the Phagocytic Activity of Clinical Antibody Samples," *J. Immunol. Methods* 366:8-19 (2011), which is hereby incorporated by reference in its entirety), 20 μs of gp120(ZM53) (Immune Technology) or V1V2(YU2)-1FD6 were biotinylated using EZ-Link™ Sulfo-NHS-LC-LC-Biotin (Thermo Scientific) and conjugated to fluorescent neutravidin beads (Invitrogen) according to manufacturer's instructions. Conjugated beads were washed and resuspended in 0.1% BSA-PBS to a working dilution of 1:100. Nine hundred thousand ($9 \times 10^5$) beads were aliquoted per well in round bottom 96-well plates. Four-fold dilutions of a mAb or two-fold dilutions of individual sera were added, incubated for 2 hr at 37° C., and washed. Twenty-five thousand ($2.5 \times 10^4$) THP-1 cells (ATCC) were added to each well and were incubated overnight. Phagocytosis was measured by flow cytometry. ADCP scores were calculated as (% bead-positive cells×mean fluorescence intensity [MFI] of bead-positive cells)/$10^6$.

Example 5

Immunogenicity Study Design

Eighteen different vaccination regimens were performed during the course of four experiments (H1-H4) (Table 7, FIG. 7A) using 95 rabbits to test the immunogenicity of 12 vaccines constructed with six V1V2 sequences presented on one of nine protein scaffolds, administered intramuscularly with one of two adjuvants. Each immunization regimen was tested in three to five animals. All groups (with the exception of experimental group H4/3, Table 7, FIG. 7A) were primed with codon-optimized DNA of gp120 from clade C strain ZM109F, as indicated in Table 7 (FIG. 7A); the timing of each immunizing dose is shown in Table 6. Five groups of animals were co-immunized with DNA and protein followed by protein only boosting (Table 7, FIG. 7A).

Example 6

Characterization of the Ab Response

Rabbits were bled prior to, and two weeks after each immunization. For all rabbits, the sera drawn two weeks after the last boost were used at a 1:100 dilution to screen by ELISA for reactivity against various V1V2 antigens. The results in Table 7 (FIG. 7A) show the mean optical densities (ODs) from all animals in each group when testing sera for Ab reactivity with a variety of antigens carrying the V1V2 region from various clades and in various configurations. Thus, cV292TH023 (clade E), V1V2(1086)-tags (clade C), V1V2(A244)-tags (clade E), and V1V292TH023-gp70 (clade E) were present in an unconstrained configuration since the mobility of the V1V2 region was not limited by the structure of or the placement in the scaffold. In contrast, the flexibility of the V1V2 regions present in V1V2(YU2)-1FD6 (clade B), V1V2(ZM109)-1FD6 (clade C), and the N160K mutant of V1V2(ZM109)-1FD6 was constrained by its placement in the 1FD6 scaffold (McLellan et al., "Structure of HIV-1 gp120 V1/V2 Domain With Broadly Neutralizing Antibody PG9," *Nature* 480:336-343 (2011), which is hereby incorporated by reference in its entirety). The reagents used here have been described previously (Liao et al., "Vaccine Induction of Antibodies Against a Structurally Heterogeneous Site of Immune Pressure Within HIV-1 Envelope Protein Variable Regions 1 and 2," *Immunity* 38:1-11 (2013); Zolla-Pazner et al., "Vaccine-Induced IgG Antibodies to V1V2 Regions of Multiple HIV-1 Subtypes Correlate With Decreased Risk of HIV-1 Infection," *Plos One* 9:e87572 (2014); McLellan et al., "Structure of HIV-1 gp120 V1/V2 Domain With Broadly Neutralizing Antibody PG9," *Nature* 480:336-343 (2011); Kayman et al., "Presentation of Native Epitopes in the V1/V2 and V3 Regions of Human Immunodeficiency Virus Type 1 gp120 by Fusion Glycoproteins Containing Isolated gp120 Domains," *J. Virol.* 68:400-410 (1994), which are hereby incorporated by reference in their entirety). Reactivity of pre-bleed sera, diluted 1:100, against each of these antigens gave OD readings <0.12. Sera drawn from animals after boosting twice with all of the immunization regimens were reactive above the pre-bleed background levels with essentially all antigens indicating that all of the various V1V2-scaffold proteins were immunogenic and induced Abs that were highly cross clade-reactive with epitopes displayed by diverse V1V2 regions. The pattern evident from the heat map of ELISA reactivities shown in Table 7 (FIG. 7A) indicates that the strongest responses were observed: (a) when the immunogens used presented V1V2 in a multimeric form rather than a monomeric configuration, (b) when priming included both DNA and protein immunogens, and (c) when the antigen coating the ELISA plates was V1V2 (ZM109)-1FD6.

Figure 7B:
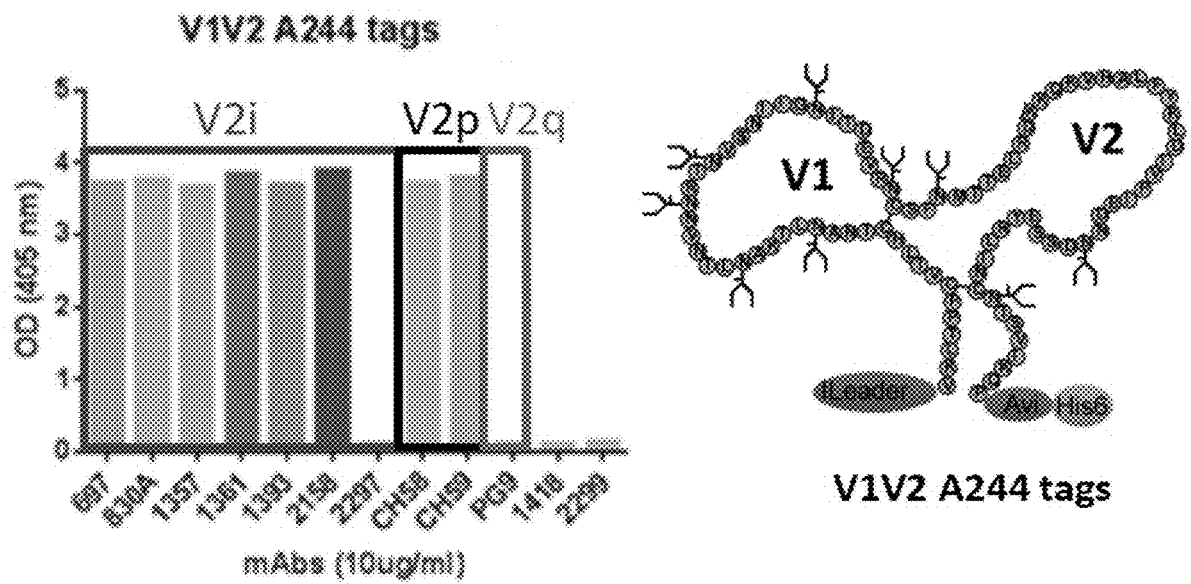
Figure 7C:
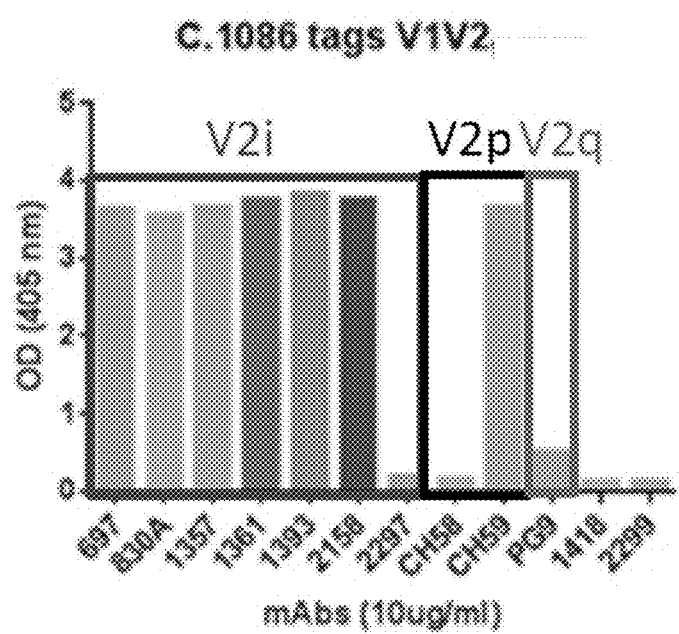

As shown previously, V1, V2 and V3 form the apex of the envelope trimer on the surface of virions and infected cells (Rusert et al., "Interaction of the gp120 V1V2 Loop With a Neighboring gp120 Unit Shields the HIV Envelope Trimer Against Cross-Neutralizing Antibodies," *J. Exp. Med.* 208: 1419-1433 (2011); Julien et al., "Crystal Structure of a Soluble Cleaved HIV-1 Envelope Trimer," *Science* 342: 1477-1483 (2013); Kwon et al., "Crystal Structure, Conformational Fixation and Entry-Related Interactions of Mature Ligand-Free HIV-1 Env," *Nat. Struct. Mol. Biol.* 22:522-531 (2015), which are hereby incorporated by reference in their entirety). Three categories of Abs have been described which are specific for different epitope regions in V1V2 (Mayr et al., "Epitope Mapping of Conformational V2-Specific Anti-HIV Human Monoclonal Antibodies Reveals an Immunodominant Site in V2," *PLos One* 8:e70859 (2013); Spurrier et al., "Functional Implications of the Binding Mode of a Human Conformation-Dependent V2 Monoclonal Antibody Against HIV," *J. Virol.* 88:4100-4112 (2014), each of which is hereby incorporated by reference in its entirety). (a) "V2p" Abs target a linear epitope represented by a peptide from the C strand of V2 which assumes a helical structure when bound to V2p mAbs. Only a few such human V2p-specific mAbs have been generated and these appear to be quite limited in their neutralizing ability but are able to mediate ADCC (Corti et al., "Analysis of Memory B cell responses and Isolation of Novel Monoclonal Antibodies With Neutralizing Breadth From HIV-1-Infected Individuals," *PLoS One* 5:e8805 (2010); Liao et al., "Vaccine Induction of Antibodies Against a Structurally Heterogeneous Site of Immune Pressure Within HIV-1 Envelope Protein Variable Regions 1 and 2," *Immunity* 38:1-11 (2013), which are hereby incorporated by reference in their entirety). V2p-specific Abs were generated in the studies described herein as rabbit sera bound to cyclic peptide, cV292TH023 (Table 7, FIG. 7A), a reagent which is only recognized by V2p-specific monoclonal Abs (mAbs) (FIG. 7E). (b) "V2i" Abs target a highly conformational epitope that includes the integrin binding site at residues 179-181 (Mayr et al., "Epitope Mapping of Conformational V2-Specific Anti-HIV Human Monoclonal Antibodies Reveals an Immunodominant Site in V2," *PLoS One* 8:e70859 (2013); Spurrier et al., "Functional Implications of the Binding Mode of a Human Conformation-Dependent V2 Monoclonal Antibody Against HIV," *J. Virol.* 88:4100-4112 (2014), which are hereby incorporated by reference in their entirety). Many V2i mAbs have been described, and serum V2i Abs exist in the majority of infected individuals (Gorny et al., "Human Anti-V2 Monoclonal Antibody That Neutralizes Primary but Not Laboratory Isolates of HIV-1," *J Virol.* 68:8312-8320 (1994); Gorny et al., "Functional and Immunochemical Cross-Reactivity of V2-Specific Monoclonal Antibodies From Human Immunodeficiency Virus Type 1-Infected Individuals," *Virology* 427:198-207 (2012); Klein et al., "Enhanced HIV-1 Immunotherapy by Naturally Arising Antibodies Targeting Resistant Variants," *J. Exp. Med.* 211: 2361-2372 (2014), which are hereby incorporated by reference in their entirety); these polyclonal and monoclonal Abs do not react with V2-derived peptides but are highly cross-reactive with monomeric gp120 from diverse strains and clades (Israel et al., "Prevalence of a V2 Epitope in Clade B Primary Isolates and Its Recognition by Sera From HIV-1 Infected Individuals," *AIDS* 11:128-130 (1997), which is hereby incorporated by reference in its entirety) as well as with V1V2-scaffolded proteins such as V1V2(CaseA2)-gp70 (FIGS. 7A-7E)(Gorny et al., "Human Anti-V2 Monoclonal Antibody That Neutralizes Primary but Not Laboratory Isolates of HIV-1," *J. Virol.* 68:8312-8320 (1994); Gorny et al., "Functional and Immunochemical Cross-Reactivity of V2-Specific Monoclonal Antibodies From Human Immunodeficiency Virus Type 1-Infected Individuals," *Virology* 427:198-207 (2012), which are hereby incorporated by reference in their entirety)). Binding of serum Abs to V1V2(CaseA2)-gp70 was correlated with the reduced HIV infection rate in RV144, demonstrating that the RV144 vaccine regimen induced V2i-like Abs (Haynes et al., "Immune Correlates Analysis of the ALVAC-AIDSVAX HIV-1 Vaccine Efficacy Trial," *N. Engl. J. Med.* 366:1275-1286 (2012); Zolla-Pazner et al., "Analysis of V2 Antibody Responses Induced in Vaccinees in the ALVAC/AIDSVAX HIV-1 Vaccine Efficacy Trial," *PLos One* 8:e53629 (2013); Zolla-Pazner et al., "Vaccine-Induced IgG Antibodies to V1V2 Regions of Multiple HIV-1 Subtypes Correlate With Decreased Risk of HIV-1 Infection," *Plos One* 9:e87572 (2014), which are hereby incorporated by reference in their entirety). Several of the reagents used to interrogate rabbit immune sera were able to bind to V2i mAbs, as shown in FIGS. 7B-7D. V1V2(ZM109)-1FD6, for example, binds to several V2i mAbs but V2i mAbs do not bind to the cV292TH023 peptide (FIGS. 7D-7E). As shown in Table 7 (FIG. 7A), immune sera from all rabbits bind strongly to V1V2(ZM109)-1FD6; (c) "V2q", or "V2 apex" Abs such as mAbs PG9 and CH01 (Walker et al., "Broad and Potent Neutralizing Antibodies From an African Donor Reveal a New HIV-1 Vaccine Target," *Science* 326:285-289 (2009); Bonsignori et al., "Analysis of a Clonal Lineage of HIV-1 Envelope V2/V3 Conformational Epitope-Specific Broadly Neutralizing Antibodies and Their Inferred Unmutated Common Ancestors," *J. Virol.* 85:9998-10009 (2011), which are hereby incorporated by reference in their entirety) preferentially target a V1V2 peptidoglycan which is part of the structure created by the quaternary interaction of the three V1V2 domains in the Env trimer (Walker et al., "Broad and Potent Neutralizing Antibodies From an African Donor Reveal a New HIV-1 Vaccine Target," *Science* 326:285-289 (2009); Wu et al., "Immunotypes of a Quaternary Structure of the HIV-1 Envelope Affect Viral Vulnerability to Neutralizing Antibodies," *J Virol.* 85:4578-4585 (2011), which are hereby incorporated by reference in their entirety). These mAbs mediate broad and potent neutralization, and, for avid binding, these V2q mAbs require the presence of the glycan at position N160 (Walker et al., "Broad and Potent Neutralizing Antibodies From an African Donor Reveal a New HIV-1 Vaccine Target," *Science* 326:285-289 (2009); Wu et al., "Immunotypes of a Quaternary Structure of the HIV-1 Envelope Affect Viral Vulnerability to Neutralizing Antibodies," *J. Virol.* 85:4578-4585 (2011), which are hereby incorporated by reference in their entirety). To determine if V2q-specific Abs were induced in immunized rabbits, their ability to bind to an N160K mutant of V1V2(ZM109)-1FD6 was tested since the glycan at N160 is critical for the binding of V2q mAbs. As shown in Table 7 (FIG. 7A), Abs in rabbit sera bound as well to V1V2(ZM109)(N160K)-1FD6 as to V1V2(ZM109)-1FD6. In addition, rabbit immune sera did not mediate neutralization (see below). These data indicate that the Abs induced in the rabbits immunized with V1V2-scaffolds did not have the immunochemical or functional characteristics of the potent and broadly neutralizing V2q Abs.

Figure 8A:
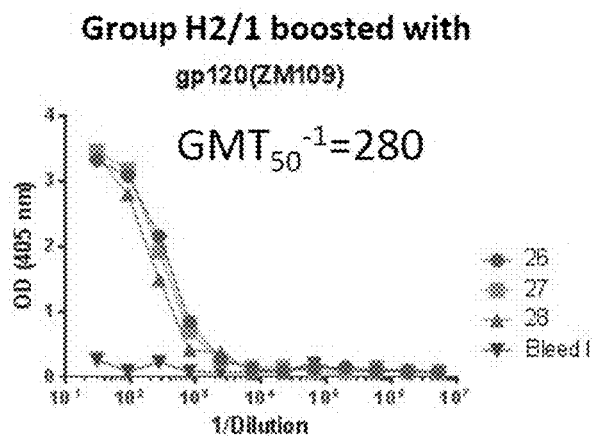
FIGS. 8A-8F show results of titration of immune rabbit sera against V1V2(ZM109)-1FD6. Pools of pre-bleed sera (Bleed I) from each group, or serum drawn two weeks after the last boost from individual animals (numbered 26-50) in each of the six groups of animals immunized as part of experiment H2 (see Table 7, FIG. 7A), were titrated in ELISA (Group H2/1 (FIG. 8A); Group H2/2 (FIG. 8B); Group H2/3 (FIG. 8C); Group H2/4 (FIG. 8D); Group H2/5 (FIG. 8E); and Group H2/6 (FIG. 8F).
Figure 8B:
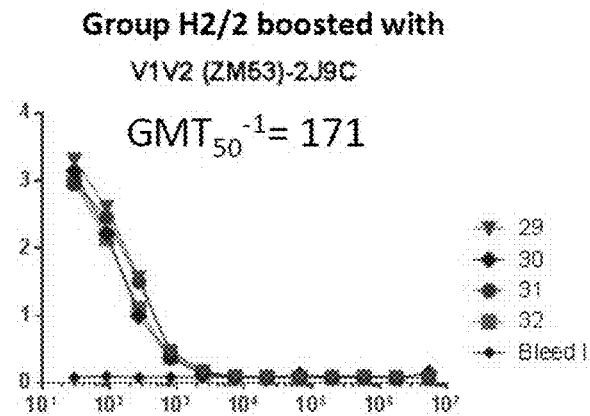
Figure 8C:
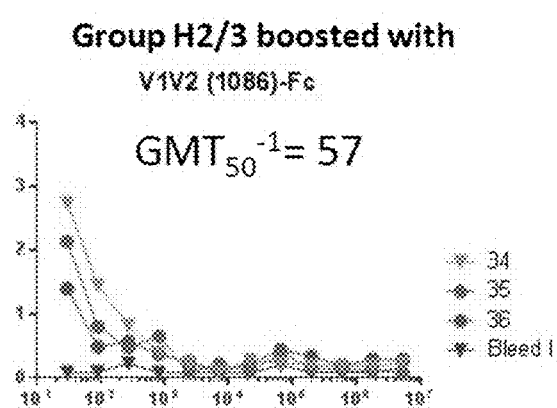
Figure 8D:
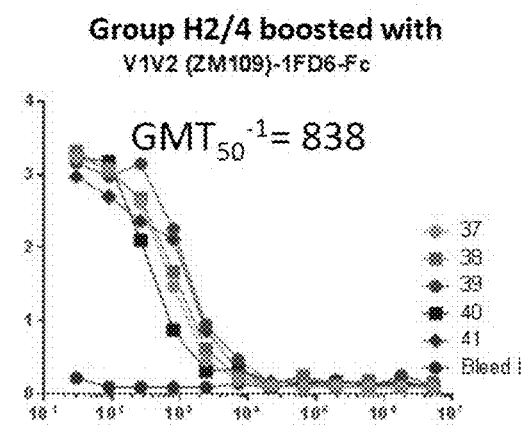
Figure 8E:
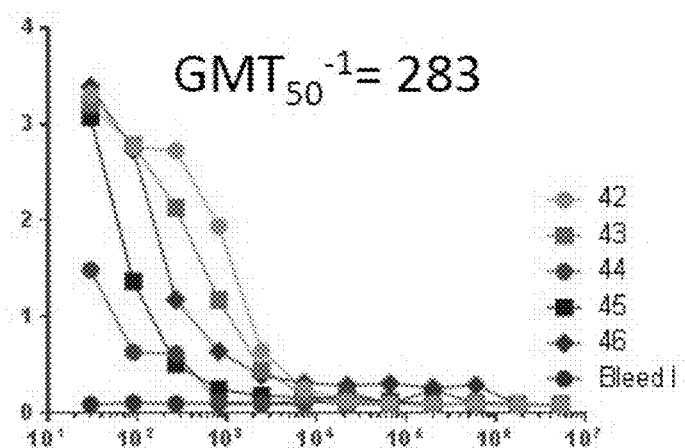
Figure 8F:
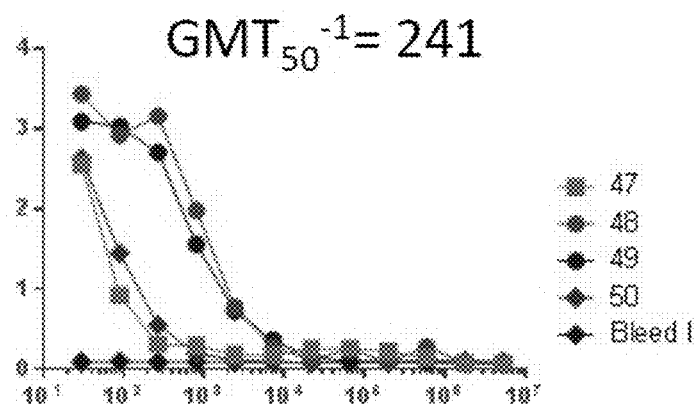

To further characterize the responses to the various immunogens used here, Ab reactivities were compared when boosting with gp120 protein vs. various V1V2-scaffold immunogens. The data are shown in FIGS. 8A-8F, in which immune sera from all animals in experiments H2 (Group H2/1 (FIG. 8A); Group H2/2 (FIG. 8B); Group H2/3 (FIG. 8C); Group H2/4 (FIG. 8D); Group H2/5 (FIG. 8E); Group H2/6 (FIG. 8F)), drawn two weeks after the second boost, were tested for reactivity with V1V2(ZM109)-1FD6. As expected, the pre-bleed sera showed no reactivity, while sera from all immunized rabbits reacted with V1V2(ZM109)-1FD6. Of particular note is that the level of Abs in the animals boosted with various V1V2-scaffold immunogens (with the exception of V1V2(1086)-Fc) was as high or higher than the level of Abs achieved in rabbits boosted with the gp120(ZM109) protein. Note that the $GMT_{50}^{-1}$ in gp120 (ZM109) boosted animals (Group H2/1 in FIG. 8A) was 280 whereas the $GMT_{50}^{-1}$ values for animals boosted in the same experiment with V1V2(ZM109)-1FD6-Fc or V1V2 (ZM109)-TTB were 838 and 283, respectively. There appeared to be little if any contribution of anti-scaffold Abs to the $GMT_{50}^{-1}$ values (data not shown) which is consistent with the relatively small size and expected poor immunogenicity of the scaffolds, e.g., the molecular weight of 1FD6 is 6.3 kD, of TTB is 19.2 kD, of 2F5K is 16.9 kD, and of 2J9C is 19.7 kD.

Example 7

Comparison of the Efficacy of Various Immunization Regimens

Figures 9A, 9B, 9C, 9D, 9E:
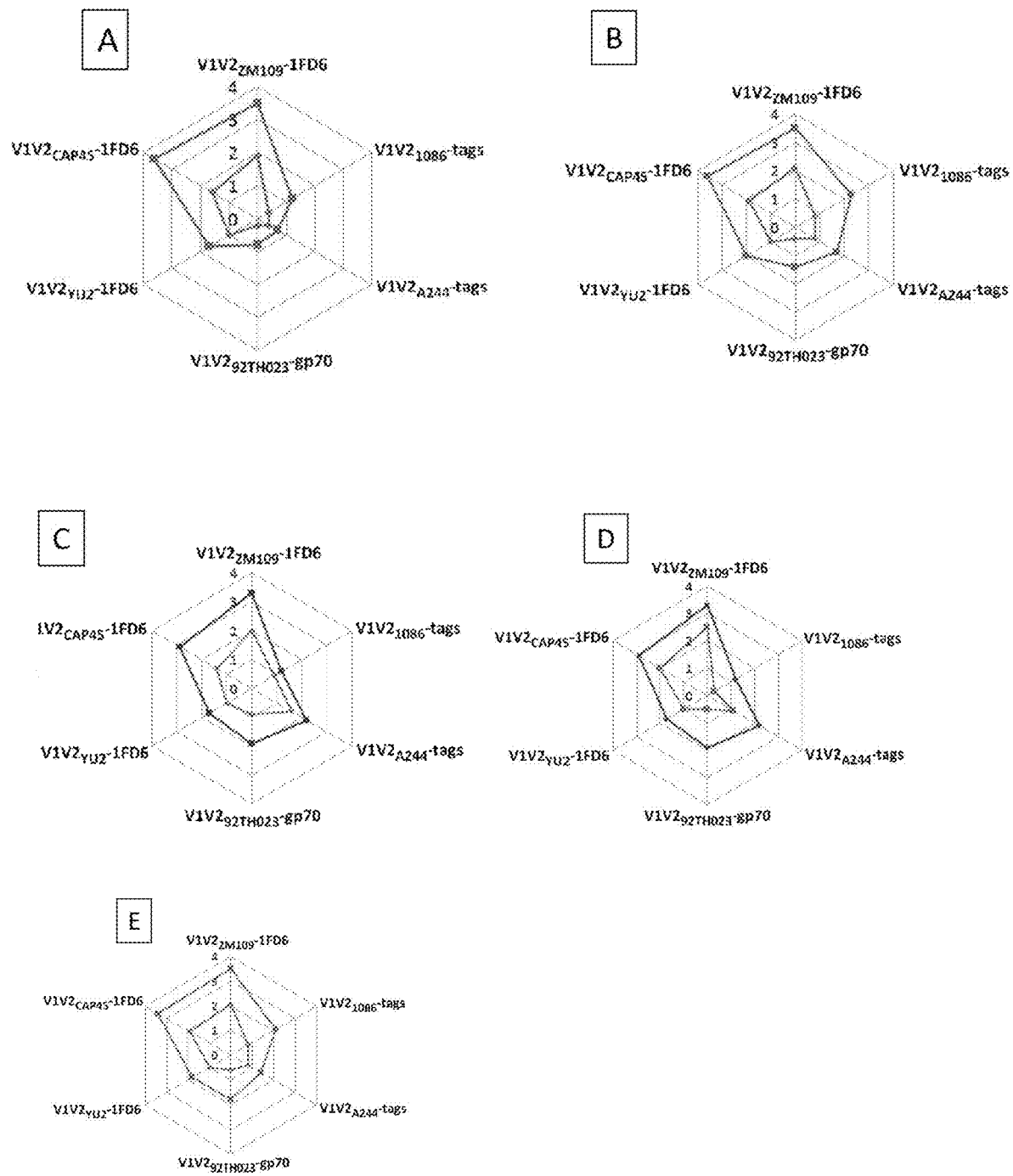

Animals that were co-primed with gp120 DNA plus a V1V2-scaffold protein (either V1V2(ZM109)-TTB or V1V2 (ZM53)-2J9C), followed by two boosts with the same V1V2-scaffold protein gave stronger Ab responses against six V1V2 antigens than animals primed with gp120 DNA alone and boosted with a V1V2-scaffold protein (FIGS. 9A and 9B). The specifics of each panel in FIG. 9 are provided in FIG. 9F, which also shows the $GMT_{50}^{-1}$ values against V1V2(ZM109)-1FD6 for each group. For example, in the experiment shown in FIG. 9A, using the V1V2(ZM109)-TTB protein immunogen, the comparative $GMT_{50}^{-1}$ levels for the two different priming strategies (DNA+protein vs. DNA alone) were 959 and 283; similarly, in the experiment shown in FIG. 9B, using the V1V2(ZM53)-2J9C protein immunogen, the comparative $GMT_{50}^{-1}$ levels for the two different priming strategies (DNA+protein vs. DNA) were 2246 and 171, respectively (FIG. 9F).

Animals that were co-primed (×3) with DNA and the V1V2(ZM53)-2J9C protein and then boosted with V1V2 (ZM53)-2J9C using incomplete Freund's adjuvant (IFA) as an adjuvant gave stronger responses than animals receiving the same immunization regimen using alum (FIG. 9C). The $GMT_{50}^{-1}$ values of the sera from the animals in these groups, when titrated against V1V2(ZM109)-1FD6, were 149 and 37 for the IFA and alum groups, respectively (FIG. 9F).

Animals that were co-primed with DNA+V1V2(ZM53)-2J9C scaffold protein and boosted with the homologous V1V2(ZM53)-2J9C scaffold protein gave a better response than animals receiving the DNA+V1V2(ZM53)-2J9C scaffold protein prime followed by boosting with the heterologous V1V2(A244)-2J9C scaffold protein (FIG. 9D). The $GMT_{50}^{-1}$ values for the homologous vs. heterologous prime and boosting regimens were 149 and 22, respectively (FIG. 9F).

The V1V2(ZM53)-2F5K protein immunogen gave a stronger response than the V1V2(ZM53)-2J9C immunogen as shown in FIG. 9E. The $GMT_{50}^{-1}$ values for titration against V1V2(ZM109)-1FD6 for these two groups were 1412 and 171, respectively (FIG. 9F).

Example 8

Durability of the Ab Response

To determine the durability of the immune response elicited with various immunogens and vaccine regimens, selected groups of rabbits were housed for up to 76 weeks and bled at various times after each immunization. The kinetics and the duration of the Ab responses against various antigens are shown for three groups of animals in Tables 8, 9 and 10 (FIGS. 10A, 10B, and 10C, respectively). When gp120(ZM109F) DNA was used alone for the prime, Abs reacted poorly with all antigens except gp120(ZM233) (experimental group H1/5, Table 8 (FIG. 10A)).

After boosting with gp120(ZM109F) protein, reactivity of gp120(ZM233)-directed Abs increased and remained strong, and Abs to V1V2(CaseA2)-gp70 were significantly elevated, although reactivity to other antigens remained weak. Antibody levels began to wane at week 21, which was 11 weeks after the last boost. In contrast, when DNA+V1V2-scaffold immunogens were used for the three priming doses, followed by boosting with V1V2-scaffold proteins carrying the homologous or heterologous V1V2 regions in the epitope-scaffold boosting immunogen (Tables 9 (FIG. 10B) and 10 (FIG. 10C), respectively), robust responses were generated against both V1V2 antigens and gp120 after the 2nd or 3rd priming doses.

Antibody levels to the V1V2-scaffold antigens increased after the protein boosts. Rabbits were maintained and bled periodically for the longest period of time in the experiment where rabbits received DNA+V1V2(ZM53)-2J9C as the prime and V1V2(ZM53)-2J9C for the boost (Experiment H3/4, Table 9 (FIG. 10B)). The Ab response to V1V2 antigen constructs from clades B (V1V2(YU2)-1FD6) and C (V1V2(ZM109)-TTB) were clearly enhanced by the protein boosts and were maintained at peak activity through weeks 26-36 which corresponded to 16-26 weeks after the last protein boost; after that there was a very gradual decline. Ab responses were still detectable at week 76, which was 66 weeks after the last boost. As seen in the data in Table 7 (FIG. 7A), V1V2-specific Abs reacted most strongly when the V1V2 domain was held in a constrained position by the scaffold proteins (in this case V1V2(YU2)-1FD6 and V1V2(ZM109)-TTB) as opposed to antigens that bear the V1V2 domain in an unconstrained configurations (gp120(ZM233) and V1V2(CaseA2)-gp70).

The data in Tables 8, 9 and 10 (FIGS. 10A, 10B, and 10C, respectively) also indicate that the Ab response is focused on V1V2. Antibodies reactive with a V3 consensus C peptide were induced, as expected, in the rabbits immunized with gp120(ZM109) DNA and gp120(ZM109) protein (Table 8 (FIG. 10A)), but in animals primed with DNA gp120 (ZM109)+V1V2-scaffolds and boosted with the V1V2-scaffolds, V3 Abs were only detectable at levels just above background, and only during the immunization with the priming gp120 DNA (Tables 9 (FIG. 10B) and 10 (FIG. 10C)). Thus, Ab responses induced by rationally-designed V1V2-scaffold immunogens focused the Ab response on the V1V2 region to the virtual exclusion of other Env antigens.

Example 9

Biologic Function of Abs Induced by V2-Targeting Vaccines

V2i-specific mAbs have little to no neutralizing activity (Gorny et al., "Functional and Immunochemical Cross-Reactivity of V2-Specific Monoclonal Antibodies From Human Immunodeficiency Virus Type 1-Infected Individuals," *Virology* 427:198-207 (2012), which is hereby incorporated by reference in its entirety), and while there was a correlation between reduced risk of infection in RV144 and the level of V1V2 binding Abs, there was no correlation with serum neutralizing activity (Montefiori et al., "Magnitude and Breadth of the Neutralizing Antibody Response in the RV144 and Vax003 HIV-1 Vaccine Efficacy Trials," *J. Infect. Dis.* 206:431-441 (2012), which is hereby incorporated by reference in its entirety). Thus, it was not expected that the immune sera from the rabbits immunized in these studies would display neutralizing activity. To test for neutralizing activity of immune rabbit sera, a modified, more sensitive version of the TZM.b1 assay was used (Upadhyay et al., "Distinct Mechanisms Regulate Exposure of Neutralizing Epitopes in the V2 and V3 Loops of HIV-1 Envelope," *J. Virol.* 88:12853-12865 (2014), which is hereby incorporated by reference in its entirety) in which virus and sera were incubated together for 24 hr prior to application to cells. Indeed, there was no neutralizing activity when sera from the five animals in one of the best groups (H3/4: primed with gp120(ZM109F) DNA+V1V2(ZM53)-2J9C and boosted with V1V2(ZM53)-2J9C) were tested against BaL.26, YU2 and SF162 (data not shown).

Figures 11A, 11B:
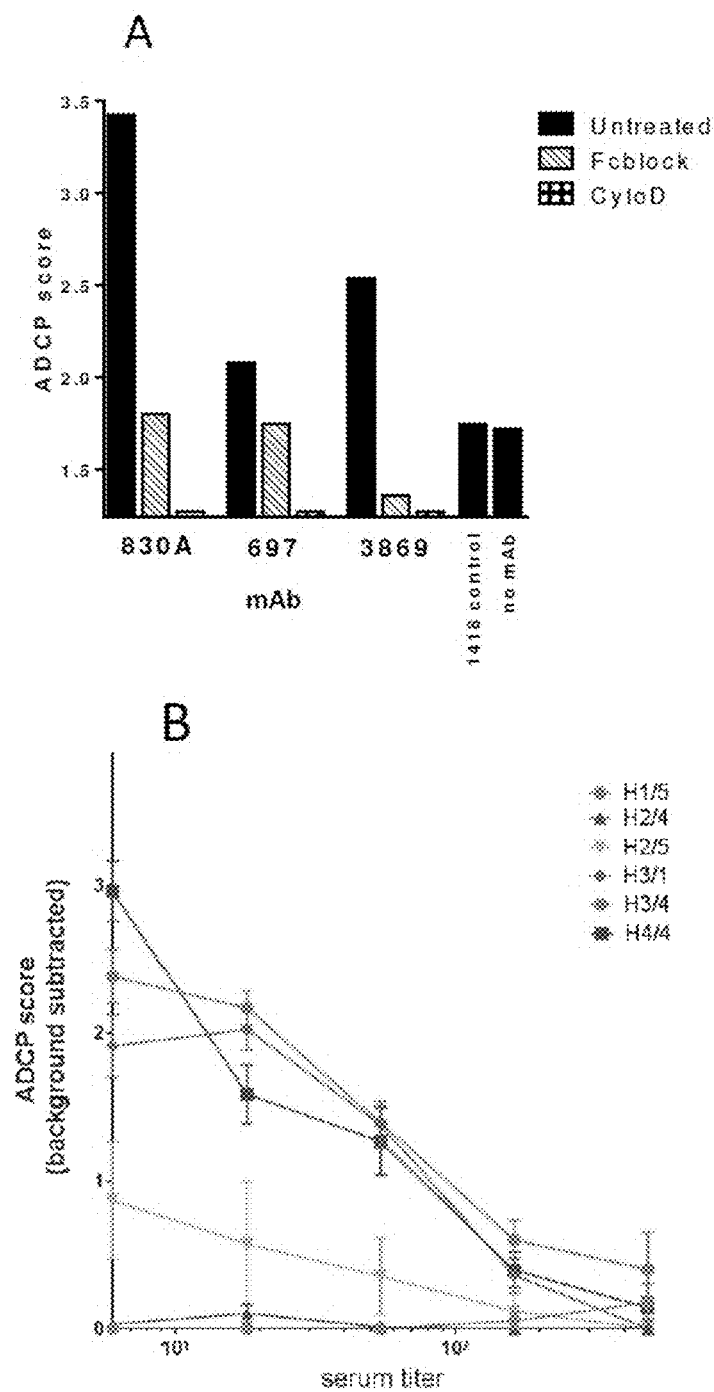
FIGS. 11A-11D show a phagocytosis assay with monoclonal antibodies (mAbs) and rabbit immune sera. The ADCP assay was performed and reported as ADCP scores as described in Methods.
Figures 11C, 11D:
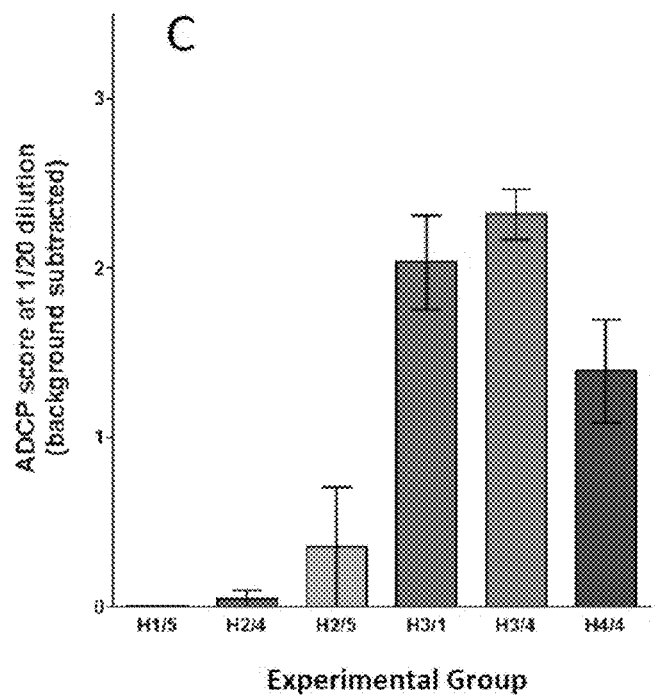

Since increasing attention has been focused on Fc-dependent Ab functions, the ability of the serum Abs from immunized rabbits to mediate phagocytosis (Chung et al., "Polyfunctional Fc-Effector Profiles Mediated by IgG Subclass Selection Distinguish RV144 and VAX003 Vaccines," *Sci. Transl. Med.* 6:228ra238 (2014); Chung et al., "Dissecting Polyclonal Vaccine-Induced Humoral Immunity against HIV Using Systems Serology," *Cell* 163:988-998 (2015); Barouch et al., "Protective Efficacy of a Global HIV-1 Mosaic Vaccine Against Heterologous SHIV Challenges in Rhesus Monkeys," *Cell* 155:531539 (2013); Barouch et al., "Protective Efficacy of Adenovirus/Protein Vaccines Against SIV Challenges in Rhesus Monkeys," *Science* 349:320-324 (2015), which are hereby incorporated by reference in their entirety) was tested. For optimizing the assay that was first described by Ackerman et al. (Ackerman et al., "A Robust, High-Throughput Assay to Determine the Phagocytic Activity of Clinical Antibody Samples," *J. Immunol. Methods* 366:8-19 (2011), which is hereby incorporated by reference in its entirety), the phagocytic activity of THP-1 cells incubated with various HIV Env-specific human mAbs bound to beads coated with biotinylated gp120(ZM53) was assessed. FIG. 11A shows the Ab-dependent cellular phagocytosis (ADCP) scores generated using the optimized assay described in the Methods section. Robust phagocytosis was achieved with beads coated with gp120(ZM53) and then bound to V2i mAbs 830A or 697 or to V3-specific mAb 3869. This activity is shown to be Fc-dependent as illustrated by the ability of Cytochalasin D and human Fc Receptor Blocking Reagent (Fcblock) to inhibit phagocytosis. This optimized assay was then used to test the phagocytic activity of sera from each rabbit in several groups of immunized animals. Immune sera were each titrated from a dilution of 1:6 to 1:486 for phagocytic activity against beads coated with V1V2(ZM109)-1FD6 and the mean ADCP score for each group of rabbits is shown in FIG. 11B. Similar levels of phagocytic activity were detected in sera from rabbits in three of the six groups tested: H3/1 (primed with gp120 DNA and boosted with V1V2 (ZM53)-2F5K), H3/4 (primed with gp120 DNA+V1V2 (ZM53)-2J9C protein and boosted with V1V2(ZM53)-2J9C), and H4/4 (primed with gp120 DNA+V1V2(ZM53)-2J9C protein and boosted with V1V2(A244)-2J9C). In contrast, little or no activity was detected in sera from animals in H1/5 (primed with gp120 DNA and boosted with gp120 protein), H2/4 (primed with DNA and boosted with V1V2(ZM109)-1FD6-Fc), and H2/5 (primed with DNA and boosted with V1V2(ZM109)-TTB). A similar pattern was found for sera tested at a dilution of 1:20 derived from the same six groups of animals and tested using beads coated with V1V2(YU2)-1FD6 (FIG. 11C). It is particularly striking that boosting with gp120 protein does not induce Abs with phagocytic activity (Group H1/5) while three groups boosted with V1V2(ZM53)-2F5K, V1V2(ZM53)-2J9C, or V1V2(A244)-2J9C displayed strong activity in this assay; this denotes a significant qualitative difference in the Abs induced by V1V2-scaffold immunogens as opposed to gp120 protein. In addition, it is noteworthy that there is no correlation between phagocytic activity with V1V2 (ZM109)-1FD6-coated beads and Ab reactivity of the same sera in ELISA against V1V2(ZM109)-1FD6 (FIGS. 11B and 11D).

Discussion of Examples 5-9

The experiments described herein were designed to focus a vaccine-induced Ab response on the V1V2 region of the HIV-1 gp120 envelope glycoprotein since Abs to this region have been associated with reduced rates of HIV, SIV and SHIV infection (Chung et al., "Polyfunctional Fc-Effector Profiles Mediated by IgG Subclass Selection Distinguish RV144 and VAX003 Vaccines," *Sci. Transl. Med.* 6:228ra238 (2014); Haynes et al., "Immune Correlates Analysis of the ALVAC-AIDSVAX HIV-1 Vaccine Efficacy Trial," *N. Engl. J. Med.* 366:1275-1286 (2012); Chung et al., "Dissecting Polyclonal Vaccine-Induced Humoral Immunity Against HIV Using Systems Serology," *Cell* 163:988-998 (2015); Zolla-Pazner et al., "Analysis of V2 Antibody Responses Induced in Vaccinees in the ALVAC/AIDSVAX HIV-1 Vaccine Efficacy Trial," *PLos One* 8:e53629 (2013); Zolla-Pazner et al., "Vaccine-Induced IgG Antibodies to V1V2 Regions of Multiple HIV-1 Subtypes Correlate With Decreased Risk of HIV-1 Infection," *Plos One* 9:e87572 (2014); Yates et al., "Vaccine-Induced Env V1-V2 IgG3 Correlates With Lower HIV-1 Infection Risk and Declines Soon After Vaccination," *Sci. Transl. Med.* 6:228ra239 (2014); Vaccari et al., "Adjuvant-Dependent Innate and Adaptive Immune Signatures of Risk of SIV Acquisition," *Nat. Med.* 22:762-770 (2016); Pegu et al., "Neutralizing Antibodies to HIV-1 Envelope Protect More Effectively In Vivo Than Those to the CD4 Receptor," *Sci. Transl. Med.* 6:243ra288 (2014), which are hereby incorporated by reference in their entirety). The results show that when using different immunization regimens employing gp120 DNA and various V1V2-protein scaffold immunogens, the V1V2 region was targeted by the Ab response with little or no induction of Abs to other Env epitopes. The response was durable, with Abs demonstrable for >1 year, and the vaccine-induced Abs were (a) highly cross-reactive with the V1V2 regions and gp120 molecules derived from diverse strains and clades, (b) directed at linear and conformational epitopes in V2, and (c) able to mediate phagocytosis, a function that has been correlated with protection from HIV, SIV and SHIV as well as other viral diseases (Chung et al., "Polyfunctional Fc-Effector Profiles Mediated by IgG Subclass Selection Distinguish RV144 and VAX003 Vaccines," *Sci. Transl. Med.* 6:228ra238 (2014); Chung et al., "Dissecting Polyclonal Vaccine-Induced Humoral Immunity against HIV Using Systems Serology," *Cell* 163:988-998 (2015); Barouch et al., "Protective Efficacy of a Global HIV-1 Mosaic Vaccine Against Heterologous SHIV Challenges in Rhesus Monkeys," *Cell* 155:531-539 (2013); Barouch et al., "Protective Efficacy of Adenovirus/Protein Vaccines Against SIV Challenges in Rhesus Monkeys," *Science* 349:320-324 (2015), which are hereby incorporated by reference in their entirety). The specificity of the vaccine-induced rabbit Abs were similar to human-derived V2i-specific mAbs on the basis of their ELISA reactivity with various V1V2-scaffold immunogens (Table 7 (FIG. 7A) and FIGS. 7B-7E), their inability to neutralize viruses, and their ability to mediate Fc-dependent phagocytosis (FIG. 11).

The rationale for using an epitope-specific approach to vaccine design was based on studies in the literature indicating that targeting specific epitopes of infectious organisms could protect against infection by various pathogens, an approach termed reverse vaccinology (Rappuoli, R., "Reverse Vaccinology," *Curr. Opin. Microbiol.* 3:445-450 (2000), which is hereby incorporated by reference in its entirety). For example, targeting the Factor H-binding protein of Neisseria meningitides with an experimental vaccine prevented meningococcal meningitis and sepsis in mice (Delany et al., "Vaccines, Reverse Vaccinology, and Bacterial Pathogenesis," *Cold Spring Harb. Perspect. Med.* 3:a012476 (2014), which is hereby incorporated by reference in its entirety), and targeting the site Ø of the fusion glycoprotein of respiratory syncytium virus (RSV) elicited high levels of RSV-specific Abs with neutralizing activity (McLellan et al., "Structure-Based Design of a Fusion Glycoprotein Vaccine for Respiratory Syncytial Virus," *Science* 342:592-598 (2013), which is hereby incorporated by reference in its entirety). Moreover, focusing the immune response on the V3 region of HIV gp120 Env with V3-scaffold immunogens induced cross-clade neutralizing Abs and recapitulated the binding and biologic activity of V3-specific human mAbs (Totrov et al., "Structure-Guided Design and Immunological Characterization of Immunogens Presenting the HIV-1 gp120 V3 Loop on a CTB Scaffold," *Virology* 405:513-523 (2010); Zolla-Pazner et al., "Cross-Clade HIV-1 Neutralizing Antibodies Induced With V3-Scaffold Protein Immunogens Following Priming With gp120 DNA," *J. Virol.* 85:9887-9898 (2011), which are hereby incorporated by reference in their entirety). Here, a successful reverse vaccinology approach is described using immunogens that target the V1V2 portion of gp120. This study and the successful reverse vaccinology studies cited above stand in marked contrast to several unsuccessful attempts to use epitope-scaffold immunogens to elicit polyclonal responses designed to recapitulate the specificity and function of broadly neutralizing mAbs that target HIV sites of vulnerability (Arnold et al., "Broad Neutralization of Human Immunodeficiency Virus Type 1 (HIV-1) Elicited From Human Rhinoviruses That Display the HIV-1 gp41 ELDKWA Epitope," *J. Virol.* 83:5087-5100 (2009); Liang et al., "Epitope Insertion Into Variable Loops of HIV-1 gp120 as a Potential Means to Improve Immunogenicity of Viral Envelope Protein," *Vaccine* 17:2862-2872 (1999); Zhang et al., "Induction of Mucosal and Systemic Neutralizing Antibodies Against Human Immunodeficiency Virus Type 1 (HIV-1) by Oral Immunization With Bovine Papillomavirus-HIV-1 gp41 Chimeric Virus-Like Particles," *J. Virol.* 78:8342-8348 (2004); Ofek et al., "Elicitation of Structure-Specific Antibodies by Epitope Scaffolds," *Proc. Nat'l. Acad. Sci. U.S.A.* 107:17880-17887 (2010); Zhou et al., "Transplanting Supersites of HIV-1 Vulnerability," *PLoS One* 9:e99881 (2014), which are hereby incorporated by reference in their entirety).

It has been suggested that non-neutralizing mechanisms such as phagocytosis, neutrophil activation, and ADCC are likely to play a role in both HIV prevention and reservoir-eliminating therapeutic approaches (Sips et al., "Fc Receptor-Mediated Phagocytosis in Tissues as a Potent Mechanism for Preventive and Therapeutic HIV Vaccine Strategies," *Mucosal. Immunol.* doi:10.1038/mi.2016.12 (2016); Robinson, H. L., "Non-Neutralizing Antibodies in Prevention of HIV Infection," *Exp. Opin. Biol. Ther.* 13:197-207 (2013), which are hereby incorporated by reference in their entirety). This is supported by the RV144 clinical trial where a correlate of reduced infection was found with various Fc-mediated activities but not with neutralization (Corey et al., "Immune Correlates of Vaccine Protection Against HIV-1 Acquisition," *Sci. Transl. Med.* 7:310rv317 (2015); Li et al., "Fc Gamma IIC Polymorphisms Associate With HIV-1 Vaccine Protection in RV144 Trial," *J. Clin. Invest.* 124:3879-3890 (2014); Pollara et al., "HIV-1 Vaccine-Induced C1 and V2 Env-Specific Antibodies Synergize for Increased Antiviral Activities," *J. Virol.* 88:7715-7726 (2014); Chung et al., "Polyfunctional Fc-Effector Profiles Mediated by IgG Subclass Selection Distinguish RV144 and VAX003 Vaccines," *Sci. Transl. Med.* 6:228ra238 (2014); Haynes et al., "Immune Correlates Analysis of the ALVAC-AIDSVAX HIV-1 Vaccine Efficacy Trial," *N. Engl. J. Med.* 366:1275-1286 (2012); Bonsignori et al., "Antibody-Dependent Cellular Cytotoxicity-Mediating Antibodies From an HIV-1 Vaccine Efficacy Trial Target Multiple Epitopes and Preferentially Use the VH1 Gene Family," *J. Virol.* 86:11521-11532 (2012); Montefiori et al., "Magnitude and Breadth of the Neutralizing Antibody Response in the RV144 and Vax003 HIV-1 Vaccine Efficacy Trials," *J. Infect. Dis.* 206:431-441 (2012); Liao et al., "Vaccine Induction of Antibodies Against a Structurally Heterogeneous Site of Immune Pressure Within HIV-1 Envelope Protein Variable Regions 1 and 2," *Immunity* 38:1-11 (2013); Pollara et al., "Epitope Specificity of Human Immunodeficiency virus-1 Antibody Dependent Cellular Cytotoxicity [ADCC] Responses," *Curr. HIV Res.* 11:378-387 (2013); Chung et al., "Dissecting Polyclonal Vaccine-Induced Humoral Immunity against HIV Using Systems Serology," *Cell* 163:988-998 (2015), which are hereby incorporated by reference in their entirety). In addition, myriad studies have shown an association between Fcγ-dependent Ab functions and reduced infection with SIV and SHIV (Alpert et al., "ADCC Develops Over Time During Persistent Infection With Live-Attenuated SIV and Is Associated With Complete Protection Against SIV(mac)251 Challenge," *PLoS Pathog.* 8:e1002890 (2012); Barouch et al., "Protective Efficacy of a Global HIV-1 Mosaic Vaccine Against Heterologous SHIV Challenges in Rhesus Monkeys," *Cell* 155:531539 (2013); Pegu et al., "Antibodies With High Avidity to the gp120 Envelope Protein in Protection From Simian Immunodeficiency Virus SIV(mac251) Acquisition in an Immunization Regimen That Mimics the RV-144 Thai Trial," *J. Virol.* 87:1708-1719 (2013); Vaccari et al., "Adjuvant-Dependent Innate and Adaptive Immune Signatures of Risk of SIV Acquisition," *Nat. Med.* 22:762-770 (2016); Barouch et al., "Protective Efficacy of Adenovirus/Protein Vaccines Against SIV Challenges in Rhesus Monkeys," *Science* 349:320-324 (2015), which are hereby incorporated by reference in their entirety).

The mechanism by which Abs mediate various Fc-dependent anti-viral functions is the subject of on-going studies. The protective role of HIV Abs in binding to Fc receptors was established in passive immunization experiments (Hessell et al., "Fc Receptor but Not Complement Binding Is Important in Antibody Protection Against HIV," *Nature* 449:101-104 (2007), which is hereby incorporated by reference in its entirety). In addition, the nature of Fc-glycan structures was shown to selectively promote Fc-effector functions independent of Ab specificity for HIV epitopes, and particular Ab glycan structures were associated with enhanced ADCC as well as ADCP activity (Chung et al., "Identification of Antibody Glycosylation Structures That Predict Monoclonal Antibody Fc-Effector Function," *AIDS* 28:2523-2530 (2014), which is hereby incorporated by reference in its entirety). Further studies have indicated that Fcγ receptor-mediated activity is associated with preferential engagement of activating, but not inhibitory Fcγ receptors (Bournazos et al., "Broadly Neutralizing Anti-HIV-1 Antibodies Require Fc Effector Functions for In Vivo Activity," *Cell* 158:12431253 (2014), which is hereby incorporated by reference in its entirety). Thus, biologic functions of non-neutralizing Abs are affected by many factors, including isotype, subtype, affinity for Fc receptors, and ability to activate complement-all of which are functions of the Fc rather than the Fab fragment of immunoglobulins (Huber & Trkola, "Humoral Immunity to HIV-1: Neutralization and Beyond," *J. Intern. Med.* 262:5-25 (2007), which is hereby incorporated by reference in its entirety). It is notable, therefore, that in targeting the immune response to V1V2, Abs have been induced that, as expected on the basis of previous data (Gorny et al., "Functional and Immunochemical Cross-Reactivity of V2-Specific Monoclonal Antibodies From Human Immunodeficiency Virus Type 1-Infected Individuals," *Virology* 427:198-207 (2012), which is hereby incorporated by reference in its entirety), have no neutralizing activity but mediate ADCP. Notably, there was no phagocytic activity in the sera of rabbits immunized with gp120 DNA and gp120 protein (experimental group H1/5) whereas the immune sera tested from animals immunized with selected gp120 DNA and V1V2-scaffold proteins (experimental groups H3/1, H3/4 and H4/4) displayed this activity (FIG. 11) indicating that there was a qualitative difference in the immune response induced by gp120 as opposed to the V1V2-scaffold immunogens.

The induction of ADCP by immunogens V1V2-2F5K and V1V2-2J9C, as opposed to the failure to induce ADCP with gp120 protein may bear on the differing conformations of these antigens. V1V2 is presented by the 2F5K and 2J9C scaffolds as an apical trimeric structure whose conformation is constrained by their insertion in these scaffolds as described supra. In contrast, the V1V2 region in gp120 is presented as a monomeric, unconstrained domain. The V1V2-2J9C design was based on the V1V2 structure as observed in complex with V2q mAb PG9 (McLellan et al., "Structure of HIV-1 gp120 V1/V2 Domain With Broadly Neutralizing Antibody PG9," *Nature* 480:336-343 (2011), which is hereby incorporated by reference in its entirety), while the V1V2-2F5K design was based on the V1V2 structure in complex with V2i mAb 830A (Pan et al., "The V1V2 Region of HIV-1 gp120 Forms a Five-Stranded Beta Barrel," *J. Virol.* 89:8003-8010 (2015), which is hereby incorporated by reference in its entirety). The geometry of the trimeric configuration (position and orientation with respect to the trimer axis) of V1V2 domains in both designs was guided by the low resolution cryo-EM structure of the SOSIP trimeric spike in complex with mAb PG9 (Julien et al., "Crystal Structure of a Soluble Cleaved HIV-1 Envelope Trimer," *Science* 342:1477-1483 (2013), which is hereby incorporated by reference in its entirety) before the higher resolution structure became available (Kwon et al., "Crystal Structure, Conformational Fixation and Entry-Related Interactions of Mature Ligand-Free HIV-1 Env," *Nat. Struct. Mol. Biol.* 22:522-531 (2015), which is hereby incorporated by reference in its entirety).

In summary, the structure of V1V2 epitopes recognized by various human mAbs that target the V1V2 region of gp120 were used to design V1V2-scaffold immunogens which induced Abs in rabbits that recapitulated the specificity and functional activity of human V2i mAbs. The vaccine-induced rabbit serum Abs were focused on the V1V2 region, cross-clade reactive, mediated Ab-dependent phagocytosis, and were detectable >1 year after the last immunizing dose. The data demonstrate the success of a reverse vaccinology approach to HIV vaccine design and the potential for specifically targeting sites of vulnerability with rationally-designed immunogens.

Materials and Methods for Example 10

Figure 12A:
FIGS. 12A-12C summarize the immunization regimen in rhesus macaques (i.e., non-human primates (NHP)).
Figure 12B:
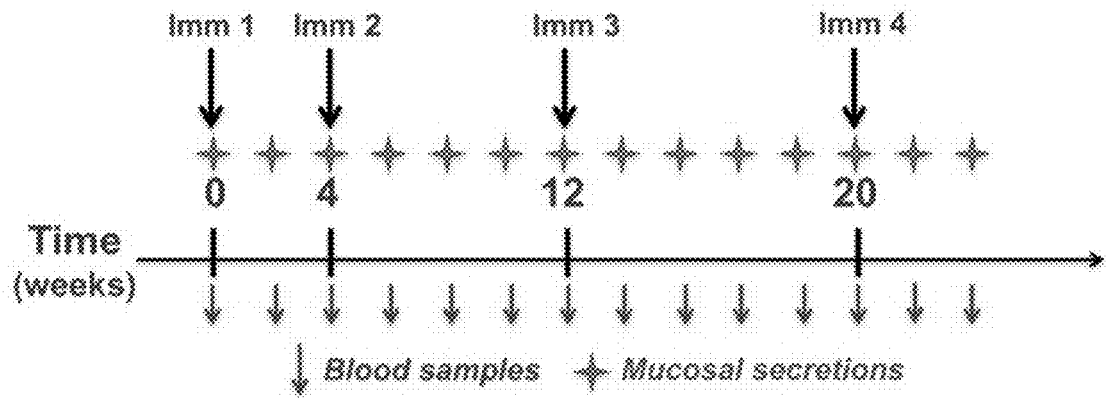
Figure 12C:
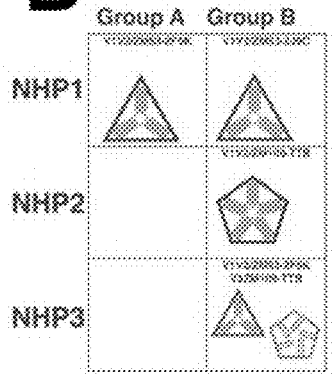

Dosing regimen in macaques. V1V2 sequences from a clade C strain of HIV-1 (ZM53) were expressed in the context of two scaffold proteins to test the immunogenicity and the ability of these epitope-scaffold immunogens to induce cross-reactive and biologically active V2 Abs in macaques. Three doses were administered to the animals consisting of clade C gp120 DNA and V1V2(ZM53)-2F5K (group 1) or V1V2(ZM53)-2J9C (group 2) at weeks 0, 4, and 12, followed by a fourth immunization at week 20 with the homologous V1V2-scaffold proteins in each group. The antibody responses were assessed at weeks 6, 14 and 22. This regimen is summarized in FIGS. 12A-12C. FIG. 12A shows the immunization regimen and schedule, and FIG. 12B shows the animal groups and immunogens used for each group as well as the icons used to represent the immunogens. FIG. 12C is a detailed list of the animal groups and immunogens used.

Luminex assay. Luminex assays were performed using a Luminex FlexMAP3D device with xPONENT 4.2 software. A total of 17 antigens, including constrained and unconstrained V1V2-scaffold proteins (bearing V1V2 inserts from a variety of HIV strains and clades), peptides, gp120 from several subtypes, and BG505 SOSIP (Sanders et al., "A Next-Generation Cleaved, Soluble HIV-1 Env Trimer, BG505 SOSIP.664 Gp140, Expresses Multiple Epitopes For Broadly Neutralizing But Not Non-Neutralizing Antibodies," *PLoS Pathog* 9:e1003618 (2013), which is hereby incorporated by reference in its entirety, were covalently coupled to carboxyl-activated xMAP beads and each bead set was mixed with animal sera diluted appropriately for titration. Biotinylated anti-monkey, anti-rabbit or anti-human IgG, and streptavidin-PE were used as secondary reagents to measure reactivity. Results were expressed as mean fluorescent intensity (MFI). Plasma samples were tested in duplicates, and a cocktail with multiple V2 and V3 and C5 mAbs was used for inter-experimental standardization. Beads coupled with BSA, and pre-bleed sera as well as PBS-TB served as negative controls.

Example 10

Figure 13:
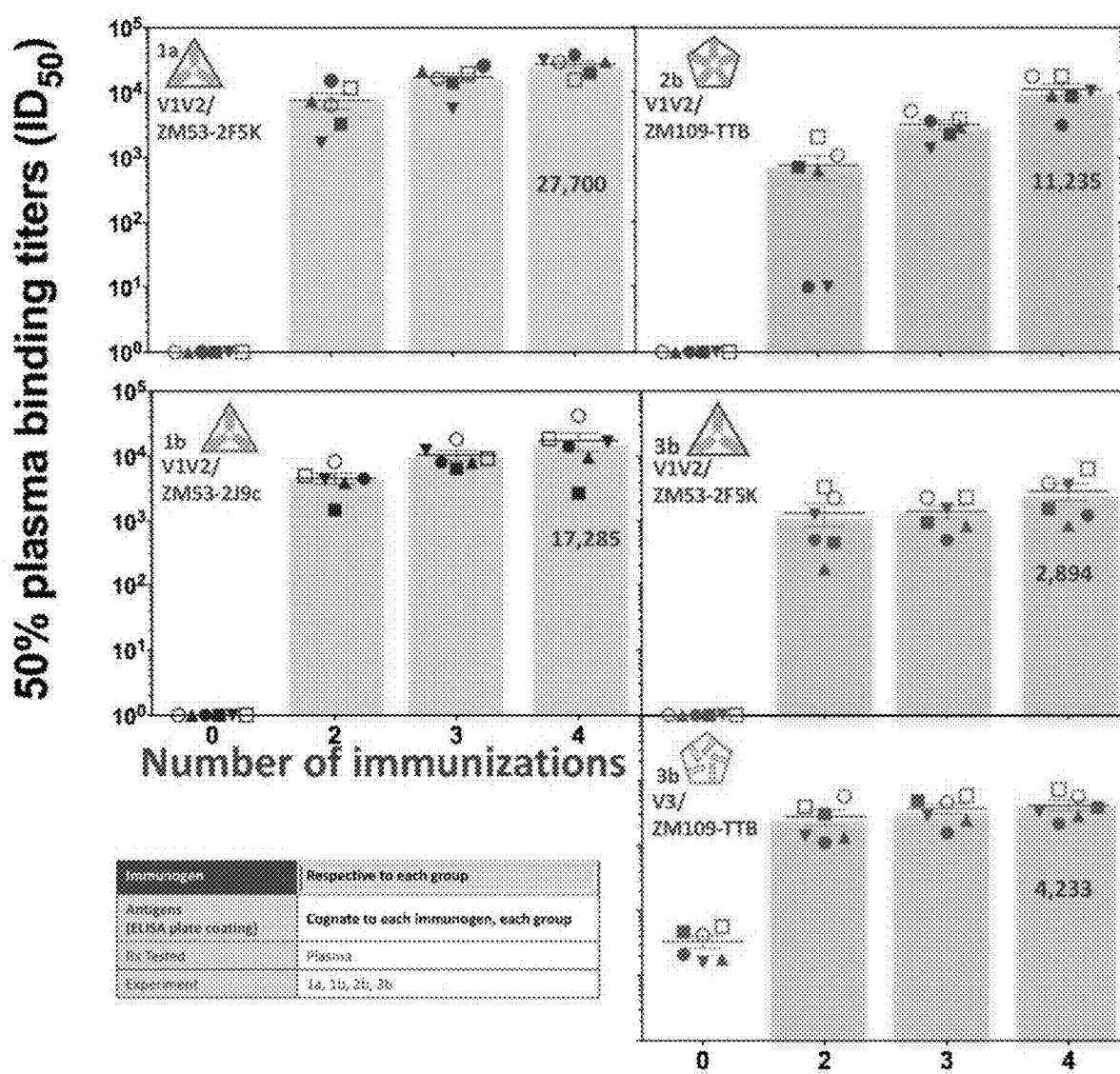
FIG. 13 shows results of antibody binding titration of non-human primate plasma in ELISA against cognate immunogens after each immunization, as noted in the table in the left lower panel. The immunogens used were: V1V2/ZM53-2F5K (also referred to herein as V1V2(ZM53)-2F5K) (Experiment Group 1a, left upper panel); V1V2/ZM53-2J9C (also referred to herein as V1V2(ZM53)-2J9C) (Experiment Group 1b, left middle panel); V1V2/ZM109-TTB (also referred to herein as V1V2(ZM109)-TTB) (Experiment Group 2b, right upper panel); and a cocktail (or combination) of V1V2/ZM53-2F5K and V3/ZM109-TTB (also referred to herein as V3(ZM109)-TTB) (Experiment Group 3b, right middle and lower panels).
Figure 14:
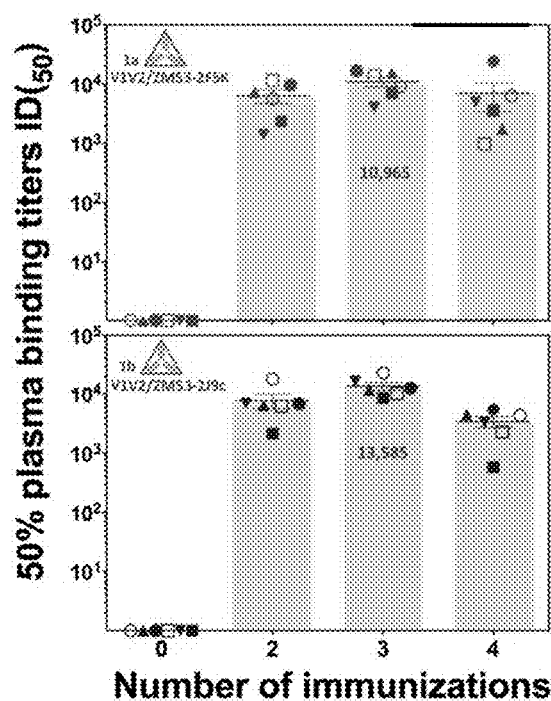
FIG. 14 shows results of antibody cross reactivity of non-human primate plasma from the two groups (Experiment Groups 1a and 1b) immunized with trimeric V1V2 scaffolds in ELISA after each immunization. The top panel shows results using V1V2/ZM53-2F5K as the immunogen (Experiment Group 1a) and the bottom panel shows results using V1V2/ZM53-2J9C as the immunogen (Experiment Group 1b).
Figure 15:
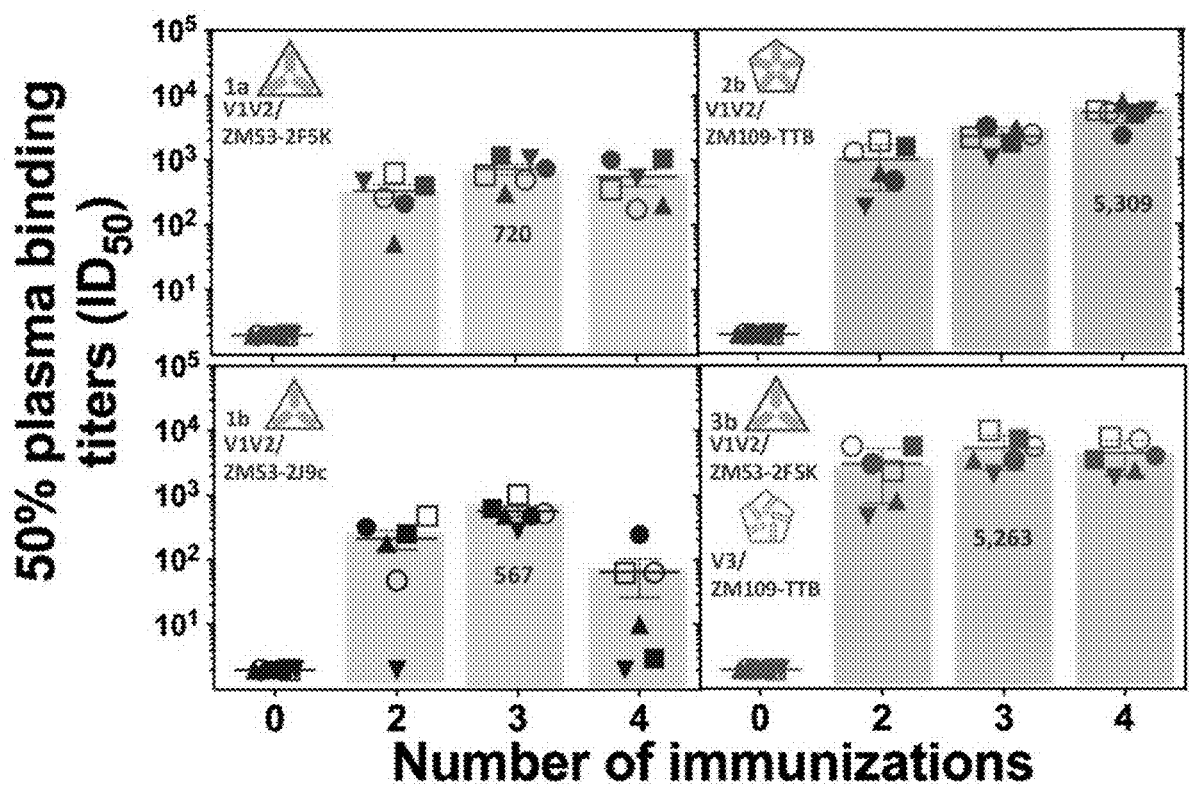
FIG. 15 shows results of antibody binding titration of non-human primate plasma in ELISA against gp120 of the clade C strain ZM109 after each immunization, as set forth in the table in the bottom panel. The immunogens used were: V1V2/ZM53-2F5K (Experiment Group 1a, left upper graph panel), V1V2/ZM53-2J9C (Experiment Group 1b, left lower graph panel), V1V2/ZM109-TTB (Experiment Group 2b, right upper graph panel), and a cocktail of V1V2/ZM53-2F5K and V3/ZM109-TTB (Experiment Group 3b, right lower graph panel).
Figure 16:
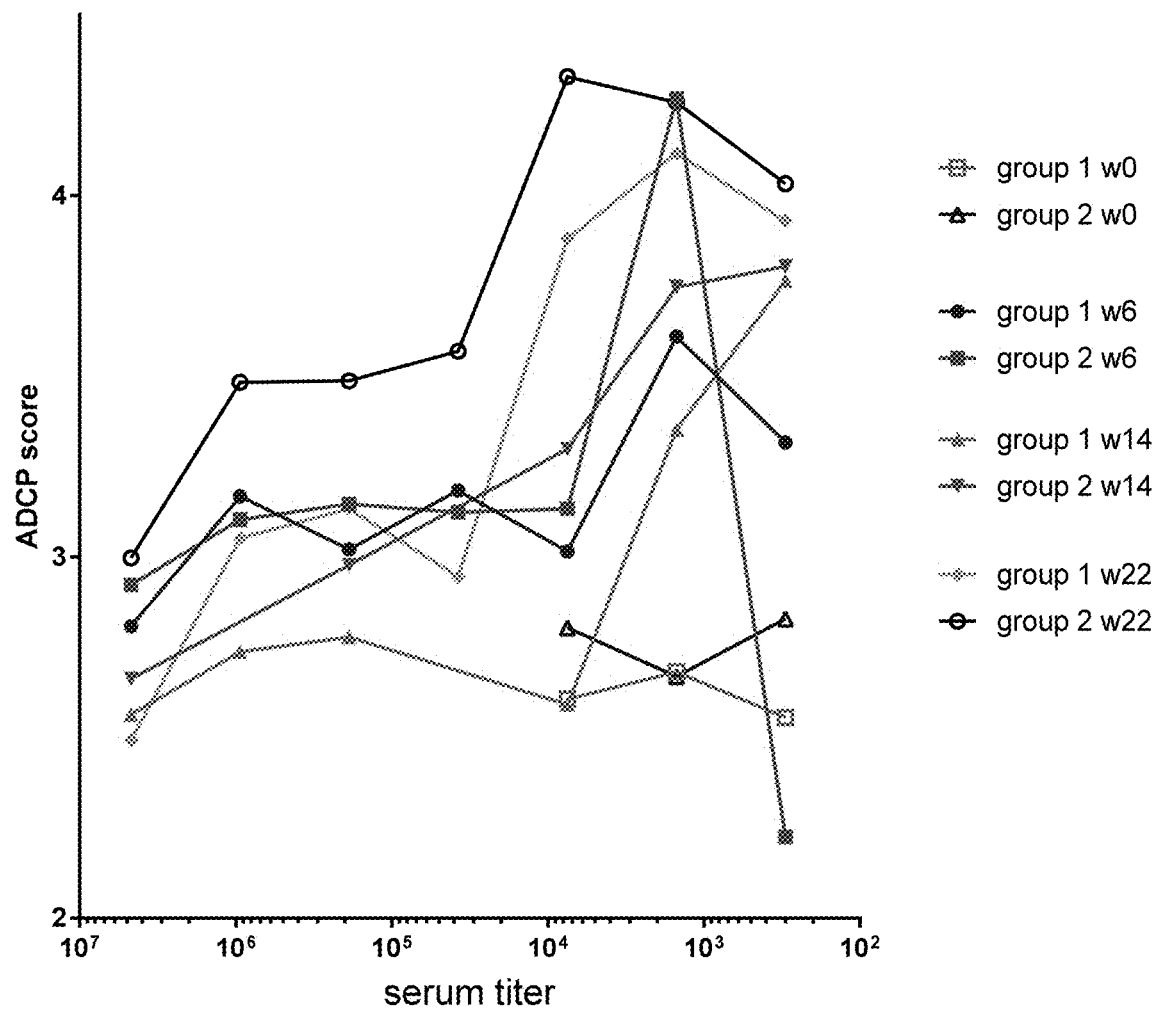
FIG. 16 shows results of antibody-dependent cellular phagocytosis (ADCP) of V1V2(ZM109)-1FD6 coated beads by sera of macaques at various time points after immunization.
Figure 17B:
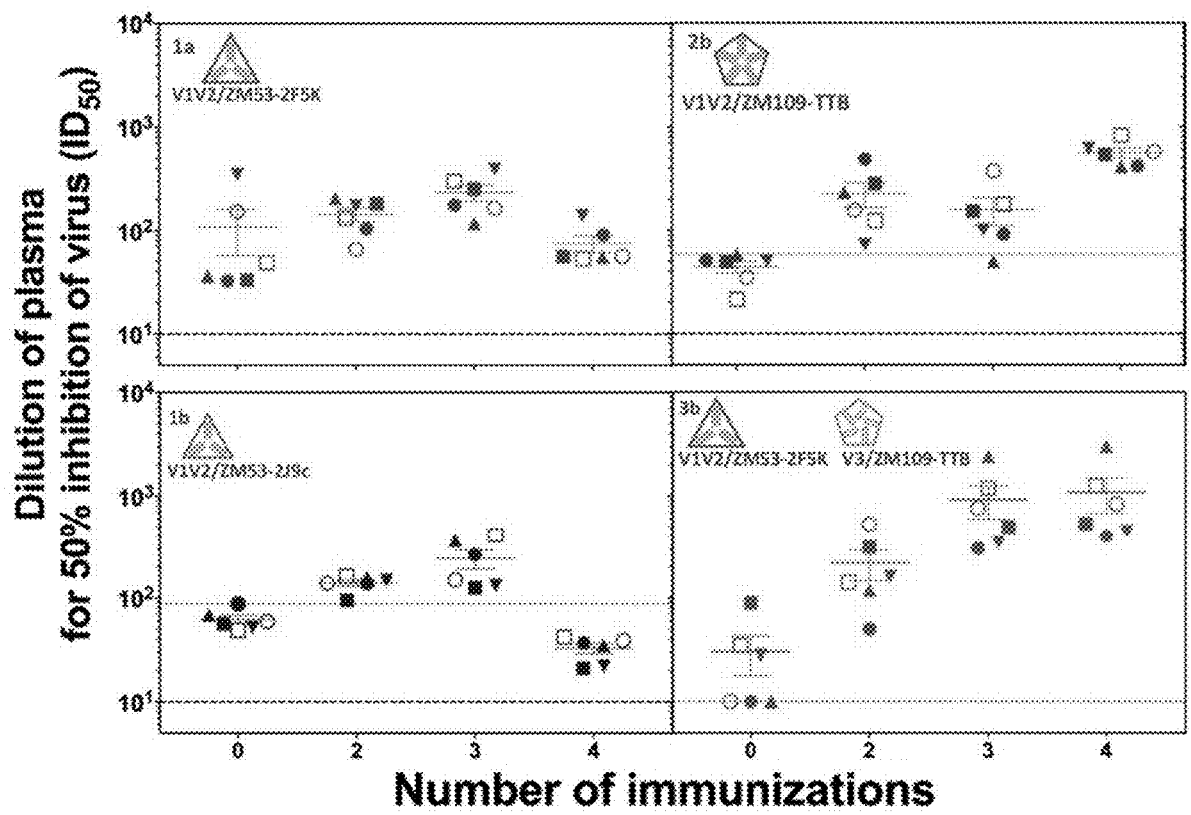
Figure 18B:
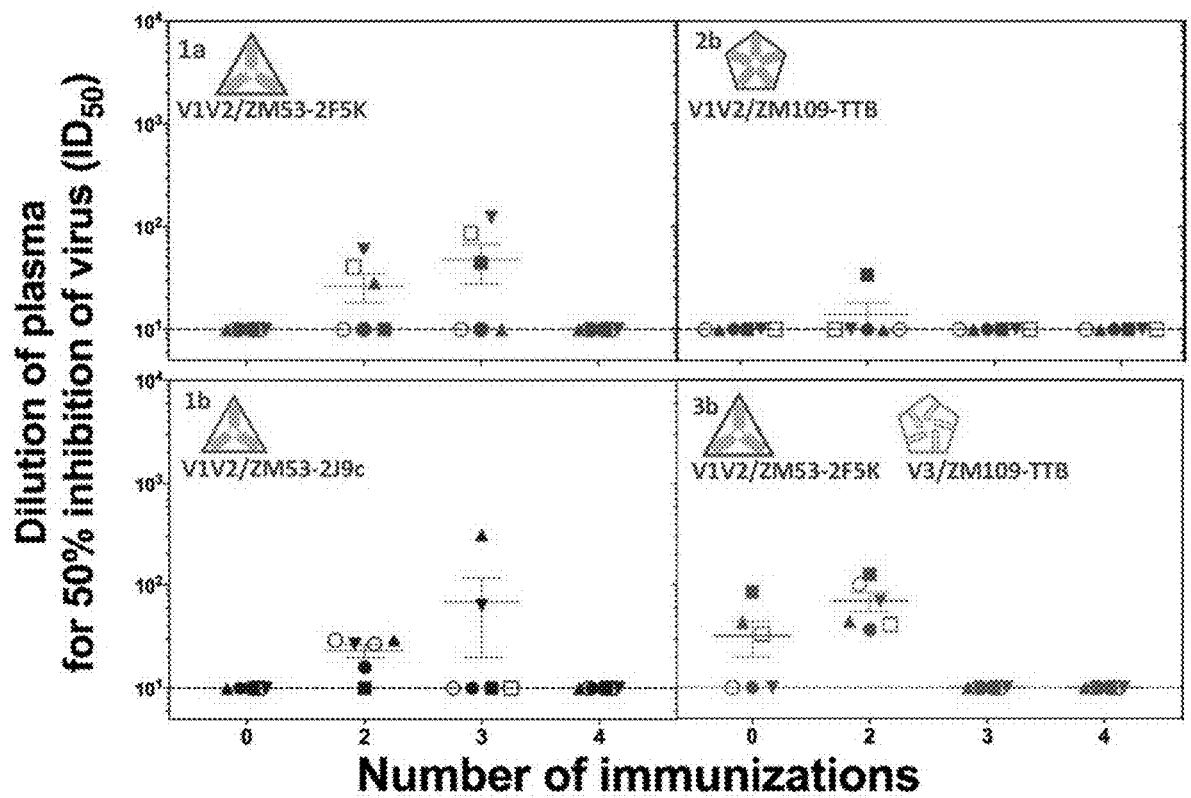
Figure 19:
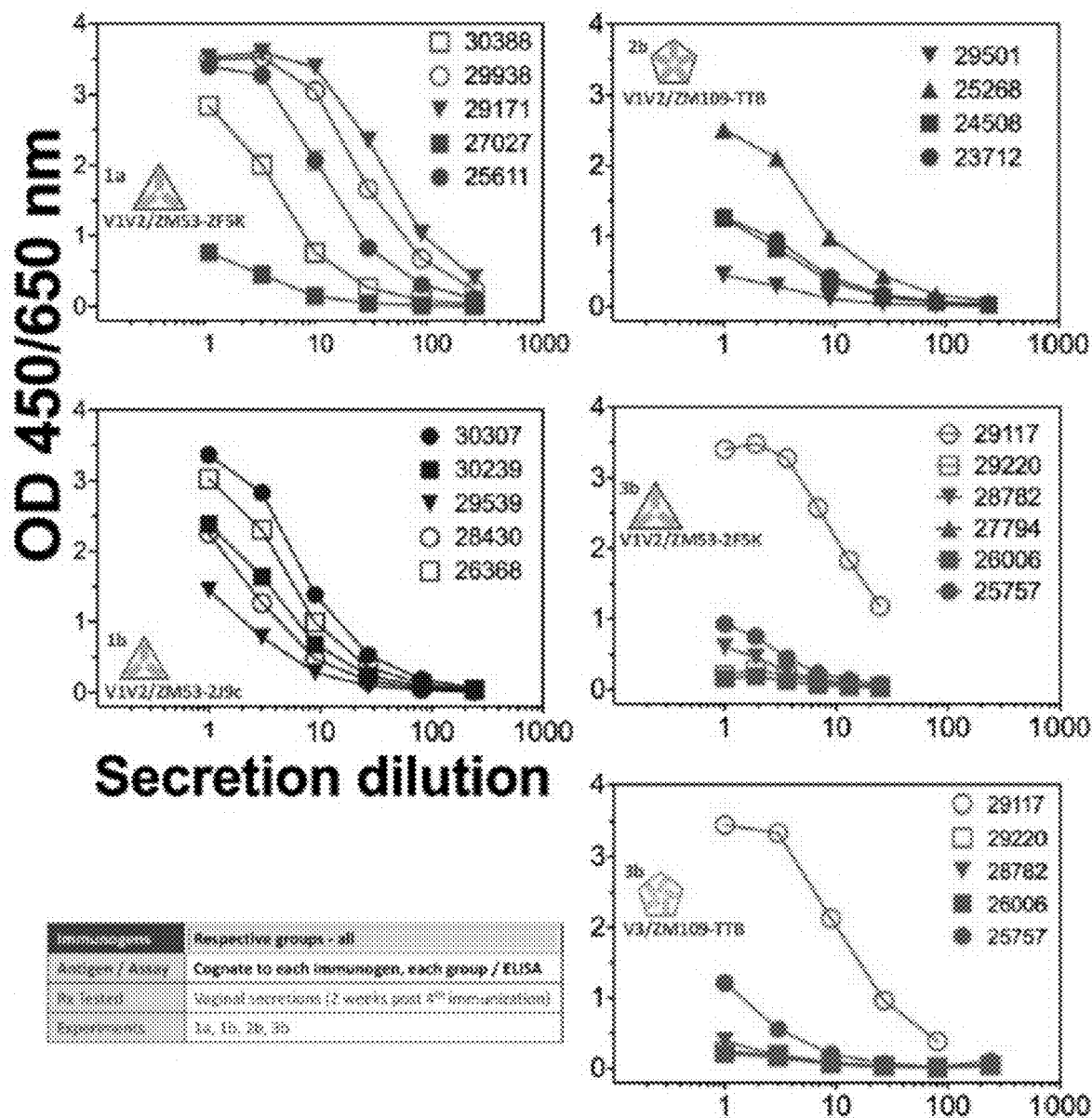
FIG. 19 shows results of antibody binding titration of non-human primate antibodies in vaginal secretions in ELISA against cognate immunogens 2 weeks post $4^{th}$ immunization, as described in the table in the lower left panel. The immunogens used were: V1V2/ZM53-2F5K (Experiment Group 1a, left upper panel), V1V2/ZM53-2J9C (Experiment Group 1b, left middle panel), V1V2/ZM109-TTB (Experiment Group 2b, right upper panel), and a cocktail of V1V2/ZM53-2F5K and V3/ZM109-TTB (Experiment Group 3b right middle and lower panels).
Figure 20:
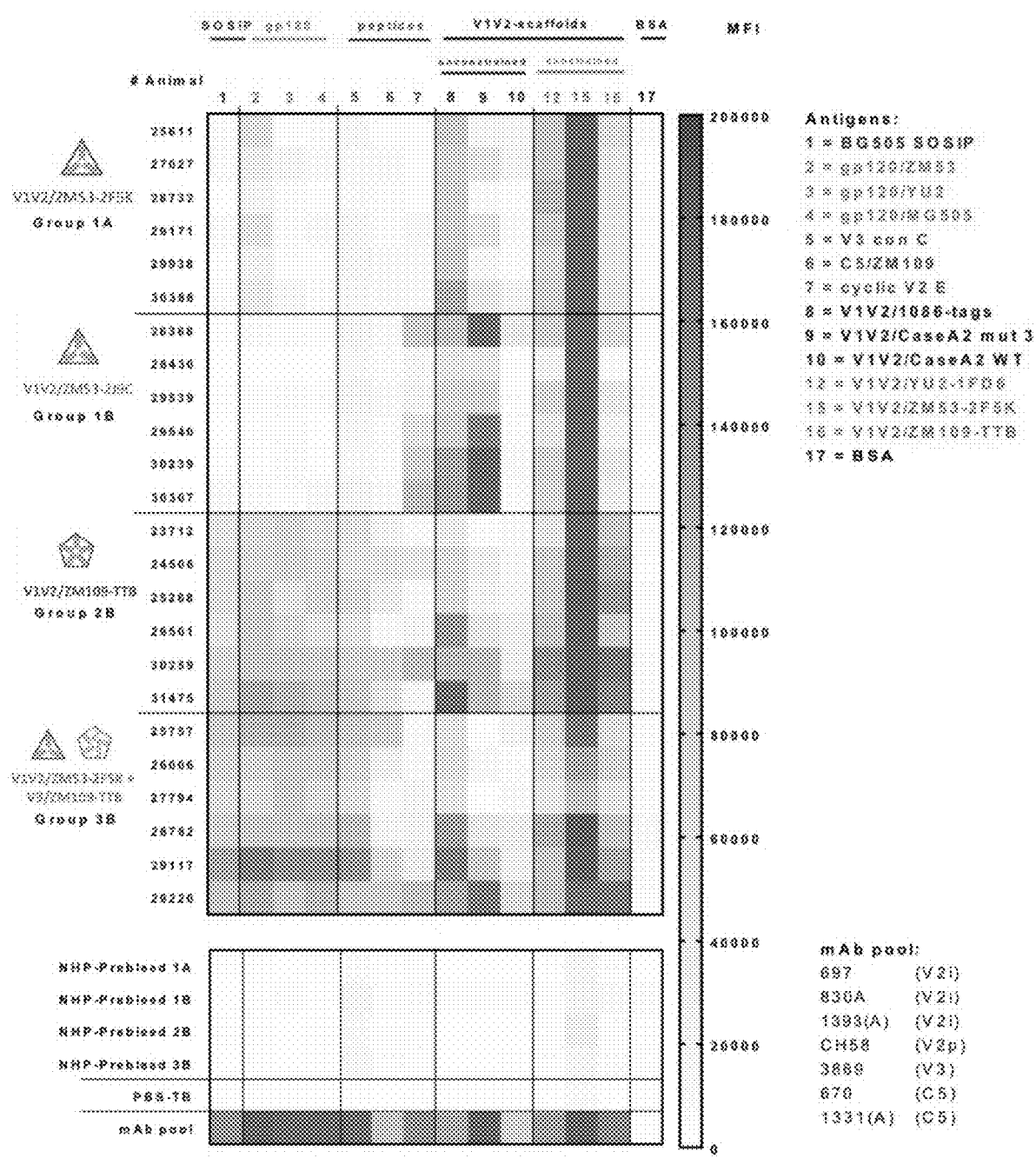
FIG. 20 shows results of antibody binding of sera from immunized non-human primates to 16 antigens and a BSA negative control (color-coded to legend on right) in a Luminex assay.

Induction of Cross-clade Reactive, Functional Antibodies with Immunogens Targeting the V2 and V3 Region of HIV The monkeys showed robust titers of serum Abs measured by ELISA against cognate immunogens (FIG. 13), and heterologous V1V2-scaffold proteins (FIG. 14). Ab responses were also detected against gp120 of the clade C strain ZM109, indicating that the vaccine-induced Abs could recognize the V1V2 regions from a clade heterologous to the clade of the immunogen (FIG. 15). The immunogen-induced Abs were shown to be functional. The sera showed Fc-receptor dependent phagocytosis, as demonstrated in FIG. 16 where maximum responses were noted at the latest time point, week 22, in both groups 1 and 2. In addition, neutralizing activity was noted at week 14 against Tier 1A and Tier 1B viruses (FIGS. 17A-17B and 18A-18B). Antibody responses recognizing the cognate immunogens were induced at mucosal surfaces (FIG. 19). A Luminex assay using a large set of antigens has shown the scaffold immunogens have induced distinct antibody responses for all macaque groups (FIG. 20).

This is the first successful example of reverse vaccinology in the HIV field in which rationally-designed epitope-scaffold immunogens induced Abs in non-human primates that recapitulate the epitope specificity of the human monoclonal Abs from which the immunogens were designed and which display biologic activities associated with protection.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An immunogenic composition comprising:
   (a) one or more pentameric structures formed from five monomeric immunogenic polypeptide subunits, each of said immunogenic polypeptide subunits of the pentameric structure comprising a first scaffold polypeptide comprising a native loop, said native loop modified to include one or more first epitopes heterologous to the first scaffold polypeptide, wherein the one or more first epitopes of said immunogenic polypeptide subunits comprise the amino acid sequence of SEQ ID NO: 1; SEQ ID NO:2; SEQ ID NO:3; SEQ ID NO:4; SEQ ID NO:5; or SEQ ID NO:26, wherein said first scaffold polypeptide directs self-assembly with four other of said scaffold polypeptides to form the pentameric structure, and wherein said pentameric structure constrains said one or more first epitopes to a conformation capable of binding a first antibody reactive to one or more native pathogen epitopes;
   (b) one or more trimeric structures formed from three monomeric immunogenic polypeptide subunits, each of said immunogenic polypeptide subunits of the trimeric structure comprising a second scaffold polypeptide comprising a hairpin loop, said hairpin loop modified to include one or more second epitopes heterologous to the second scaffold polypeptide, wherein the one or more second epitopes of said immunogenic polypeptide subunits comprise the amino acid sequence of SEQ ID NO: 1; SEQ ID NO:2; SEQ ID NO:3; SEQ ID NO:4; or SEQ ID NO:5, wherein said second scaffold polypeptide directs self-assembly with two other of said second scaffold polypeptides to form the trimeric structure, and wherein said trimeric structure constrains said one or more second epitopes to a conformation that is (i) substantially similar to one or more native pathogen epitopes in trimeric conformation and (ii) capable of binding a second antibody reactive to the one or more native pathogen epitopes in trimeric conformation; and
   (c) an immunologically and pharmaceutically acceptable vehicle or excipient.

2. The immunogenic composition of claim 1, wherein the pathogen is HIV.

3. The immunogenic composition of claim 2, wherein the first antibody is reactive to the V1 region, V2 region, V3 region, or a combination thereof of the HIV-1 surface envelope glycoprotein gp120.

4. The immunogenic composition of claim 2, wherein the second antibody is reactive to the V1 and/or V2 region of the HIV-1 surface envelope glycoprotein gp120.

5. The immunogenic composition of claim 1, wherein the first scaffold polypeptide of said one or more pentameric structures is a modified typhoid toxin subunit B ("TTB").

6. The immunogenic composition of claim 1, wherein the unmodified first scaffold polypeptide of said one or more pentameric structures comprises the amino acid sequence of SEQ ID NO:11 (TTB).

7. The immunogenic composition of claim 1, wherein each of the five monomeric immunogenic polypeptide subunits of at least one of the one or more pentameric structures comprises the amino acid sequence of SEQ ID NO:12 (V1V2(ZM109)-TTB).

8. The immunogenic composition of claim 1, wherein the second scaffold polypeptide of said one or more trimeric structures is a modified GlnK1 from Methanococcus jannaschii.

9. The immunogenic composition of claim 1, wherein the unmodified second scaffold polypeptide of said one or more trimeric structures comprises the amino acid sequence of SEQ ID NO:6 (2J9C).

10. The immunogenic composition of claim 1, wherein the second scaffold polypeptide of said one or more trimeric structures is a modified human MRG15.

11. The immunogenic composition of claim 1, wherein the unmodified second scaffold polypeptide of said one or more trimeric structures comprises the amino acid sequence of SEQ ID NO:7 (2F5K).

12. The immunogenic composition of claim 1, wherein the monomeric immunogenic polypeptide subunits of the one or more trimeric structures comprise the amino acid sequence of SEQ ID NO:8, SEQ IDNO:9, and/or SEQ ID NO:10 (V1V2(ZM53)-2F5K; V1V2(ZM53)-2J9C; and V1V2(A244)-2J9C, respectively).

13. The immunogenic composition of claim 7, wherein the monomeric immunogenic polypeptide subunits of the one or more trimeric structures comprise the amino acid sequence of SEQ ID NO:8, SEQ IDNO:9, and/or SEQ ID NO:10 (V1V2(ZM53)-2F5K; V1V2(ZM53)-2J9C; and V1V2(A244)-2J9C, respectively).

14. The immunogenic composition of claim 7, wherein the monomeric immunogenic polypeptide subunits of the one or more trimeric structures comprise the amino acid sequence of SEQ ID NO:8 (V1V2(ZM53)-2F5K).

15. The immunogenic composition of claim 7, wherein the monomeric immunogenic polypeptide subunits of the one or more trimeric structures comprise the amino acid sequence of SEQ IDNO:9 (V1V2(ZM53)-2J9C).

16. The immunogenic composition of claim 7, wherein the monomeric immunogenic polypeptide subunits of the one or more trimeric structures comprise the amino acid sequence of SEQ IDNO:10 (V1V2(A244)-2J9C).

17. The immunogenic composition of claim 7, wherein the composition comprises at least two trimeric structures and wherein the monomeric immunogenic polypeptide subunits of the at least two trimeric structures comprise the amino acid sequence of SEQ ID NO:8 and SEQ ID NO:10 (V1V2(ZM53)-2F5K and V1V2(A244)-2J9C, respectively), respectively.

18. A method of inducing, in a subject, an antibody response against a pathogen, said method comprising:
   administering to the subject the immunogenic composition of claim 1 under conditions effective to induce, in the subject, an antibody response against the pathogen.

19. An immunogenic composition comprising:
   (a) a pentameric structure formed from five monomeric immunogenic polypeptide subunits, each of said immunogenic polypeptide subunits of the pentameric structure comprising the amino acid sequence of SEQ ID NO:12 (V1V2(ZM109)-TTB);
   (b) a trimeric structure formed from three monomeric immunogenic polypeptide subunits, each of said immunogenic polypeptide subunits of the trimeric structure comprising the amino acid sequence of SEQ ID NO: 8 (V1V2(ZM53)-2F5K); and
   (c) an immunologically and pharmaceutically acceptable vehicle or excipient.

20. The immunogenic composition of claim 19, further comprising:
   (d) a second trimeric structure formed from three monomeric immunogenic polypeptide subunits, each of said immunogenic polypeptide subunits of the trimeric structure comprising the amino acid sequence of SEQ ID NO: 10 (V1V2(A244)-2J9C).

\* \* \* \* \*

SEQUENCE LISTING

```
<160> NUMBER OF SEQ ID NOS: 27

<210> SEQ ID NO 1
<211> LENGTH: 66
<212> TYPE: PRT
<213> ORGANISM: Artificial
<220> FEATURE:
<223> OTHER INFORMATION: ZM109 V1V2 amino acid sequence

<400> SEQUENCE: 1

Cys Val Thr Leu Asn Cys Thr Ser Pro Ala Ala His Asn Glu Ser Glu
1               5                   10                  15
```

```
Thr Arg Val Lys His Cys Ser Phe Asn Ile Thr Thr Asp Val Lys Asp
         20                  25                  30

Arg Lys Gln Lys Val Asn Ala Thr Phe Tyr Asp Leu Asp Ile Val Pro
         35                  40                  45

Leu Ser Ser Ser Asp Asn Ser Ser Asn Ser Ser Leu Tyr Arg Leu Ile
 50                  55                  60

Ser Cys
 65

<210> SEQ ID NO 2
<211> LENGTH: 61
<212> TYPE: PRT
<213> ORGANISM: Artificial
<220> FEATURE:
<223> OTHER INFORMATION: ZM53 V1V2 amino acid sequence

<400> SEQUENCE: 2

Cys Val Thr Leu Asn Cys Ser Lys Leu Asn Asn Ala Thr Asp Gly Glu
 1               5                  10                  15

Met Lys Asn Cys Ser Phe Asn Ala Thr Thr Glu Leu Arg Asp Lys Lys
         20                  25                  30

Lys Gln Val Tyr Ala Leu Phe Tyr Lys Leu Asp Ile Val Pro Leu Asp
         35                  40                  45

Gly Arg Asn Asn Ser Ser Glu Tyr Arg Leu Ile Asn Cys
 50                  55                  60

<210> SEQ ID NO 3
<211> LENGTH: 65
<212> TYPE: PRT
<213> ORGANISM: Artificial
<220> FEATURE:
<223> OTHER INFORMATION: 1086 V1V2 amino acid sequence

<400> SEQUENCE: 3

Cys Val Thr Leu Asn Cys Thr Asn Val Lys Gly Asn Glu Ser Asp Thr
 1               5                  10                  15

Ser Glu Val Met Lys Asn Cys Ser Phe Lys Ala Thr Thr Glu Leu Lys
         20                  25                  30

Asp Lys Lys His Lys Val His Ala Leu Phe Tyr Lys Leu Asp Val Val
         35                  40                  45

Pro Leu Asn Gly Asn Ser Ser Ser Gly Glu Tyr Arg Leu Ile Asn
 50                  55                  60

Cys
 65

<210> SEQ ID NO 4
<211> LENGTH: 66
<212> TYPE: PRT
<213> ORGANISM: Artificial
<220> FEATURE:
<223> OTHER INFORMATION: CAP45 V1V2 amino acid sequence

<400> SEQUENCE: 4

Cys Val Thr Leu Arg Cys Thr Asn Ala Thr Ile Asn Gly Ser Leu Thr
 1               5                  10                  15

Glu Glu Val Lys Asn Cys Ser Phe Asn Ile Thr Thr Glu Leu Arg Asp
         20                  25                  30

Lys Lys Gln Lys Ala Tyr Ala Leu Phe Tyr Arg Pro Asp Val Val Pro
         35                  40                  45
```

```
Leu Asn Lys Asn Ser Pro Ser Gly Asn Ser Ser Glu Tyr Ile Leu Ile
        50                  55                  60

Asn Cys
65

<210> SEQ ID NO 5
<211> LENGTH: 80
<212> TYPE: PRT
<213> ORGANISM: Artificial
<220> FEATURE:
<223> OTHER INFORMATION: A244 V1V2 amino acid sequence

<400> SEQUENCE: 5

Cys Val Thr Leu His Cys Thr Asn Ala Asn Leu Thr Lys Ala Asn Leu
1               5                   10                  15

Thr Asn Val Asn Asn Arg Thr Asn Val Ser Asn Ile Ile Gly Asn Ile
            20                  25                  30

Thr Asp Glu Val Arg Asn Cys Ser Phe Asn Met Thr Thr Glu Leu Arg
        35                  40                  45

Asp Lys Lys Gln Lys Val His Ala Leu Phe Tyr Lys Leu Asp Ile Val
    50                  55                  60

Pro Ile Glu Asp Asn Asn Asp Ser Ser Glu Tyr Arg Leu Ile Asn Cys
65                  70                  75                  80

<210> SEQ ID NO 6
<211> LENGTH: 117
<212> TYPE: PRT
<213> ORGANISM: Artificial
<220> FEATURE:
<223> OTHER INFORMATION: 2J9C Scaffold Polypeptide

<400> SEQUENCE: 6

Gly Ser Met Lys Lys Val Glu Ala Ile Ile Arg Pro Glu Lys Leu Glu
1               5                   10                  15

Ile Val Lys Lys Ala Leu Ser Asp Ala Gly Tyr Val Gly Met Thr Val
            20                  25                  30

Ser Glu Val Lys Gly Arg Gly Val Gln Gly Gly Ile Val Glu Arg Tyr
        35                  40                  45

Arg Gly Arg Glu Tyr Ile Val Asp Leu Ile Pro Lys Val Lys Ile Glu
    50                  55                  60

Leu Val Val Lys Glu Glu Asp Val Asp Asn Val Ile Asp Ile Ile Cys
65                  70                  75                  80

Glu Asn Ala Arg Thr Gly Asn Pro Gly Asp Gly Lys Ile Phe Val Ile
                85                  90                  95

Pro Val Glu Arg Val Val Arg Val Arg Thr Lys Glu Glu Gly Lys Glu
            100                 105                 110

Ala Leu Leu Glu His
        115

<210> SEQ ID NO 7
<211> LENGTH: 82
<212> TYPE: PRT
<213> ORGANISM: Artificial
<220> FEATURE:
<223> OTHER INFORMATION: 2F5K Scaffold Polypeptide

<400> SEQUENCE: 7

Pro Lys Pro Lys Phe Gln Glu Gly Glu Arg Val Leu Cys Phe His Gly
1               5                   10                  15

Pro Leu Leu Tyr Glu Ala Lys Cys Val Lys Val Ala Ile Lys Asp Lys
```

```
                    20                  25                  30

Gln Val Lys Tyr Phe Ile His Tyr Ser Gly Trp Asn Lys Asn Trp Asp
            35                  40                  45

Glu Trp Val Pro Glu Ser Arg Val Leu Lys Tyr Val Asp Thr Asn Leu
    50                  55                  60

Gln Lys Gln Arg Glu Leu Gln Lys Ala Asn Gln Glu Gln Tyr Ala Glu
65                  70                  75                  80

Gly Lys

<210> SEQ ID NO 8
<211> LENGTH: 173
<212> TYPE: PRT
<213> ORGANISM: Artificial
<220> FEATURE:
<223> OTHER INFORMATION: V1V2(ZM53)-2F5K amino acid sequence

<400> SEQUENCE: 8

Pro Lys Pro Lys Phe Gln Glu Gly Glu Arg Val Leu Cys Phe His Gly
1               5                   10                  15

Pro Leu Leu Tyr Glu Ala Lys Cys Val Lys Val Ala Ile Leu Ala Ala
                20                  25                  30

Cys Val Thr Leu Asn Cys Ser Lys Leu Asn Asn Ala Thr Asp Gly Glu
            35                  40                  45

Met Lys Asn Cys Ser Phe Asn Ala Thr Thr Glu Leu Arg Asp Lys Lys
    50                  55                  60

Lys Gln Val Tyr Ala Leu Phe Tyr Lys Leu Asp Ile Val Pro Leu Asp
65                  70                  75                  80

Gly Arg Asn Asn Ser Ser Glu Tyr Arg Leu Ile Asn Cys Glu Glu Thr
                85                  90                  95

Val Lys Tyr Phe Ile His Tyr Ser Gly Trp Asn Lys Asn Trp Asp Glu
                100                 105                 110

Trp Val Pro Glu Ser Arg Val Leu Lys Tyr Val Asp Thr Asn Leu Gln
            115                 120                 125

Lys Gln Arg Glu Leu Gln Lys Ala Asn Gln Glu Gln Tyr Ala Glu Gly
        130                 135                 140

Lys Gly Leu Glu Val Leu Phe Gln Gly Pro Gly His His His His His
145                 150                 155                 160

His His His Ser Ala Trp Ser His Pro Gln Phe Glu Lys
                165                 170

<210> SEQ ID NO 9
<211> LENGTH: 204
<212> TYPE: PRT
<213> ORGANISM: Artificial
<220> FEATURE:
<223> OTHER INFORMATION: V1V2(ZM53)-2J9C amino acid sequence

<400> SEQUENCE: 9

Gly Ser Met Lys Lys Val Glu Ala Ile Ile Arg Pro Glu Lys Leu Glu
1               5                   10                  15

Ile Val Lys Lys Ala Leu Ser Asp Ala Gly Tyr Val Gly Met Thr Val
                20                  25                  30

Ser Glu Val Lys Gly Arg Gly Val Gln Gly Gly Ile Val Glu Arg Tyr
            35                  40                  45

Cys Val Thr Leu Asn Cys Ser Lys Leu Asn Asn Ala Thr Asp Gly Glu
    50                  55                  60

Met Lys Asn Cys Ser Phe Asn Ala Thr Thr Glu Leu Arg Asp Lys Lys
```

```
                65                  70                  75                  80
Lys Gln Val Tyr Ala Leu Phe Tyr Lys Leu Asp Ile Val Pro Leu Asp
                    85                  90                  95

Gly Arg Asn Asn Ser Ser Glu Tyr Arg Leu Ile Asn Cys Arg Glu Tyr
                100                 105                 110

Ile Val Asp Leu Ile Pro Lys Val Lys Ile Glu Leu Val Val Lys Glu
                115                 120                 125

Glu Asp Val Asp Asn Val Ile Asp Ile Ile Cys Glu Asn Ala Arg Thr
                130                 135                 140

Gly Asp Pro Gly Asp Gly Lys Ile Phe Val Ile Pro Val Glu Arg Val
145                 150                 155                 160

Val Arg Val Arg Thr Lys Glu Glu Gly Lys Glu Ala Leu Leu Glu His
                165                 170                 175

Gly Leu Glu Val Leu Phe Gln Gly Pro Gly His His His His His His
                180                 185                 190

His His Ser Ala Trp Ser His Pro Gln Phe Glu Lys
                195                 200

<210> SEQ ID NO 10
<211> LENGTH: 223
<212> TYPE: PRT
<213> ORGANISM: Artificial
<220> FEATURE:
<223> OTHER INFORMATION: V1V2(A244)-2J9C amino acid sequence

<400> SEQUENCE: 10

Gly Ser Met Lys Lys Val Glu Ala Ile Ile Arg Pro Glu Lys Leu Glu
1               5                   10                  15

Ile Val Lys Lys Ala Leu Ser Asp Ala Gly Tyr Val Gly Met Thr Val
                20                  25                  30

Ser Glu Val Lys Gly Arg Gly Val Gln Gly Gly Ile Val Glu Arg Tyr
                35                  40                  45

Cys Val Thr Leu His Cys Thr Asn Ala Asn Leu Thr Lys Ala Asn Leu
                50                  55                  60

Thr Asn Val Asn Asn Arg Thr Asn Val Ser Asn Ile Ile Gly Asn Ile
65                  70                  75                  80

Thr Asp Glu Val Arg Asn Cys Ser Phe Asn Met Thr Thr Glu Leu Arg
                85                  90                  95

Asp Lys Lys Gln Lys Val His Ala Leu Phe Tyr Lys Leu Asp Ile Val
                100                 105                 110

Pro Ile Glu Asp Asn Asn Asp Ser Ser Glu Tyr Arg Leu Ile Asn Cys
                115                 120                 125

Arg Glu Tyr Ile Val Asp Leu Ile Pro Lys Val Lys Ile Glu Leu Val
                130                 135                 140

Val Lys Glu Glu Asp Val Asp Asn Val Ile Asp Ile Ile Cys Glu Asn
145                 150                 155                 160

Ala Arg Thr Gly Asp Pro Gly Asp Gly Lys Ile Phe Val Ile Pro Val
                165                 170                 175

Glu Arg Val Val Arg Val Arg Thr Lys Glu Glu Gly Lys Glu Ala Leu
                180                 185                 190

Leu Glu His Gly Leu Glu Val Leu Phe Gln Gly Pro Gly His His His
                195                 200                 205

His His His His Ser Ala Trp Ser His Pro Gln Phe Glu Lys
                210                 215                 220
```

<210> SEQ ID NO 11
<211> LENGTH: 114
<212> TYPE: PRT
<213> ORGANISM: Artificial
<220> FEATURE:
<223> OTHER INFORMATION: TTB Scaffold Polypeptide

<400> SEQUENCE: 11

```
Glu Trp Thr Gly Asp Asn Thr Asn Ala Tyr Tyr Ser Asp Glu Val Ile
1               5                   10                  15
Ser Glu Leu His Val Gly Gln Ile Asp Thr Ser Pro Tyr Phe Cys Ile
            20                  25                  30
Lys Thr Val Lys Ala Asn Gly Ser Gly Thr Pro Val Val Ala Cys Ala
        35                  40                  45
Val Ser Lys Gln Ser Ile Trp Ala Pro Ser Phe Lys Glu Leu Leu Asp
    50                  55                  60
Gln Ala Arg Tyr Phe Tyr Ser Thr Gly Gln Ser Val Arg Ile His Val
65                  70                  75                  80
Gln Lys Asn Ile Trp Thr Tyr Pro Leu Phe Val Asn Thr Phe Ser Ala
                85                  90                  95
Asn Ala Leu Val Gly Leu Ser Ser Cys Ser Ala Thr Gln Cys Phe Gly
            100                 105                 110
Pro Lys
```

<210> SEQ ID NO 12
<211> LENGTH: 217
<212> TYPE: PRT
<213> ORGANISM: Artificial
<220> FEATURE:
<223> OTHER INFORMATION: V1V2(ZM109)-TTB amino acid sequence

<400> SEQUENCE: 12

```
Glu Trp Thr Gly Asp Asn Thr Asn

Ala Trp Ser His Pro Gln Phe Glu Lys
            210                 215

<210> SEQ ID NO 13
<211> LENGTH: 62
<212> TYPE: PRT
<213> ORGANISM: Artificial
<220> FEATURE:
<223> OTHER INFORMATION: V1V2 consensus amino acid sequence

<400> SEQUENCE: 13

Cys Val Thr Leu Asn Cys Thr Asp Val Asn Ala Thr Asn Asn Thr Thr
1               5                   10                  15

Asn Asn Glu Glu Ile Lys Asn Cys Ser Phe Asn Ile Thr Thr Glu Ile
            20                  25                  30

Arg Asp Lys Lys Lys Val Tyr Ala Leu Phe Tyr Lys Leu Asp Val
        35                  40                  45

Val Pro Ile Asp Asp Asn Ser Tyr Arg Leu Ile Asn Cys
    50                  55                  60

<210> SEQ ID NO 14
<211> LENGTH: 170
<212> TYPE: PRT
<213> ORGANISM: Artificial
<220> FEATURE:
<223> OTHER INFORMATION: V3(ZM109)-TTB amino acid sequence

<400> SEQUENCE: 14

Glu Trp Thr Gly Asp Asn Thr Asn Ala Tyr Tyr Ser Ala Glu Val Ile
1               5                   10                  15

Ser Glu Leu His Val Gly Gln Ile Asp Thr Ser Pro Tyr Phe Cys Ile
            20                  25                  30

Lys Thr Val Lys Ala Asn Gly Ala Gly Thr Pro Val Val Ala Cys Ala
        35                  40                  45

Val Ser Lys Gln Ser Ile Trp Ala Pro Ser Phe Lys Glu Leu Leu Asp
    50                  55                  60

Gln Ala Arg Tyr Phe Tyr Ser Thr Gly Gln Ser Val Arg Ile His Val
65                  70                  75                  80

Gln Lys Asn Ile Trp Thr Tyr Pro Leu Phe Val Asn Thr Phe Ser Ala
                85                  90                  95

Asn Ala Leu Val Gly Leu Ser Ser Cys Ile Arg Pro Gly Asn Asn Thr
            100                 105                 110

Arg Lys Ser Ile Arg Leu Gly Pro Gly Gln Thr Phe Tyr Ala Thr Gly
        115                 120                 125

Asp Val Ile Gly Asp Ile Arg Lys Ala Tyr Cys Phe Gly Pro Lys Leu
    130                 135                 140

Glu Val Leu Phe Gln Gly Pro Gly His His His His His His
145                 150                 155                 160

Ser Ala Trp Ser His Pro Gln Phe Glu Lys
                165                 170

<210> SEQ ID NO 15
<211> LENGTH: 519
<212> TYPE: DNA
<213> ORGANISM: Artificial
<220> FEATURE:
<223> OTHER INFORMATION: Nucleotide sequence encoding V1V2(ZM53)-2F5K

<400> SEQUENCE: 15

```
ccgaagccta aattccagga gggtgagcga gtgctgtgct ttcatgggcc tcttctttat      60
gaagcaaagt gtgtaaaggt tgccatactg gccgcctgcg tgaccctgaa ctgcagcaag     120
ctgaacaacg ccaccgacgg cgagatgaag aactgcagct tcaacgccac caccgagctg     180
agagacaaga agaagcaggt gtacgccctg ttctacaagc tggacatcgt gcccctggac     240
ggcagaaaca acagcagcga gtacagactg atcaactgcg aggagaccgt gaaatacttc     300
atacattaca gtggttggaa taaaaattgg gatgaatggg ttccggagag cagagtactc     360
aaatacgtgg acaccaattt gcagaaacag cgagaacttc aaaaagccaa tcaggagcag     420
tatgcagagg ggaagggcct ggaagtgctg ttccagggcc caggccacca ccatcaccat     480
catcaccaca gcgcctggtc ccaccccag  ttcgagaag                             519
```

```
<210> SEQ ID NO 16
<211> LENGTH: 612
<212> TYPE: DNA
<213> ORGANISM: Artificial
<220> FEATURE:
<223> OTHER INFORMATION: Nucleotide sequence encoding V1V2(ZM53)-2J9C

<400> SEQUENCE: 16
ggcagcatga agaaggtgga ggccatcatc agacccgaga agctggagat cgtgaagaag      60
gccctgagcg acgccggcta cgtgggcatg accgtgagcg aggtgaaggg cagaggcgtg     120
cagggcggca tcgtggagag atactgcgtg accctgaact gcagcaagct gaacaacgcc     180
accgacggcg agatgaagaa ctgcagcttc aacgccacca ccgagctgag agacaagaag     240
aagcaggtgt acgccctgtt ctacaagctg gacatcgtgc ccctggacgg cagaaacaac     300
agcagcgagt acagactgat caactgcaga gagtacatcg tggacctgat ccccaaggtg     360
aagatcgagc tggtggtgaa ggaggaggac gtggacaacg tgatcgacat catctgcgag     420
aacgccagaa ccggcgaccc cggcgacggc aagatcttcg tgatccccgt ggagagagtg     480
gtgagagtga gaaccaagga ggagggcaag gaggccctgc tggagcacgg cctggaagtg     540
ctgttccagg gcccaggcca ccaccatcac catcatcacc acagcgcctg gtcccacccc     600
cagttcgaga ag                                                         612
```

```
<210> SEQ ID NO 17
<211> LENGTH: 669
<212> TYPE: DNA
<213> ORGANISM: Artificial
<220> FEATURE:
<223> OTHER INFORMATION: Nucleotide sequence encoding V1V2(A244)-2J9C

<400> SEQUENCE: 17
ggcagcatga agaaggtgga ggccatcatc agacccgaga agctggagat cgtgaagaag      60
gccctgagcg acgccggcta cgtgggcatg accgtgagcg aggtgaaggg cagaggcgtg     120
cagggcggca tcgtggagag atactgcgtg accctgcact gcaccaacgc caacctgacc     180
aaggccaacc tgaccaacgt gaacaacaga accaacgtga gcaacatcat cggcaacatc     240
accgacgagt gagaaactg cagcttcaac atgaccaccg agctgagaga caagaagcag     300
aaggtgcacg ccctgttcta caagctggac atcgtgccca tcgaggacaa caacgacagc     360
agcgagtaca gactgatcaa ctgcagagag tacatcgtgg acctgatccc caaggtgaag     420
atcgagctgg tggtgaagga ggaggacgtg gacaacgtga tcgacatcat ctgcgagaac     480
gccagaaccg gcgaccccgg cgacggcaag atcttcgtga tccccgtgga gagagtggtg     540
```

```
agagtgagaa ccaaggagga gggcaaggag gccctgctgg agcacggcct ggaagtgctg    600
ttccagggcc caggccacca ccatcaccat catcaccaca gcgcctggtc ccaccccag    660 ttcgagaag                                                            669
```

```
<210> SEQ ID NO 18
<211> LENGTH: 75
<212> TYPE: PRT
<213> ORGANISM: Artificial
<220> FEATURE:
<223> OTHER INFORMATION: 92TH023(E)V1V2 amino acid sequence

<400> SEQUENCE: 18

Cys Val Thr Leu Asn Cys Thr Asn Ala Asn Val Thr Asn Val Lys Asn
1               5                   10                  15

Ile Thr Asn Val Pro Asn Ile Ile Gly Asn Ile Thr Asp Glu Val Arg
            20                  25                  30

Asn Cys Ser Phe Asn Met Thr Thr Glu Leu Arg Asp Lys Lys Gln Lys
        35                  40                  45

Val His Ala Leu Phe Tyr Lys Leu Asp Ile Val Pro Ile Glu Asp Asn
    50                  55                  60

Thr Ser Ser Ser Glu Tyr Arg Leu Ile Asn Cys
65                  70                  75
```

```
<210> SEQ ID NO 19
<211> LENGTH: 82
<212> TYPE: PRT
<213> ORGANISM: Artificial
<220> FEATURE:
<223> OTHER INFORMATION: Case A2(B) V1V2 amino acid sequence

<400> SEQUENCE: 19

Cys Val Thr Leu Asn Cys Ile Asp Leu Arg Asn Ala Thr Asn Ala Thr
1               5                   10                  15

Ser Asn Ser Asn Thr Thr Asn Thr Thr Ser Ser Ser Gly Gly Leu Met
            20                  25                  30

Met Glu Gln Gly Glu Ile Lys Asn Cys Ser Phe Asn Ile Thr Thr Ser
        35                  40                  45

Ile Arg Asp Lys Val Gln Lys Glu Tyr Ala Leu Phe Tyr Lys Leu Asp
    50                  55                  60

Ile Val Pro Ile Asp Asn Pro Lys Asn Ser Thr Asn Tyr Arg Leu Ile
65                  70                  75                  80

Ser Cys
```

```
<210> SEQ ID NO 20
<211> LENGTH: 68
<212> TYPE: PRT
<213> ORGANISM: Artificial
<220> FEATURE:
<223> OTHER INFORMATION: YU2(B) V1V2 amino acid sequence

<400> SEQUENCE: 20

Cys Val Thr Leu Asn Cys Thr Asp Leu Arg Asn Ala Thr Asn Thr Thr
1               5                   10                  15

Ser Ser Ser Trp Glu Thr Met Glu Lys Gly Glu Ile Lys Asn Cys Ser
            20                  25                  30

Phe Asn Ile Thr Thr Ser Ile Arg Asp Lys Val Gln Lys Glu Tyr Ala
        35                  40                  45

Leu Phe Tyr Asn Leu Asp Val Val Pro Ile Asp Asn Ala Ser Tyr Arg
    50                  55                  60
```

Leu Ile Ser Cys
65

<210> SEQ ID NO 21
<211> LENGTH: 42
<212> TYPE: PRT
<213> ORGANISM: Artificial
<220> FEATURE:
<223> OTHER INFORMATION: cV2 peptide 92TH023(E) amino acid sequence

<400> SEQUENCE: 21

Cys Ser Phe Asn Met Thr Thr Glu Leu Arg Asp Lys Lys Gln Lys Val
1               5                   10                  15

His Ala Leu Phe Tyr Lys Leu Asp Ile Val Pro Ile Glu Asp Asn Thr
            20                  25                  30

Ser Ser Ser Glu Tyr Arg Leu Ile Asn Cys
        35                  40

<210> SEQ ID NO 22
<211> LENGTH: 352
<212> TYPE: PRT
<213> ORGANISM: Artificial
<220> FEATURE:
<223> OTHER INFORMATION: V1V2(ZM109)-1FD6-Fc amino acid sequence

<400> SEQUENCE: 22

Met Thr Thr Phe Lys Leu Ala Ala Cys Val Thr Leu Asn Cys Thr Ser
1               5                   10                  15

Pro Ala Ala His Asn Glu Ser Glu Thr Arg Val Lys His Cys Ser Phe
            20                  25                  30

Asn Ile Thr Thr Asp Val Lys Asp Arg Lys Gln Lys Val Asn Ala Thr
            35                  40                  45

Phe Tyr Asp Leu Asp Ile Val Pro Leu Ser Ser Ser Asp Asn Ser Ser
        50                  55                  60

Asn Ser Ser Leu Tyr Arg Leu Ile Ser Cys Gln Thr Thr Thr Thr Glu
65                  70                  75                  80

Ala Val Asp Ala Ala Thr Ala Ala Lys Val Phe Lys Gln Tyr Ala Asn
                85                  90                  95

Asp Asn Gly Ile Asp Gly Glu Trp Thr Tyr Asp Asp Ala Thr Lys Thr
            100                 105                 110

Phe Thr Val Thr Glu Gly Leu Glu Val Leu Phe Gln Gly Ala Ser Gly
            115                 120                 125

Gly Ser Lys Pro Thr Cys Pro Pro Pro Glu Leu Leu Gly Gly Pro Ser
        130                 135                 140

Val Phe Ile Phe Pro Pro Lys Pro Lys Asp Thr Leu Met Ile Ser Arg
145                 150                 155                 160

Thr Pro Glu Val Thr Cys Val Val Asp Val Ser Gln Asp Asp Pro
                165                 170                 175

Glu Val Gln Phe Thr Trp Tyr Ile Asn Asn Glu Gln Val Arg Thr Ala
            180                 185                 190

Arg Pro Pro Leu Arg Glu Gln Gln Phe Asn Ser Thr Ile Arg Val Val
        195                 200                 205

Ser Thr Leu Pro Ile Ala His Gln Asp Trp Leu Arg Gly Lys Glu Phe
    210                 215                 220

Lys Cys Lys Val His Asn Lys Ala Leu Pro Ala Pro Ile Glu Lys Thr
225                 230                 235                 240

Ile Ser Lys Ala Arg Gly Gln Pro Leu Glu Pro Lys Val Tyr Thr Met

```
                        245                 250                 255
Gly Pro Pro Arg Glu Glu Leu Ser Ser Arg Ser Val Ser Leu Thr Cys
                260                 265                 270

Met Ile Asn Gly Phe Tyr Pro Ser Asp Ile Ser Val Glu Trp Glu Lys
            275                 280                 285

Asn Gly Lys Ala Glu Asp Asn Tyr Lys Thr Thr Pro Ala Val Leu Asp
        290                 295                 300

Ser Asp Gly Ser Tyr Phe Leu Tyr Ser Lys Leu Ser Val Pro Thr Ser
305                 310                 315                 320

Glu Trp Gln Arg Gly Asp Val Phe Thr Cys Ser Val Met His Glu Ala
                325                 330                 335

Leu His Asn His Tyr Thr Gln Lys Ser Ile Ser Arg Ser Pro Gly Lys
            340                 345                 350

<210> SEQ ID NO 23
<211> LENGTH: 317
<212> TYPE: PRT
<213> ORGANISM: Artificial
<220> FEATURE:
<223> OTHER INFORMATION: V1V2(1086)-Fc amino acid sequence

<400> SEQUENCE: 23

Ser Leu Lys Pro Cys Val Lys Leu Thr Pro Leu Cys Val Thr Leu Asn
1               5                   10                  15

Cys Thr Asn Val Lys Gly Asn Glu Ser Asp Thr Ser Glu Val Met Lys
            20                  25                  30

Asn Cys Ser Phe Lys Ala Thr Thr Glu Leu Lys Asp Lys Lys His Lys
        35                  40                  45

Val His Ala Leu Phe Tyr Lys Leu Asp Val Val Pro Leu Asn Gly Asn
    50                  55                  60

Ser Ser Ser Ser Gly Glu Tyr Arg Leu Ile Asn Cys Asn Thr Ser Ala
65                  70                  75                  80

Ile Thr Gln Ala Cys Pro Lys Val Ser Gly Ala Ser Gly Gly Ser Lys
                85                  90                  95

Pro Thr Cys Pro Pro Pro Glu Leu Leu Gly Gly Pro Ser Val Phe Ile
            100                 105                 110

Phe Pro Pro Lys Pro Lys Asp Thr Leu Met Ile Ser Arg Thr Pro Glu
        115                 120                 125

Val Thr Cys Val Val Val Asp Val Ser Gln Asp Asp Pro Glu Val Gln
    130                 135                 140

Phe Thr Trp Tyr Ile Asn Asn Glu Gln Val Arg Thr Ala Arg Pro Pro
145                 150                 155                 160

Leu Arg Glu Gln Gln Phe Asn Ser Thr Ile Arg Val Val Ser Thr Leu
                165                 170                 175

Pro Ile Ala His Gln Asp Trp Leu Arg Gly Lys Glu Phe Lys Cys Lys
            180                 185                 190

Val His Asn Lys Ala Leu Pro Ala Pro Ile Glu Lys Thr Ile Ser Lys
        195                 200                 205

Ala Arg Gly Gln Pro Leu Glu Pro Lys Val Tyr Thr Met Gly Pro Pro
    210                 215                 220

Arg Glu Glu Leu Ser Ser Arg Ser Val Ser Leu Thr Cys Met Ile Asn
225                 230                 235                 240

Gly Phe Tyr Pro Ser Asp Ile Ser Val Glu Trp Glu Lys Asn Gly Lys
                245                 250                 255

Ala Glu Asp Asn Tyr Lys Thr Thr Pro Ala Val Leu Asp Ser Asp Gly
```

```
                260                 265                 270
Ser Tyr Phe Leu Tyr Ser Lys Leu Ser Val Pro Thr Ser Glu Trp Gln
                275                 280                 285

Arg Gly Asp Val Phe Thr Cys Ser Val Met His Glu Ala Leu His Asn
290                 295                 300

His Tyr Thr Gln Lys Ser Ile Ser Arg Ser Pro Gly Lys
305                 310                 315

<210> SEQ ID NO 24
<211> LENGTH: 318
<212> TYPE: PRT
<213> ORGANISM: Artificial
<220> FEATURE:
<223> OTHER INFORMATION: V1V2(ZM109)-Fc amino acid sequence

<400> SEQUENCE: 24

Ser Leu Lys Pro Cys Val Lys Leu Thr Pro Leu Cys Val Thr Leu Asn
1               5                   10                  15

Cys Thr Ser Pro Ala Ala His Asn Glu Ser Glu Thr Arg Val Lys His
                20                  25                  30

Cys Ser Phe Asn Ile Thr Thr Asp Val Lys Asp Arg Lys Gln Lys Val
                35                  40                  45

Asn Ala Thr Phe Tyr Asp Leu Asp Ile Val Pro Leu Ser Ser Ser Asp
50                  55                  60

Asn Ser Ser Asn Ser Ser Leu Tyr Arg Leu Ile Ser Cys Asn Thr Ser
65                  70                  75                  80

Thr Ile Thr Gln Ala Cys Pro Lys Val Ser Gly Ala Ser Gly Gly Ser
                85                  90                  95

Lys Pro Thr Cys Pro Pro Pro Glu Leu Leu Gly Gly Pro Ser Val Phe
                100                 105                 110

Ile Phe Pro Pro Lys Pro Lys Asp Thr Leu Met Ile Ser Arg Thr Pro
                115                 120                 125

Glu Val Thr Cys Val Val Val Asp Val Ser Gln Asp Asp Pro Glu Val
                130                 135                 140

Gln Phe Thr Trp Tyr Ile Asn Asn Glu Gln Val Arg Thr Ala Arg Pro
145                 150                 155                 160

Pro Leu Arg Glu Gln Gln Phe Asn Ser Thr Ile Arg Val Val Ser Thr
                165                 170                 175

Leu Pro Ile Ala His Gln Asp Trp Leu Arg Gly Lys Glu Phe Lys Cys
                180                 185                 190

Lys Val His Asn Lys Ala Leu Pro Ala Pro Ile Glu Lys Thr Ile Ser
                195                 200                 205

Lys Ala Arg Gly Gln Pro Leu Glu Pro Lys Val Tyr Thr Met Gly Pro
                210                 215                 220

Pro Arg Glu Glu Leu Ser Ser Arg Ser Val Ser Leu Thr Cys Met Ile
225                 230                 235                 240

Asn Gly Phe Tyr Pro Ser Asp Ile Ser Val Glu Trp Glu Lys Asn Gly
                245                 250                 255

Lys Ala Glu Asp Asn Tyr Lys Thr Thr Pro Ala Val Leu Asp Ser Asp
                260                 265                 270

Gly Ser Tyr Phe Leu Tyr Ser Lys Leu Ser Val Pro Thr Ser Glu Trp
                275                 280                 285

Gln Arg Gly Asp Val Phe Thr Cys Ser Val Met His Glu Ala Leu His
                290                 295                 300

Asn His Tyr Thr Gln Lys Ser Ile Ser Arg Ser Pro Gly Lys
```

<210> SEQ ID NO 25
<211> LENGTH: 23
<212> TYPE: PRT
<213> ORGANISM: Artificial
<220> FEATURE:
<223> OTHER INFORMATION: clade C V3 consensus linear, non-biotinylated
      23-mer peptide

<400> SEQUENCE: 25

Asn Asn Thr Arg Lys Ser Ile Arg Ile Gly Pro Gly Gln Thr Phe Tyr
1               5                   10                  15

Ala Thr Gly Asp Ile Ile Gly
            20

<210> SEQ ID NO 26
<211> LENGTH: 35
<212> TYPE: PRT
<213> ORGANISM: Artificial
<220> FEATURE:
<223> OTHER INFORMATION: V3 amino acid sequence

<400> SEQUENCE: 26

Cys Ile Arg Pro Gly Asn Asn Thr Arg Lys Ser Ile Arg Leu Gly Pro
1               5                   10                  15

Gly Gln Thr Phe Tyr Ala Thr Gly Asp Val Ile Gly Asp Ile Arg Lys
            20                  25                  30

Ala Tyr Cys
        35

<210> SEQ ID NO 27
<211> LENGTH: 1359
<212> TYPE: DNA
<213> ORGANISM: Artificial
<220> FEATURE:
<223> OTHER INFORMATION: priming agent nucleotide sequence

<400> SEQUENCE: 27
ctgtgggtca ccgtgtacta cggcgtgccc gtgtggaaag aggccaagac caccctgttc      60
tgcgccagcg acgccaagag ctacgagcgc gaggtgcaca cgtgtgggc cacccacgcc     120 tgcgtgccca ccgaccctga tccccaggaa ctggtcatgg ccaacgtgac cgagaacttc     180
aacatgtgga agaacgacat ggtggaccag atgcacgagg acatcatcag cctgtgggac     240
cagagcctga gccctgcgt gaagctgacc ccctgtgcg tgaccctgaa ctgcacaagc     300
cctgccgccc acaacgagag cgagacaaga gtgaagcact gcagcttcaa catcaccacc     360
gacgtgaagg accggaagca gaaagtgaac gccaccttct acgacctgga catcgtgccc     420
ctgagcagca gcgacaacag cagcaacagc tccctgtacc ggctgatcag ctgcaacacc     480
agcaccatca cccaggcctg ccccaaggtg tccttcgacc ccatccccat ccactactgc     540
gcccctgccg gctacgccat cctgaagtgc aacaacaaga ccttcagcgg caagggccc     600 tgcagcaacg tgtccaccgt gcagtgcacc cacggcatca acccgtggt gtccacccag     660 ctgctgctga acggcagcct ggccgaagag gaaatcgtga tcagaagcga aacctgacc     720 gacaacgcca agaccatcat cgtgcacctg aacaagagcg tggaaatcga gtgcatcagg     780
cccggcaaca caccagaaa gagcatccgg ctgggccctg ccagaccctt ctatgccacc     840
ggcgacgtga tcggcgacat ccggaaggcc tactgcaaga tcaacggcag cgagtggaac     900
gagacactga aacaaggtgtc cgagaagctg aaagagtact caacaagac aatccgcttc     960

```
gcccagcact ctggcggcga cctggaagtg accacccaca gcttcaactg cagaggcgag    1020
ttcttctact gcaacaccte cgagctgttc aacagcaacg ccaccgagag caacatcacc    1080
ctgccctgcc ggatcaagca gatcatcaat atgtggcagg gcgtgggcag agctatgtac    1140
gcccctccca tccggggcga gatcaagtgc acctccaaca tcaccggcct gctgctgacc    1200
cgggacggcg gaaacaacaa caacagcacc gaggaaatct tccggcccga gggcggcaac    1260
atgcgggaca attggcggag cgagctgtac aagtacaagg tggtggaaat caagcccctg    1320
ggaatcgccc ccaccgaggc caagcggcgg gtggtgcag                            1359
```